US011167242B1

(12) United States Patent
Parker et al.

(10) Patent No.: US 11,167,242 B1
(45) Date of Patent: Nov. 9, 2021

(54) PROCESS FOR DESULPHERIZATION AND HYDROGEN RECOVERY

(71) Applicants: Melahn L. Parker, Miami, FL (US); Robin Z. Parker, Miami, FL (US)

(72) Inventors: Melahn L. Parker, Miami, FL (US); Robin Z. Parker, Miami, FL (US)

(73) Assignee: Chemergy, Inc., Miami, FL (US)

( * ) Notice: Subject to any disclaimer, the term of this patent is extended or adjusted under 35 U.S.C. 154(b) by 0 days.

(21) Appl. No.: 16/818,281

(22) Filed: Mar. 13, 2020

Related U.S. Application Data

(63) Continuation of application No. 13/893,548, filed on May 14, 2013, now abandoned.

(60) Provisional application No. 61/646,576, filed on May 14, 2012.

(51) Int. Cl.
  *C25B 1/04* (2021.01)
  *B01D 53/14* (2006.01)
  *C07C 7/148* (2006.01)

(52) U.S. Cl.
  CPC ...... *B01D 53/1431* (2013.01); *C07C 7/14825* (2013.01)

(58) Field of Classification Search
  CPC .... C25B 1/04; C25B 9/00; C25B 1/00; C25B 9/18; Y02E 60/364; Y02E 70/10
  See application file for complete search history.

(56) References Cited

U.S. PATENT DOCUMENTS

| 4,105,755 | A | 8/1978 | Darnell et al. |
|---|---|---|---|
| 6,093,306 | A | 7/2000 | Hanrahan et al. |
| 9,702,049 | B1 | 7/2017 | Parker et al. |
| 10,472,721 | B1 | 11/2019 | Parker et al. |
| 2005/0026008 | A1 | 2/2005 | Heaton et al. |
| 2008/0314758 | A1 | 12/2008 | Grosso et al. |
| 2009/0028767 | A1 | 1/2009 | Parker et al. |
| 2009/0308759 | A1 | 12/2009 | Waycuilis |

FOREIGN PATENT DOCUMENTS

WO  WO2009012338  1/2009

OTHER PUBLICATIONS

Parker, Method for Removing Hydrogen Sulfide from Sour Gas and Converting it to Hydrogen and Sulfuric Acid, Dissertation, Stanford University, Jun. 1, 2010.

*Primary Examiner* — Zulmariam Mendez

(57) ABSTRACT

A process for removing hydrogen sulfide from a sour gas stream is presented. The method oxidizes hydrogen sulfide to sulfuric acid by reducing aqueous bromine to hydrobromic acid in solution. The aqueous bromine solution does not react with hydrocarbon components common to natural gas including methane and ethane. This allows the process to both sweeten sour gas and convert its hydrogen sulfide content to sulfuric acid in a single step. In the present process, sulfuric acid is concentrated to eliminate its bromine content prior to being removed from the system, while the remaining hydrobromic acid solution is electrolyzed to regenerate aqueous bromine and produce hydrogen. Hydrobromic acid electrolysis requires less than half the energy required by water electrolysis and is an inherently flexible load that can shed or absorb excess power to balance supply and demand.

11 Claims, 2 Drawing Sheets

FIGURE 2

PROCESS FOR DESULPHERIZATION AND HYDROGEN RECOVERY

BACKGROUND OF THE INVENTION

Field of the Invention

A process removes undesirable amounts of hydrogen sulfide from a sour gas feed stream via reaction with an amount of bromine/hydrogen bromide in a reactor, producing a substantially clean hydrocarbon gas effluent, and solid sulfur/sulfuric acid/hydrobromic acid side streams. The present process also produces economically recoverable amounts of hydrogen gas as a result of processing a hydrobromic acid solution via an electrolyzer stack.

Description of the Related Art

Hydrogen sulfide, or $H_2S$, is a smelly, corrosive and flammable environmental pollutant with toxicity comparable to cyanide. It is colorless and most commonly results from the anaerobic breakdown of organic sulfates, but may occur in volcanic gases from the hydrolysis of sulfide minerals. $H_2S$ is a broad spectrum poison which affects multiple parts of the body. It can block oxygen in mitochondria and stop cellular respiration. The body is able to detoxify it through oxidation to sulfate, so small levels of $H_2S$ can be tolerated.

$H_2S$ gives flatulence and rotten eggs their foul odor, and is very dangerous at low concentrations. It can be smelled at 5 parts per billion ("ppb"), begins to irritate the eyes at 10 ppm, and can no longer be smelled above 200 parts per million ("ppm") because it paralyzes the olfactory nerve. The absence of smell can cause a false sense of safety. A single breath of 800 ppm $H_2S$ is enough to cause immediate collapse and will kill 50% of humans after 5 mins.

$H_2S$ deactivates industrial catalysts, is corrosive to metal piping, and damages gas engines. It must be eliminated from industrial processes, or removed from gas before it is used, transported, or sold. FIG. 2-1 of U.S. Patent Application Ser. No. 61/646,576 incorporated by reference herein in its entirety shows the result of $H_2S$ corrosion on pipes. [Reference 29].

$H_2S$ is commonly found in natural gas, and is made at oil refineries and waste treatment facilities. In 2004 over 9 million tons of $H_2S$ was recovered from refineries and natural gas plants in the U.S. [Reference 30]. Biogas with 0.2-0.4% $H_2S$ is commonly produced in anaerobic digesters of animal waste. [Reference 31]. Natural gas with in excess of 5.7 milligrams of $H_2S$ per cubic meter of gas (0.0004 vol % $H_2S$) is commonly called "sour gas" because of the rotten smell from its sulfur content. [Reference 32].

There are three major sources of hydrogen sulfide: the hydrodesulphurization of petroleum at refineries, the sweetening of sour-natural gas at treatment plants, and biogas from anaerobic digesters and landfills. Biogas is currently an insignificant source of $H_2S$, but is growing due to the greater utilization of anaerobic digesters and landfill gas. In the U.S., refineries account for about 60% of $H_2S$ while natural gas treatment plants account for the remaining 40%. [Reference 33]. Other sources include coke ovens, paper mills, tanneries, gasification plants and coal-bed methane.

Refineries consume 65% of domestic hydrogen production for refining and sweetening oil. The petrochemical industry requires one pound of hydrogen ($H_2$) to remove sixteen pounds of sulfur (S) as hydrogen sulfide ($H_2S$) from refined petroleum products including gasoline, diesel, kerosene and fuel oils in a chemical process known as hydrodesulphurization. Using ethanethiol ($C_2H_5SH$) as the example sulfur compound common in petroleum products, the hydrodesulphurization reaction can be expressed as:

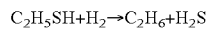
$$C_2H_5SH + H_2 \rightarrow C_2H_6 + H_2S \qquad \text{Eq. 2-1}$$

The product $H_2S$ is collected and purified to yield a nearly 100% $H_2S$ stream. In 1996 more than 5 million tons of $H_2S$ waste was generated in the U.S. through hydrodesulphurization to remove sulfur compounds from crude oil. [Reference 34]. Each year the amount of sulfur in domestically refined crude oil increases. FIG. 2-2 of U.S. Patent Application Ser. No. 61/646,576 incorporated by reference herein in its entirety shows the rise in average sulfur content of refined crude oil. [Reference 35].

As demand for liquid fuels increases and conventional oil reserves are depleted, there is an increasing need to sweeten ever more sour-crude oil, which results in the production of increasing amounts of hydrogen sulfide. A migration to coal-to-liquids technologies and coal gasification will further increase the amount of $H_2S$ generated, and require solutions to both remove $H_2S$ from hydrocarbon (synthesis-) gas streams and convert it to a benign substance.

Sour-gas is distributed all over the world with particularly large mega-field reservoirs in the Caspian Sea, Middle East, Canada, and Asia-Pacific, and smaller more distributed fields being common in the U.S. and other regions where extensive natural gas development has occurred. While sour gas is defined as having greater than 4 ppmv $H_2S$, these sour-gas fields average anywhere from 10-30 wt % $H_2S$, and their product sour natural gas must have its $H_2S$ removed prior to being delivered to market.

The United States has technically recoverable natural gas reserves estimated at up to 1,200 trillion cubic feet, but much of this gas is contaminated with $H_2S$ and thus considered low-quality. [Reference 36]. Removing large quantities of $H_2S$ from natural gas is costly, and as a result, large reserves of natural gas in the United States remain unused. About 17% of all presently exploited gas reserves in the United States have unacceptable levels 20 of $H_2S$. [Reference 37]. Canada represents an even larger source of $H_2S$ as over 40% of the natural gas in Alberta is considered sour. [Reference 38].

Over 20% of ExxonMobile's reserve base, 10% of their proven reserves, and 20% of their undeveloped opportunities consist of sour-gas. [Reference 39]. New natural gas developments can have over 30 wt % $H_2S$ coming out of the ground, and the remaining natural gas reserves around the world are predominantly sour resources. [Reference 40]. Table 2-1 shows the typical gas components of two representative sour-gas wells.

Large sour-gas fields, like ones in North America and those near liquefied natural gas (LNG) terminals being built around the world, have the sulfur removed because the value of natural gas justifies it. Sour-gas has no value, and is in fact a liability, but sweetened natural gas is worth a lot, over $4/MMBtu in the U.S. at mid 2009 prices.

Other large sour-gas fields that produce oil will re-inject byproduct sour-gas back into the ground to maintain reservoir pressure, often because the sour-gas cannot be economically sweetened and conveyed to a market. Smaller sour-oil fields that do not practice reinjection, burn the gas in a flare to convert the dangerous $H_2S$ to less dangerous $SO_2$. [Reference 41].

The most common local sources of $H_2S$ come from the anaerobic bacterial breakdown of organic matter in wastewater treatment plants, city landfills, and septic tanks. Many landfills and waste water treatment plants capture this H$_2$S along with methane and CO$_2$ in the form of biogas which is used for electricity and/or heat. While H$_2$S is only 0.1-2% of the gas stream it must be removed before the biogas is used to prevent corrosion and sulfur emissions. The H$_2$S concentration of biogas is dependent on the digested feedstock, which if high in sulfur can lead to greater concentrations of H$_2$S. Table 2-1 shows typical components of biogas and landfill gas.

Coal-bed methane (CBM) occurs when methane produced from bacterial action adsorbs onto the surface of coal. In the past this methane was vented to the atmosphere prior to the extraction of coal for safety reasons, but now this resource is captured prior to mining. CBM is also produced from wells drilled down to unminable coal seams deep underground. CBM has a relatively low amount of H$_2$S, but this still must be removed to meet pipeline specifications. Table 2-1 in the following section shows the typical components of such gases.

Over 100 trillion cubic feet of coal-bed methane reserves are deemed economically viable to produce out of a reserve base of 700 trillion cubic feet in the U.S. CBM currently provides about 10% of U.S. natural gas production. FIG. 2-3 of U.S. Patent Application Ser. No. 61/646,576 incorporated by reference herein in its entirety shows the major domestic CBM reserves.

Alberta and British Columbia in Canada are estimated to have 170 and 90 trillion cubic feet of coal-bed methane respectively. [Reference 42]. Australia and China are other countries that have developed some of these resources. CBM deposits are largely unexploited, but are found under approximately 13% of the Earth's surface where deep unminable coal seams occur. Therefore they represent an important low-carbon fossil energy resource for much of the world.

Refineries and natural gas treatment plants produce a nearly 100% H$_2$S gas from the hydrodesulphurization of crude oil and sweetening of natural gas due to the processes they currently utilize. Sour-natural gas and biogas components vary immensely over different regions based on the characteristics of the source materials.

Table 2-1 shows some example sour gas mixtures. Sour-natural gas typically contains methane along with higher hydrocarbons such as ethane, propane, butane, pentane and heavier species. Carbon dioxide, steam and nitrogen are common contaminants as well. The amount of H$_2$S can vary greatly, with some wells being over 50% H$_2$S. [Reference 43].

Biogas from a digester is made up of near equivalent shares of methane and carbon dioxide with smaller amounts of ammonia and hydrogen sulfide. Coal-bed methane is mostly methane with varying amounts of carbon dioxide.

Landfill gas has a large fraction of nitrogen, and very small amounts of volatile compounds found in rubbish, including: toluene, dichloromethane, ethyl benzene, acetone, vinyl acetate, vinyl chloride, methyl ethyl ketone, benzene, xylenes, chloroethanes and chloroethylenes. These compounds are typically destroyed when the landfill gas is burned.

The predominant method of treating H$_2$S involves a three step multistage process in which a sour gas stream is contacted with an amine scrubbing solution. The lean H$_2$S amine solution absorbs H$_2$S preferentially and is sent as a rich solution to a stripping column where it is heated to release absorbed H$_2$S. This relatively pure H$_2$S is then sent to a modified-Claus sulfur plant where ⅓ of it is burned with air to create SO$_2$, which is mixed with the remaining H$_2$S to form steam and molten sulfur. This occurs in two or more catalytic stages. Sulfur is removed at each stage, and the final gas stream is flared to convert residual H$_2$S into less harmful SO$_2$. The predominant method of removing H$_2$S from sour natural gas streams is to absorb it into a mixture of amines using a contact tower. FIG. 2-4 of U.S. Patent Application Ser. No. 61/646,576 incorporated by reference herein in its entirety shows the process flow for such a system, which despite being proven, is complicated and requires significant energy input. [Reference 44].

Amines have a high affinity for H$_2$S and preferentially absorb H$_2$S into solution. Once the amines have absorbed H$_2$S, and are considered spent, they are heated to liberate the absorbed H$_2$S which is then captured as a concentrated gas. This is a temperature swing absorption process, and while it cleans the sour-gas stream, it does not treat the H$_2$S which is sent to a modified-Claus plant for conversion to sulfur. The process requires heat and makeup amines must be added periodically, but the process is widely used and well understood.

Some common amines are shown in FIG. 2-5 of U.S. Patent Application Ser. No. 61/646,576 incorporated by reference herein in its entirety. Each has a different affinity for hydrogen sulfide and carbon dioxide at different temperatures. This allows two different amine plants to remove CO$_2$ and then H$_2$S or vice versa to get relatively pure streams of each.

In general, the removal of a pound of H$_2$S requires 500 Btu of heat and 25 Btu of electricity, but these numbers can vary depending on the size of the amine plant. Regenerative amine plants are not deemed economical at capacities below 1,000 pounds of H$_2$S per day. In such instances sacrificial methods are used which produce a product that is land filled.

Economics were obtained for a small amine system for treating a 250 thousand standard cubic feet per day (scf/day) with 0.6 vol % H$_2$S. [Reference 45]. The total system costs $79,246 new, but would be available used for $40,000. This equipment was leased for $2,700 per month (including maintenance), amines cost $1,200 per month, and other expenses amounted to $400 per month for a total annual cost of $51,600.

The equipment removes 22 tonne of H$_2$S a year. It costs $2,300 per tonne of H$_2$S, which corresponds to costing 58 per MMBtu of natural gas sweetened. This H$_2$S must still be treated as these amine plant costs are only for purifying it from a sour-natural gas stream.

The 100 year-old, multi-step Claus process is the most widely used method for treating hydrogen sulfide from crude oil, refined petro-products and raw natural gas desulphurization. The process requires a pure hydrogen sulfide stream, and consequently requires an amine scrubber to extract and purify the hydrogen sulfide from the sour gas.

This concentrated H$_2$S is sent to a modified Claus plant for conversion into elemental sulfur and water with the overall reaction below. The reaction is a little endothermic, but the heat required for reaction is provided by the condensation of gaseous sulfur to liquid sulfur product:

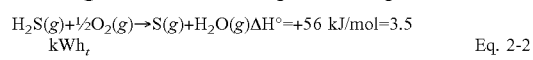
$$H_2S(g)+\tfrac{1}{2}O_2(g) \to S(g)+H_2O(g) \Delta H°=+56 \text{ kJ/mol}=3.5 \text{ kWh}_t \qquad \text{Eq. 2-2}$$

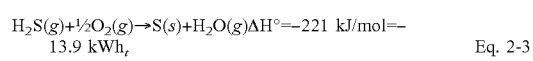
$$H_2S(g)+\tfrac{1}{2}O_2(g) \to S(s)+H_2O(g) \Delta H°=-221 \text{ kJ/mol}=-13.9 \text{ kWh}_t \qquad \text{Eq. 2-3}$$

The process occurs in several stages (usually three) in which a third of the sulfide gas stream is first oxidized by air or oxygen to form sulfur dioxide:

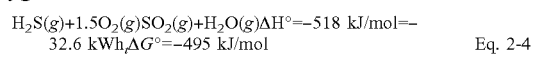
$$H_2S(g)+1.5O_2(g) SO_2(g)+H_2O(g) \Delta H°=-518 \text{ kJ/mol}=-32.6 \text{ kWh}_t \Delta G°=-495 \text{ kJ/mol} \qquad \text{Eq. 2-4}$$

This stream is mixed with the remaining two-thirds of the hydrogen sulfide stream and passed over multiple (usually three) catalyst beds to produce liquid sulfur via the Claus reaction:

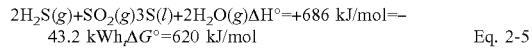

$$2H_2S(g)+SO_2(g) \to 3S(l)+2H_2O(g) \quad \Delta H°=+686 \text{ kJ/mol}=-43.2 \text{ kWh}, \Delta G°=620 \text{ kJ/mol} \quad \text{Eq. 2-5}$$

The first reaction is very exothermic and supplies most of the heat required for the endothermic catalytic 2nd reaction to produce sulfur. Thus overall there is minimal opportunity to utilize the heat of reaction.

FIG. 2-6 of U.S. Patent Application Ser. No. 61/646,576 incorporated by reference herein in its entirety shows a typical implementation of the process. Approximately 50% of the $H_2S$ is converted thermally in the burning process, while each catalytic section converts about 60% of the remaining $H_2S$ for a total removal of 97%.

A 100 tonne sulfur per day modified-Claus plant costs ~$70 million installed with annual operating, maintenance and fixed charges amounting to $14 million a year. [Reference 46]. This corresponds to an operating cost of at least $380 per tonne of sulfur produced, or $360 per tonne of $H_2S$ treated. When the capital cost of the plant (7% WACC) at a realistic utilization rate (80%) and lifetime (15 years) is included the cost to treat a tonne of $H_2S$ rises to over $600. This corresponds to costing 15 per MMBtu of natural gas sweetened using the 0.6 vol % $H_2S$ amine plant example.

Claus plants are expensive to build and operate, require large land areas, and consume significant amounts of energy. Furthermore, they only treat 97% of the sulfide gases, and also require a tail gas unit to remove the remaining sulfide gases or convert them to less harmful sulfur dioxide. [Reference 47].

Enormous expenditure goes into removing $H_2S$ and converting it to sulfur, which is often not valuable enough to transport and accumulates around the desulphurization facility. When prices are low, the liquid sulfur is poured into large blocks to solidify for long term storage. Later, when prices justify, it is flaked, re-melted with steam and shipped to market. Sulfur is burned where needed to produce the more useful sulfuric acid.

FIG. 2-7 of U.S. Patent Application Ser. No. 61/646,576 incorporated by reference herein in its entirety shows a 25 ft high block near Cremona, Alberta, Canada, while on the right is a 60 ft tall block that used to exist in Hoskins Mound, Tex. [Reference 48]. There are several dozen such blocks in Western Canada and the Rocky Mountain foothills next to sour gas production facilities. Some of these are visible from space. [Reference 49].

The combination of amine scrubber with modified-Claus plant, while effective, is prohibitively expensive at small scales and requires very large plants to be economical. Small sour natural gas sources must be connected to a central desulfurization facility through $H_2S$ corrosion resistant stainless steel pipelines, or have their $H_2S$ removed at the source by smaller amine plants and then transported by truck to the central facility. Both of these options are expensive, hindering the development of sour natural gas resources.

Occasionally petroleum refineries are forced to vent sour gas when pressure builds up to unacceptable levels. This vented gas is flared or burned up to consume the HS and produce less toxic $SO_2$, which then becomes acid rain. The flare also produces 100-150 additional unregulated pollutants, and wastes the energy captured in the $H_2S$ laced methane. Most refineries in the U.S. only flare in emergency situations, but around the world in less populated areas it is a normal means of disposing of gas. Example Flares are shown in FIG. 2-8 of U.S. Patent Application Ser. No. 61/646,576 incorporated by reference herein in its entirety. [Reference 50].

Small oil-fields will also flare their sour-gas when stricter environmental regulations do not exist and economics do not justify recovering the gas. This occurs when oil is produced in areas without a gas infrastructure or nearby gas market, and is estimated to result in the release of 390 million tons of carbon dioxide a year which is about 1.5% of anthropogenic $CO_2$ emissions. [Reference 51].

A further problem with flaring is that it often does not lead to complete combustion which puts exceptionally strong greenhouse gases and pollutants in the environment. The Alberta Research Council concluded that flares only burn 62% to 84% of the gases due to the effect of crosswinds and unsteady operation. [Reference 52]. While flaring does also occur for nonsour gases, in many situations in Africa, the former USSR, the Middle East and Asia it is the only solution for sour-gases.

Other methods of removing hydrogen sulfide gas fall into six categories: absorption, adsorption, chemical conversion, membrane permeation, condensation, and biofiltration.

The amine scrubber previously described is an absorption process. Other absorptive methods include treating with: metal oxides, chelated iron, quinone, vanadium, nitrite, alkaline salts, and other solvents, some of which are high-cost, non-regenerable reagents.

LO_CAT® is an iron-redox regenerative system that converts hydrogen sulfide into elemental sulfur. Raw gas is scrubbed with a catalyst solution to form sulfur and the treated gas exits the absorber. The catalyst is regenerated using air and returned to the absorber while elemental sulfur is filtered out of the solution. A 1 MM scf/day (28,317 $m^3$/day) LO-CAT® system costs from $1-2 million depending on hydrogen sulfide concentration. The operating cost alone is $220 per tonne of sulfur removed.

In adsorptive processing, a material sorbs $H_2S$ onto its surface, and is then regenerated in a separate step by reducing the pressure or raising the temperature. This process is similar to absorption with amines, but occurs on the surface of a solid. Other absorptive media include zeolites, activated carbon, and other minerals. The disadvantage of adsorptive processing is that the absorptive media must be periodically replaced or recharged.

Chemical conversion is a common method for treating $H_2S$ from tail gas, landfill gas, anaerobic digesters, and other sources with a relatively low concentration and volume. A metal oxide, such as iron, zinc or sodium is placed in the path of a flowing gas stream contaminated with hydrogen sulfide. The metal oxide reacts with the hydrogen sulfide to produce water and a metal sulfide. Small $H_2S$ producers may scrub with hydrogen peroxide or NaOH to eliminate $H_2S$ very effectively.

A common example is iron oxide going to iron sulfide, which can then be disposed, or regenerated to produce sulfur and iron oxide again. SULFUR-RITE® is a solid scavenger process that converts hydrogen sulfide into iron sulfide. Raw sour gas saturated with water passes over a media bed to form iron sulfide and water with the sweetened gas exiting the system. A $41,000 system capable of treating 1 MM scf/day (28,317 m3/day) has operating costs of $6,600 per tonne of sulfur removed due to the cost of media.

Biological treatment requires passing low-level hydrogen sulfide containing gases through wet biologically active beds including: soil filters, biofilters, fixed film bioscrubbers, suspended growth bioscrubbers and fluidized bioreactors where the hydrogen sulfide is biologically oxidized. Biological treatment is most suitable for processing biogas from anaerobic digesters as the levels of hydrogen sulfide are low and will not kill the bio-organisms; however, treatment the rate is slow and the yields are low.

An emerging process under development by Argonne and KPM researchers is a molten copper reactor to separate hydrogen from $H_2S$. In the reactor, $H_2S$ gas is bubbled though molten copper, which releases hydrogen and forms copper sulfide. The copper sulfide is reacted with air to recover pure copper, releasing a concentrated stream of sulfur dioxide, which is then reacted with water to form sulfuric acid. The copper is then reused with minimum losses. The reactions between the hydrogen sulfide, copper, copper sulfide and air release energy that help keep the system at 1,200° C. This process is interesting because it produces hydrogen, but may suffer from operation at such high temperatures.

In the U.S. there are 150 refineries processing over 18 million barrels of crude oil daily. The amount of hydrogen consumed and lost in desulphurization depends of the sulfur content of the crude oil, but as shown in FIG. 2-2 of U.S. Patent Application Ser. No. 61/646,576 incorporated by reference herein in its entirety this has been rising. In 2005 roughly 550,000 tons of hydrogen went to desulphurization. Refineries can benefit from reducing or eliminating their need to continually consume fossil hydrogen for desulphurization, and are investigating ways to make the $H_2$ they consume carbon neutral. [Reference 53].

Claus plants form water from the hydrogen used to remove sulfur. In 2005, 8.8 million tons of elemental sulfur was recovered from hydrodesulphurization domestically. In the recovery, 1.1 billion pounds of hydrogen reagent was lost in the formation of water.

Hydrogen has a minimum value of 1.45 times the price of natural gas, which at $7/MMBtu, gives the hydrogen a value of $10.15/MMBtu or $0.52 per lb. [Reference 54]. In 2005 the U.S. petrochemical industry lost $572 million worth of hydrogen in the desulphurization of its petroleum products. Globally 64 million tons of sulfur was recovered in 2005 from hydrodesulphurization, consuming 4 million tons of hydrogen valued at over $4 billion. $H_2S$ removal from sour gas and refineries is an $8 billion a year market.

The existing methods for $H_2S$ control are capitally intensive and require large scale implementations to be affordable. Because of the unfavorable economics, smaller natural gas wells must pipe their sour-gas from multiple wells through corrosion resistant and expensive stainless steel piping to a central desulfurization facility. Of 130 trillion cubic feet (TCF) of natural gas produced in the world, 5 TCF are flared and 15 TCF are reinjected into the ground corresponding to 18% of world natural gas demand. Alberta, Canada alone has 6500 flare stacks operating. [Reference 55]. Refineries and sour-oil field developers could make use of the 20 TCF of unused gas with a method for cleaning these gases to recover the natural gas and eliminate $H_2S$ and $SO_2$ emissions.

Hydrogen is an essential chemical feedstock and processing agent used in oil refining, the chemical synthesis of ammonia, methanol, and other products, and for processing steel, glass and other specialty needs. [Reference 56]. In June 2008, the hydrogen market was valued at ~$26 billion. Some of hydrogen's uses are illustrated in FIG. 2-9 of U.S. Patent Application Ser. No. 61/646,576 incorporated by reference herein in its entirety.

Annually the country can produce about 10.7 million metric tons of hydrogen as a chemical commodity consisting of ~9 million metric tons captive, that is hydrogen consumed where produced, and ~1.7 million metric tons of merchant, which is hydrogen stored, transported and sold for a variety of uses. [Reference 57]. 1.2 million metric tons of the merchant production was sent to refineries through over-the-fence arrangements in which the hydrogen is produced next door.

Refineries have driven most increases in domestic $H_2$ demand recently as they require more hydrogen to meet tightened sulfur restrictions in diesel fuel and refine increasingly poor quality high-sulfur crude oil. It is interesting to note that the augmentation in domestic hydrogen capacity has benefitted Americans by allowing domestic refineries to purchase lower quality crude oil, i.e. from Venezuela, at a discount that other countries cannot refine. The increased $H_2$ capacity also allows a greater fraction of crude oil to be upgraded to lighter and more valuable gasoline and diesel while reducing the amount of undesirable heavy oil produced.

The increase in hydrogen demand at refineries has been tempered by reductions from the ammonia industry due to the high domestic price of natural gas. Since 1999 25 ammonia plants have closed permanently, corresponding to a 44% decline in domestic ammonia production between 2000 and 2006. The difference in production and demand has largely been made up through imports. [Reference 58].

Almost 2.3 million metric tons of hydrogen production capacity is currently dedicated to ammonia each year, corresponding to 20% of domestic hydrogen production, and 33% of dedicated hydrogen produced from natural gas. Worldwide ammonia uses 50% of global hydrogen produced. [Reference 59]. Methanol is another large consumer of hydrogen, with almost 200 thousand metric tons of hydrogen production capacity dedicated to it every year. Methanol capacity has declined by 86 percent between 2000 and 2006, and there are only two methanol plants currently operating in the U.S., again due to high natural gas prices.

The most common and least expensive method of producing hydrogen in the U.S. is Steam Methane Reforming (SMR) with production cost dependent on the price of natural gas. About 5% of the nation's natural gas demand is used to produce 6.8 million metric tons of hydrogen annually. [Reference 60]. This hydrogen is almost entirely for use in refineries and ammonia/methanol plants.

Water-electrolysis produces ~500 tons of hydrogen annually serving niche markets, but is touted as the method for producing large quantities of $H_2$ in the future. Other approaches that gasify, catalyze and decompose hydrogen-carriers are under investigation.

SMR is an endothermic, high-temperature (650-1,000° C.), high-pressure (600 psi) process in which methane is partially oxidized to syngas and reacted with steam in a water-gas shift reaction. It consumes natural gas, produces greenhouse gases, is only 70% energy efficient, and requires substantial capital due to catalysts, high process pressures and temperatures. [Reference 61]. Natural gas production is strained to meet growing domestic demand and its price has risen recently, as illustrated in FIG. 2-10 of U.S. Patent Application Ser. No. 61/646,576 incorporated by reference herein in its entirety.

The cost of $H_2$ from SMR is proportional to the cost of natural gas feedstock, as is shown in FIG. 2-11 of U.S. Patent Application Ser. No. 61/646,576 incorporated by reference herein in its entirety. If an SMR facility had no fixed cost associated with it, $H_2$ would cost ~1.45 times as much as natural gas on an energy basis because of production losses.

At the June 2008 average natural gas price of $12.80/MMBtu, SMR produces captive 'at-the-gate' $H_2$ for $24.63/MBtu or $1.47/lb. [Reference 62]. This is almost three times as expensive as when many of the SMR plants were built, and resulted in many $H_2$ intensive industries such as fertilizer and methanol production to move overseas. [Reference 63].

The quantity of $H_2$ produced from water electrolysis is inconsequential, but despite the high energy requirements and cost of electrolyzing water, it remains the most common proposed solution for supplying large quantities of carbon neutral $H_2$. Water-electrolysis is the most expensive $H_2$ production process due to three unavoidable reasons: pretreatment of the water feedstock which must be de-ionized, high capital costs from expensive noble metal catalysts that are required, and the high electrical energy needed to dissociate water. It is uncertain where the significant amount of electricity required will come from, as the normally proposed solutions of new nuclear power plants and carbon capturing coal plants are projected to remain expensive.

In 2004, the National Academy of Science (NAS) reviewed the DOE hydrogen, fuel cell and infrastructure program, and recommended that the DOE explore alternatives to water electrolysis to produce low-cost renewable hydrogen. [References 64, 65]. In the same reference, without including distribution and storage costs, the NAS reported that, "due to high-energy requirements and capital-costs, one cannot meet the DOE ($H_2$ cost) goals by electrolyzing water."

Electricity is an expensive, high-value energy product. Hence, a process that reduces the amount of electrical power required to produce hydrogen is in line with expert recommendations. In contrast, HBr electrolysis requires less electricity than water, and readily accepts a contaminated feedstock, which if electrically conductive can act as a 'slurry electrode' to further reduce cell voltage. [Reference 66].

The least expensive hydrogen is that recovered as a byproduct of fossil-fuel processing. In the U.S. last year 3 million metric tons were produced from catalytic reforming at oil refineries. Most of the feedstock for this is naphtha which is a mixture of different hydrocarbons that results from refinery distillation operations. An additional 500 thousand metric tons were recovered from refinery off-gases through various purification processes.

Another interesting source of byproduct hydrogen is from chlor-alkali processes, or the production of chlorine for plastics and water treatment use. The process electrolyzes salt (NaCl) in a concentrated brine to produce hydrogen, caustic (NaOH) and chlorine. In 2006 almost 400 thousand metric tons of hydrogen was produced by the chlor-alkali industry.

Gasification is similar to SMR discussed above, but uses a heavier hydrocarbon feedstock such as oil or coal. The feedstock is partially burned with oxygen to produce hydrogen and carbon monoxide which is then reacted with water in a shift reaction to produce carbon dioxide and more hydrogen.

This process is used in refineries and chemical plants, but is penalized by high costs. The equipment must withstand high temperatures and harsh conditions, which means it must be robust, and the production of slag or solids from the ash components of the fuel leads to maintenance concerns. Nonetheless this is a promising technology for producing hydrogen.

As discussed in the prior work section, hydrobromic acid electrolysis requires significantly less energy than water electrolysis. The theoretical energy of the hydrogenbromine bond is 46% of the hydrogen-oxygen bond, but the actual energy required to form hydrogen from hydrobromic acid azeotrope in an electrolyzer at room temperature is 40% of the actual energy to electrolyze water in practice. [Reference 67].

FIG. 2-12 of U.S. Patent Application Ser. No. 61/646,576 incorporated by reference herein in its entirety shows the theoretical and actual energy of electrolyzing water and 47 wt % concentrated HBr at room temperature.

While the theoretical voltage for water electrolysis is 1.23 Volts, current electrolyzers operate at 2.0 Volts while new advanced electrolyzer designs are pushing this down to 1.8 Volts. Water can be electrolyzed at lower voltages if a lower current density is selected, but due to the high capital cost of water electrolyzers they are operated at less efficient conditions to minimize the total hydrogen production cost which includes fixed capital equipment charges. Operating at a higher current density increases the electricity cost per unit of hydrogen, but spreads the fixed capital cost across more total hydrogen production.

Water electrolyzers are expensive in part because they require catalysts on both the hydrogen cathode and oxygen anode. Hydrobromic acid electrolysis does not require catalysts at the cathode or anode. Only the reversible HBr fuel cell requires a light catalyst loading (about a tenth of oxygen anode loadings) on the bromine anode to generate power from $H_2$ and $Br_2$.

Hydrobromic acid electrolysis requires less energy and power than water electrolysis for a fixed quantity or rate of hydrogen production, and therefore is less expensive by the same margin. At a voltage 40% that of water's, the HBr electrolysis stack and power conversion equipment are correspondingly 60% smaller for a similar hydrogen production rate.

Unlike water, the energy required to electrolyze HBr is strongly dependent on temperature, and decreases at elevated temperatures. [Reference 68]. FIG. 1-10 of U.S. Patent Application Ser. No. 61/646,576 incorporated by reference herein in its entirety shows the open circuit decomposition voltage is significantly reduced at elevated temperatures.

The HBr solution coming from the $H_2S$ reactor is hot; at 80° C. its electrolysis commences at 0.6 Volts, or 16 kilowatt hours of electricity per kilogram of hydrogen produced ($kWh_e/kgH_2$). [Reference 69]. At a modest current density of 3 $kA/m^2$ a polymer membrane electrolyzer operates at 0.8 Volts (21 $kWh_e/kgH_2$), but at 200° C. a pressurized graphite electrode cell will start to decompose HBr at 0.42 Volts (11 $kWh_e/kgH_2$). This is only 21% of the energy required to electrolyze water in state-of-the-art systems [Reference 70], and 34% of the energy released from reacting hydrogen with oxygen. Thus it is possible to generate more electricity from reacting the hydrogen with oxygen, than is required to produce it from hydrogen bromide. Additional information on electrolyzing solutions of hydrobromic acid is presented below.

There are three large growing needs for $H_2$: use in biofuel plants to increase cellulosic ethanol production, use in hydrogen-enriched combustion to reduce nitrogen oxide emissions, and use as a fuel for an evolving $H_2$ economy. Along with these there will continue to be demand in refineries and nitrogen fertilizer plants.

Many biofuel production processes rely on 'bugs' to ferment a cellulosic or sugar-based feedstock into ethanol. The carbohydrates are broken down into alcohols and carbon dioxide which are purified and vented respectively. Other methods gasify feedstock to make carbon dioxide, carbon monoxide and hydrogen with these latter two components being combined over catalysts to produce liquid fuels.

In both processes, carbon dioxide can be reacted with hydrogen to form carbon monoxide and then hydrocarbons or alcohols through the sacrifice of further hydrogen to water.

Bio-feedstock can produce about three times as much liquid fuels when hydrogen is available. [Reference 71]. This corresponds with all a feedstock's carbon being converted to liquid hydrocarbons, and none going to carbon dioxide, which can increase biofuel productivity.

Natural gas fired power plants are a significant source of nitrogen oxide ($NO_x$), especially in urban areas. Combustion turbines in particular are mostly found in urban areas and suffer from very high $NO_x$ emission rates, making them responsible for significant local nitrogen oxide pollution. A typical 115 MW gas turbine will produce 4,400 tons of $NO_x$ a year, which turns into ozone in the presence of volatile organic compounds, heat, and sunlight.

FIG. 2-13 of U.S. Patent Application Ser. No. 61/646,576 incorporated by reference herein in its entirety shows counties deemed ozone nonattainment areas because their ozone levels exceed health standards. [Reference 72]. In 2004, the EPA determined that 159 million Americans live in 474 counties with unsafe ozone smog levels. [Reference 73]. Ozone is a powerful oxidant that burns lungs and airways, causing them to become irritated, inflamed, and swollen. Ozone is linked to increased mortality, birth defects, asthma, respiratory problems, and increased hospitalization rates.

Since 1997, over 1,700 studies on the health and environmental effects of ozone have been published. [Reference 74]. Some conclusions from these studies include:

Exposure to ozone is related to increased mortality, and the inflame response it causes in lungs are particularly problematic for the elderly. Even low levels may cause chest pain and cough, aggravate asthma, reduce lung function, increase emergency room visits for respiratory problems, and lead to irreversible lung damage.

The amount of time children spend outside is directly proportional to higher incidences of asthma in high ozone areas, but not in areas of low ozone.

Women exposed to ozone during their second month of pregnancy have an increased risk of giving birth to babies with serious aortic artery and valve heart defects.

$H_2$ can be used to displace natural gas in 1 vol % $H_2$-enriched natural gas combustion, which can reduce nitrogen oxide emissions by 15%. Burning 5 vol % $H_2$ rich allows 50% $NO_x$ reductions over normal emission rates. The reduction occurs because hydrogen stabilizes natural gas burner flame stability, allowing leaner combustion at lower temperatures to reduce $NO_x$ formation.

Almost half of America's population lives in counties with ozone levels that exceed National Ambient Air Quality Standards. $NO_x$ reductions from $H_2$-enriched natural gas combustion are valuable for the emission credit they create and can improve air quality in many urban environments.

There is growing political and environmental pressure to transition to a hydrogen economy, but there is no viable solution on how to make the large amounts of hydrogen required in a carbon neutral manner.

There is also a 'chicken or egg' problem in that the infrastructure to enable the hydrogen economy does not exist yet. Fortunately hydrogen can be used to make methanol or ethanol liquid fuels during the transition. Either way, renewable hydrogen is necessary to reduce fossil fuel dependence and power the vehicles of the proposed hydrogen, methanol or ethanol economies.

Prior to the emergence of an "$H_2$ economy", $CO_2$ may be reacted with $H_2$ over a catalyst to form methanol, which may be sold or dehydrated with sulfuric acid to form ethanol as shown in FIG. 2-14 of U.S. Patent Application Ser. No. 61/646,576 incorporated by reference herein in its entirety. [Reference 75]. This avoids transportation and storage issues with $H_2$ and creates a useful chemical feedstock or fuel. Ethanol benefits from tax incentives, and can be used in the present fleet of vehicles. The $CO_2$ may also be captured and disposed of to generate carbon credits.

Bromine is the only liquid nonmetallic element under standard conditions. There are two isotopes with 51% being the lighter 79 Dalton atom, and 49% being the heavier 81 Dalton atom. At room temperature, bromine's density is 3.12 g/cc and its partial pressure is 0.28 atm. It boils at 59° C. and freezes at −7° C. Bromine is very active chemically bringing tears to the eyes at 1 ppm and causing respiratory damage at 10 ppm.

Bromine was discovered independently by Antoine Balard and Carl Jacob Lowig in 1825 and 1826, respectively. It is named after the Greek word bromos for stench. Bromine is produced by reacting bromide, usually in the form of sodium bromide, with chlorine to produce bromine which is then removed as a vapor and condensed. Bromine may also be produced from the electrolysis of bromide rich brine.

Most bromine comes from Dead Sea deposits developed due to their very high bromine content exceeding 5,000 ppm. The U.S., China and U.K. produce bromine from saline aquifers with 300 to 5,000 ppm bromide. Seawater has 65 ppm bromide.

Bromine is not a rare element and its reserves are considered unlimited. Currently the U.S. has 725+ million lbs of bromine production capacity, but only makes ~500 million lbs a year at $0.61 per bulk pound. Smaller quantities can cost from $1-3 per pound depending on if delivered by truck or barrel. The $H_2S$ bromination of the present disclosure process does not consume bromine, and is not expected to impact its cost.

Primary uses of bromine include flame retardants (40%), drilling solutions (24%), brominated pesticides such as methyl bromide for termites (12%), water treatment chemicals (7%), and other more specialized uses including photographic/other chemicals, rubber additives and pharmaceuticals (17%).

The use of bromine and bromination is an essential industrial process with well-known industrial safety, material and operating standards. A collection of major industrial companies and organizations concluded using bromine is safe. [Reference 76]. In 2001 the USGS report on bromine clearly stated bromine and its compounds are used safely, and will continue to be used. These results indicate that bromine and its compounds can be considered safe as a result of the established bromine safety standards and practices.

Earlier investigations provide a sound foundation for the inventive process of the present disclosure. These earlier efforts include extensive research on the bromination of sulfur dioxide, and the electrolysis of hydrogen bromide gas and hydrobromic acid solution.

Significant work went into understanding the reaction between sulfur dioxide ($SO_2$), bromine ($Br_2$) and water ($H_2O$) to form sulfuric acid and hydrobromic acid. The reaction and its change in enthalpy at standard state (ΔH°) is displayed below:

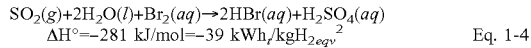

$$SO_2(g)+2H_2O(l)+Br_2(aq) \rightarrow 2HBr(aq)+H_2SO_4(aq)$$
$$\Delta H°=-281 \text{ kJ/mol}=-39 \text{ kWh}_t/\text{kgH}_{2eqv}^2 \quad \text{Eq. 1-4}$$

This reaction was proven to be favorable under efforts in the 1970's and 1980's to develop a hybrid water splitting cycle known as the Euratom Mark-13 process. [Reference 3]. In this process, product sulfuric acid was thermally decomposed to regenerate $SO_2$ reactant along with oxygen and steam, as shown below:

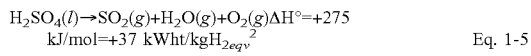

$$H_2SO_4(l) \rightarrow SO_2(g)+H_2O(g)+O_2(g) \Delta H°=+275$$
$$\text{kJ/mol}=+37 \text{ kWht/kgH}_{2eqv}^2 \quad \text{Eq. 1-5}$$

Product HBr was electrolyzed to regenerate $Br_2$ and produce hydrogen as previously discussed. A bench scale system built in 1983 successfully produced 50 liters per hour of hydrogen using the process. [Reference 4]. The reactions were proven to be favorable, but the process was not developed further as traditional hydrogen production methods from fossil fuels were more economical. [Reference 5].

As work on this hydrogen producing cycle was coming to a close, the first reaction of the cycle (Eq. 1-4) was applied to the treatment of $SO_2$ emissions from coal-fired power plants. These power plants were coming under closer scrutiny for their air emissions, and technologies were needed to reduce their emissions to legislated levels. The Mark-13 process was renamed the ISPRA Mark-13A process, and applied to dilute $SO_2$ gas streams with only a few percent $SO_2$ by volume mixed in combustion flue gas (nitrogen, oxygen, carbon dioxide). In this adaptation, the sulfuric acid was concentrated, removed and sold instead of being thermally dissociated. [Reference 6].

In the 1980's work progressed from simulated flue gas streams in the laboratory to actual coal flue gases in the field. At the end of the decade a pilot plant was built and evaluated on a 30 $MW_t$ coal-fired boiler at the Sarras refinery in Italy. [Reference 7]. This pilot plant achieved 97% removal of $SO_2$ emissions, nearly complete regeneration of bromine from HBr, and was considered a success.

Economic studies showed the process had significant operating cost advantages over competing limestone forced oxidation (LSFO) for $SO_2$ removal, but no customers were found, and after several years of marketing the process, it was abandoned. The reasons the process was not adopted may be traced to 15% higher capital costs than LSFO, a move away from coal in Europe (particularly Italy where coal developments were halted), and a U.S.-centric conservative mentality that encouraged the adoption of domestically developed and proven LSFO. [Reference 8].

The reaction between bromine and $SO_2$ was so favorable that the original researchers concluded the process could also be used for controlling $H_2S$ and carbon disulfide. The reaction and change in enthalpy at standard state (ΔH°) for the bromination of $H_2S$ in the presence of water to produce sulfuric acid ($H_2SO_4$) is displayed below:

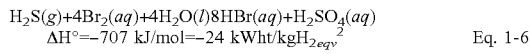

$$H_2S(g)+4Br_2(aq)+4H_2O(l)8HBr(aq)+H_2SO_4(aq)$$
$$\Delta H°=-707 \text{ kJ/mol}=-24 \text{ kWht/kgH}_{2eqv}^2 \quad \text{Eq. 1-6}$$

The process was disclosed in a patent, but no work was ever published on the reactions. [Reference 9]. The original researchers concluded the process could not compete with existing processes in the inexpensive fossil energy environment of the 1990's, and did not pursue experimental investigations. [Reference 10].

Previous work on electrolyzing HBr can be divided into three broad categories: work done in Europe to electrolyze hydrobromic acid as part of the Mark 13 hybrid hydrogen production cycle, work done by the Japanese on gaseous HBr electrolysis again related to hydrogen production cycles, and work performed in the U.S. on reversible HBr fuel cells for use in energy storage applications. [Reference 11].

As part of developing the Mark 13 process for producing hydrogen, the electrolysis of hydrobromic acid was investigated and confirmed to occur at voltages significantly less than water electrolysis. Bipolar graphite electrodes were used with a platinized graphite cathode and smooth graphite anode. The noble metal catalyst platinum reduces the hydrogen overpotential at the cathode significantly. No platinum was used on the anode where exposure to bromine dissolves most catalysts. A diaphragm to separate the anode and cathode at the expense of a higher operating voltage was deemed unnecessary.

The decomposition voltage for a 50 wt % HBr solution at 373 K was found to be 0.75 and 1.0 Volts at 2 kA/m and 8 kA/m current density respectively. [Reference 12]. Results from the European research are shown in FIG. 1-5 of U.S. Patent Application Ser. No. 61/646,576 incorporated by reference herein in its entirety.

Japanese researchers investigated the gas phase electrolysis of HBr. They evaluated PTFE-bonded carbon and graphite-felt electrodes at modest current densities. The advantage of gas-phase electrolysis for thermo-chemical hydrogen production cycles were the lower theoretical decomposition voltage, the production of gaseous bromine, and the ability to directly electrolyze gaseous HBr from a high temperature production process. [Reference 13]. Results from the Japanese research are shown in FIG. 1-6 of U.S. Patent Application Ser. No. 61/646,576 incorporated by reference herein in its entirety.

American researchers first developed hydrogen-halogen fuel cells in the 1960's. The kinetics were favorable and the reaction was found to be nearly reversible. This led to the research and development of hydrogen-chlorine and then hydrogen-bromine energy storage systems at General Electric and Brookhaven National Laboratories. Single cell stacks were used to evaluate different catalysts, catalyst loadings, and membrane types. Their work evaluated HBr decomposition voltages at a wide range of concentrations and modest range of temperatures as shown in FIG. 1-7 and FIG. 1-8 of U.S. Patent Application Ser. No. 61/646,576 incorporated by reference herein in its entirety. [Reference 14]. As well as confirming HBr electrolysis under 1 Volt at modest current densities, their work was particularly interesting for revealing the reversible nature of the hydrogen-bromine electrochemical couple. These researchers used polymer proton exchange membranes that benefited from low overvoltages, with the majority of losses being due to the internal cell resistance. Such cells could be operated in electrolysis mode to produce $H_2$ and $Br_2$ from HBr and electricity or in fuel cell mode to make electricity from $H_2$ and $Br_2$. FIG. 1-9 of U.S. Patent Application Ser. No. 61/646,576 incorporated by reference herein in its entirety shows the voltage of the reversible fuel cell when operated as a fuel cell and electrolyzer at different HBr concentrations and current densities.

Rockwell International evaluated the electrolysis of hydrobromic acid at elevated temperatures as part of a hybrid cycle in which HBr was created from the exothermic bromination of cellulosic feedstock. Rockwell concluded that a 60 wt % HBr solution could be electrolyzed at only 0.75 Volts while operating at a 6 $kA/m^2$ current density and 200° C. FIG. 1-10 of U.S. Patent Application Ser. No. 61/646,576 incorporated by reference herein in its entirety shows the open circuit decomposition voltages for 48 wt % HBr at a range of temperatures.

HBr electrolysis is well understood from decades of work and related experience in the chlor-alkali industry which electrolyzes 'brine' or sodium chloride to produce over 13 million metric tons per year of chlorine. [Reference 19]. The electrolysis of brine is similar to electrolyzing HBr, thus the research objectives are centered on understanding the bromination reaction rates and yields for the thermo-chemical processing of hydrogen sulfide into HBr, and any necessary post-treatment steps for recovering bromine.

The ubiquitous and significant accomplishment of these groups was confirmation that HBr electrolysis could produce hydrogen for significantly less energy than water electrolysis. [Reference 15].

The underlying principle of the present inventive process is found in nature. Hydrogen sulfide from thermal vents in the deep ocean dissolves in salt water and is used by bacteria to form the base of a food chain that supports tubeworms and many other crustaceans. [Reference 16]. FIG. 1-11 of U.S. Patent Application Ser. No. 61/646,576 incorporated by reference herein in its entirety shows a close-up view of tubeworms (*Riftia pachyptila*), bathed in dilute hydrothermal fluids, at water depths over 2.5 km under the Pacific Ocean.

These worms tolerate high temperatures and sulfide concentrations, and use the red "plume" that contains hemoglobin to exchange compounds with the environment, e.g., hydrogen sulfide, carbon dioxide, oxygen, etc. The hydrogen sulfide is used by symbiotic bacteria held in an internal organ to make energy.

Methane clatharates form at high pressure and low temperature when water and methane freeze to form a solid. Methane clatharate deposits are very common in the deep ocean, and thought to contain several orders of magnitude more carbon than present in the atmosphere. [Reference 17].

In many parts of the ocean methane rises to the surface unreacted with saltwater from methane hydrates melting in ocean sediments. [Reference 18]. FIG. 1-12 of U.S. Patent Application Ser. No. 61/646,576 incorporated by reference herein in its entirety shows methane bubbling up from the bottom at 600 meters depth. This occurs because methane is not soluble in water and is inert at moderate temperatures. No known organisms survive on methane.

The natural phenomenon of hydrogen sulfide dissolving and reacting with water while methane does not dissolve and bubbles to the surface illustrates the physical properties that allow an aqueous bromine solution to react with $H_2S$ while not affecting methane.

The present disclosure focuses on answering questions about the reaction of bromine with hydrogen sulfide to produce hydrobromic and sulfuric acids, and the decomposition of hydrobromic acid in an electrolyzer.

The results obtained by Applicant are categorized into three primary areas: understanding the theoretical expectations of the bromine desulphurization process; performing experiments to verify the process's efficacy; and estimating the process's economics to justify future work.

Theoretical performance evaluated by Applicant includes: calculating expected thermodynamic equilibrium; identifying potential reaction products and reaction mechanism; calculating theoretical decomposition potential of hydrobromic acid; and, analyzing process flow and energy balance.

Experimental testing performed by Applicant includes: confirming removal of $H_2S$ in excess of 99.9% with aqueous $Br_2$ solution; evaluating reaction rates, kinetics, and/or mass transfer limits; identifying form of sulfur product and establish methods to remove and purify it; closing bromine and sulfur mass balances (99+% accounting); confirming efficacy of water scrubber to capture bromine/HBr vapors; identifying undesirable reactions between bromine, hydrocarbons and sulfur; evaluating electrolysis of hydrobromic acid in multi-cell stack; and, investigating effect of concentration on hydrobromic acid electrolysis.

Economic evaluation performed by Applicant includes: identifying process equipment requirements; process flow for prototype with energy and mass balance; estimating hydrogen production cost; and, constructing an integrated demonstration to convert $H_2S$ into hydrogen and sulfur.

Applicant seeks to overcome problems associated with hydrogen sulfide removal. In the course of testing, methods for reacting hydrogen sulfide with bromine and water are investigated. The principal issues to be overcome involve the potential side reactions of bromine with carbonaceous species such as methane, and the possibility that the $H_2S$ will not react with bromine. Secondary issues involve the effect of sulfur and/or sulfuric acid on HBr electrolysis and concerns with bromine material compatibility. A literature review suggests neither of these will be a problem.

The principal invention is a process capable of capturing the heretofore lost value of hydrogen sulfide by producing hydrogen and sulfuric acid from its treatment. The present inventive process has potential to simplify the treatment of this dangerous contaminant, increase natural gas and hydrogen supplies, and convert sulfur waste into useful sulfuric acid.

It would be beneficial to provide a method for regenerating hydrogen consumed in the hydrodesulphurization of petroleum products, provide net hydrogen from the sweetening of sour-natural gas and bio-gas, and reduce carbon dioxide emissions from steam methane reforming of natural gas into hydrogen.

Nationwide the process could increase exploitable domestic natural gas reserves by 168 Trillion Cubic Feet (TCF) by opening up presently undrilled sour-gas reserves. [Reference 20]. The opportunity is even greater in other regions, the UAE for instance has over 200 TCF of sour gas. [Reference 21]. The process can also increase supply by recovering $H_2S$ contaminated natural gas that is currently flared or re-injected into the ground around the world. [Reference 22].

Over 23 TCF of natural gas is consumed domestically each year. [Reference 23]. A supply/demand elasticity of 5 means this increased supply would reduce the cost of natural gas 3%, or 21¢/MBtu. [Reference 24]. This would reduce the cost to generate electricity in Natural Gas Combined Cycle (NGCC) plants by 2% to 11.76 ¢/kWh and save utilities and ratepayers $150 million a year in the State of California alone. [Reference 25].

If all 25 million tons of global man-made $H_2S$ emissions were treated with the present inventive process, 12 billion pounds of hydrogen, or 20% of the current global merchant hydrogen market would be produced. [Reference 26]. If consumed in a 50% efficient fuel cell or combustion turbine 72 billion kWh of energy would be produced, amounting to 0.4% of total global annual electricity demand. [Reference 27]. Use of the hydrogen and natural gas on-site where it is produced and sweetened respectively can improve air quality nationwide by reducing emissions of $H_2S$ and $SO_2$ and provide transmission and distribution benefits. [Reference 28]

Using hydrobromic acid electrolysis to produce large quantities of hydrogen may encourage the adoption of electrical energy storage. Additional benefits stem from the large scale use of electrolyzers, which by shedding load or absorbing excess power can allow the grid to operate more efficiently by eliminating the need for a spinning reserve and allowing greater sourcing from intermittent renewable power.

SUMMARY OF THE INVENTION

A process is provided for desulphurization and hydrogen recovery from an influent stream, such as a sour gas influent stream, wherein the influent gas stream may including an amount of methane and/or ethane gas, as well as trace amounts of other hydrocarbon gases, as well as an undesirable amount of hydrogen sulfide.

In at least one embodiment, the process comprises a reactor structured to facilitate reaction of a sour gas influent stream with an amount of bromine and/or hydrogen bromide. In at least one embodiment, the amount of bromine and/or hydrogen bromide is presented counter currently to the sour gas influent stream in a reactor column. Of course, concurrent, as well as other reaction schemes may be utilized, in at least some embodiments of the present invention.

The reactor is structured to produce a gaseous effluent stream comprising substantially all of the methane gas, ethane gas, as well as any other hydrocarbon gases present in the influent sour gas stream. The reactor, in at least one embodiment, is further structured to produce an effluent stream comprising an aqueous solution of hydrobromic acid, sulfuric acid, and an amount of solid sulfur. A filter may be employed in at least one embodiment, to remove solid sulfur from the aqueous acid effluent stream of the reactor.

At least one absorber is incorporated into the process, the absorber structured to separate carbon dioxide gas and water vapor from the methane and other hydrocarbon gases in the gaseous effluent stream of the reactor. The at least one absorber is further structured to discharge an amount of a dilute aqueous hydrobromic acid solution, which in one further embodiment, is recirculated back to the reactor.

An electrolyzer is structured to electrolytically disassociate the hydrobromic acid solution into an aqueous solution of hydrogen bromide and bromine. In at least one embodiment, the electrolyzer is further structured to produce an amount of hydrogen gas and water vapor via dissociation of the hydrobromic acid solution. In such an embodiment, a second absorber may be employed which is structured to separate water vapor from the hydrogen gas produced via dissociation of the hydrobromic acid solution. In one further embodiment, the second absorber is also structured to discharge an amount of a dilute aqueous hydrobromic acid solution which, as before, may be recirculated back to the reactor.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

Figure 2:
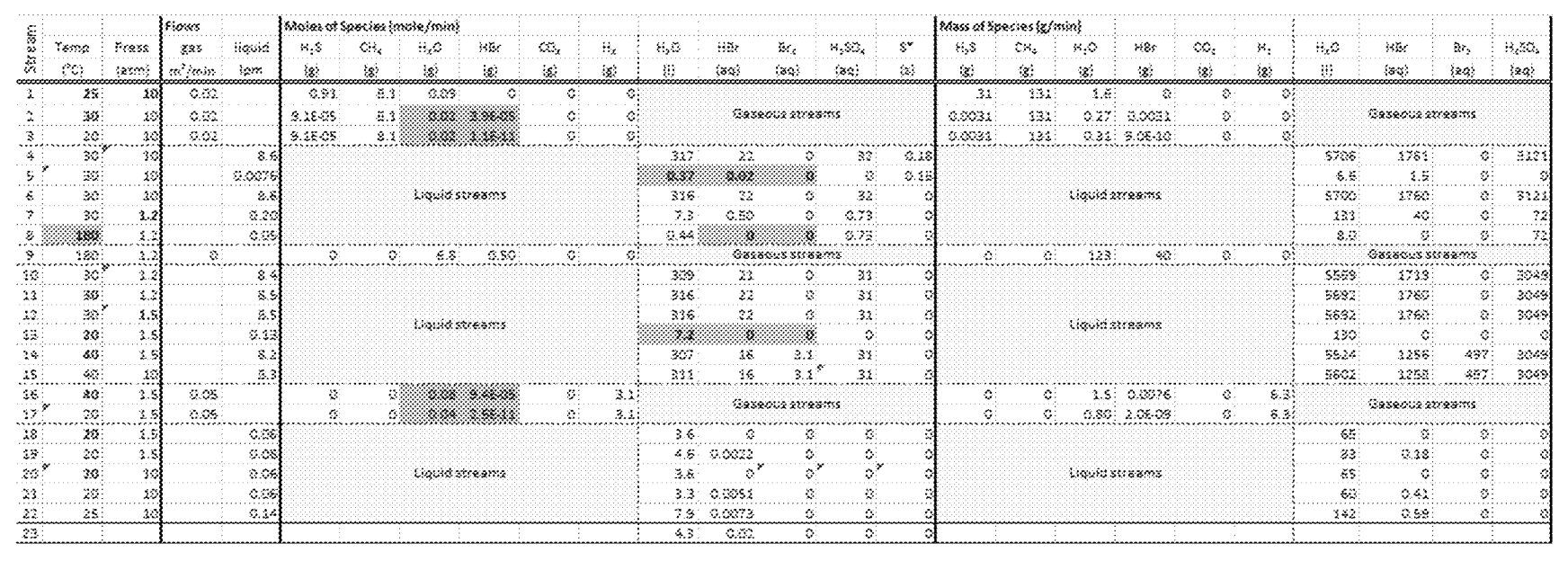

FIG. 2 is a tabular presentation of a mass balances for the pilot scale desulphurization and hydrogen recovery system illustrated in FIG. 1.

Like reference numerals refer to like parts throughout the several views of the drawings.

DETAILED DESCRIPTION OF THE PREFERRED EMBODIMENT

Figure 1:
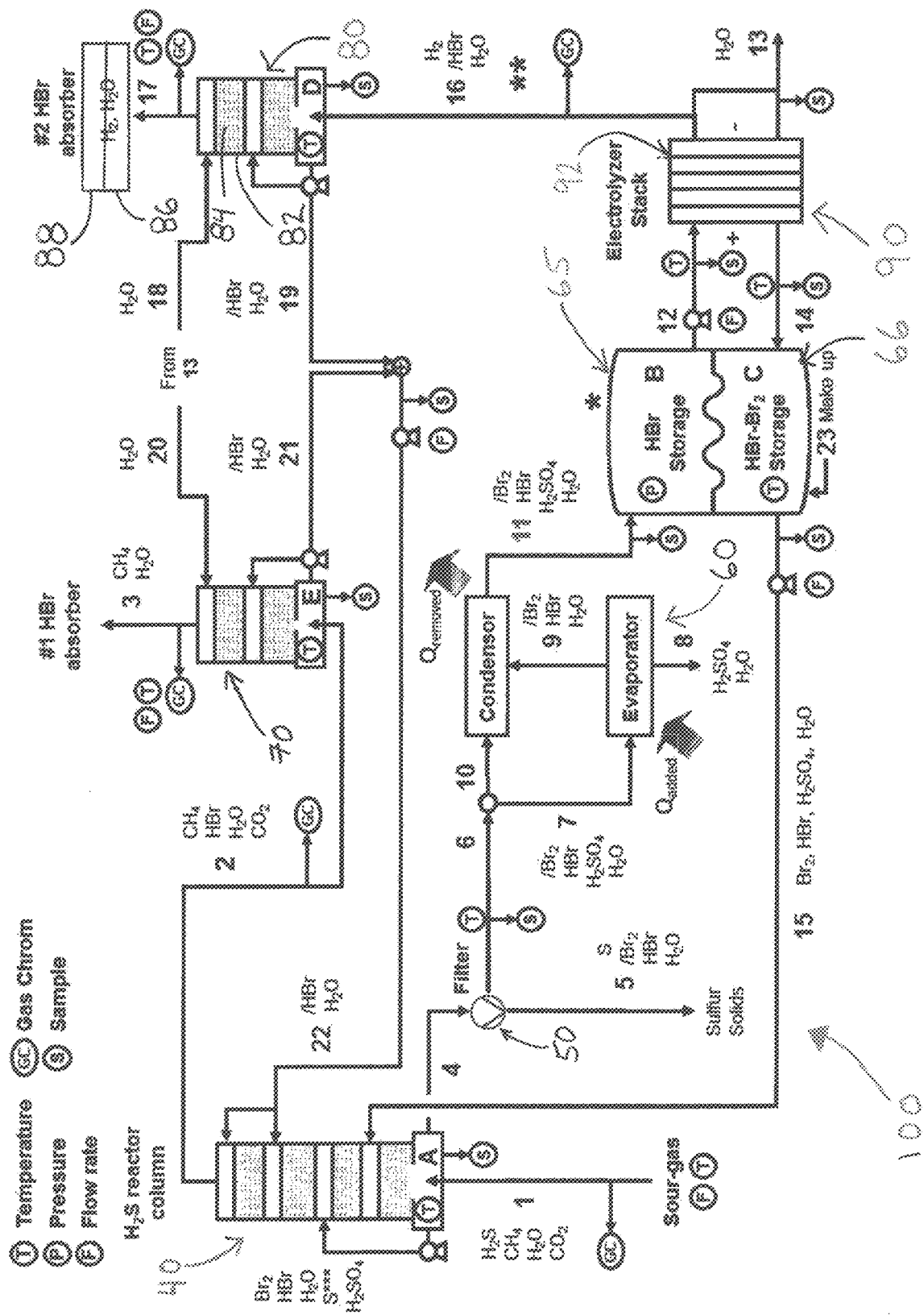
FIG. 1 is a flow diagram for a pilot scale desulphurization and hydrogen recovery system in accordance with at least one embodiment of the present invention.

Hydrogen sulfide is a noxious and poisonous environmental liability rich in hydrogen. Hydrogen is an essential chemical feedstock and a potentially carbon neutral fuel. Recovering hydrogen from hydrogen sulfide will reduce natural gas demand, greenhouse gas emissions, and the discharge of environmental pollutants.

The present disclosure presents a two-step process for removing hydrogen sulfide from sour-gas streams, and converting it into hydrogen and sulfuric acid. By recovering the hydrogen and sulfur content of hydrogen sulfide, the proposed process promises advantages of being simpler and economically favorable than established processing methods.

The chemical conversion of hydrogen sulfide ($H_2S$) into hydrogen ($H_2$) begins with its bromination in the presence of water. The bromination is an exothermic reaction analogous to combustion with oxygen ($O_2$), but since bromine ($Br_2$) is the oxidizer, the hydrogen-carrier, hydrogen bromide (HBr) is produced instead of water ($H_2O$).

The bromination of $H_2S$ in the presence of water yields sulfuric acid ($H_2SO_4$) and hydrobromic acid (HBr). The production of sulfuric acid, and hydrobromic acid releases significant amounts of heat. The reaction and its change in enthalpy at standard state) ($\Delta H°$) is shown below. [Reference 1].

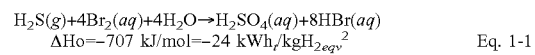

Eq. 1-1

In the reaction equations in the present disclosure, the metric "kg $H^2$ equivalent" abbreviated as "kgH$_2$eqv" is used to provide insight on the amount of heat released or electricity required to produce a kilogram of hydrogen in the given reaction.

Part of the product solution is distilled to boil off its water and hydrobromic acid content and separate them from sulfuric acid. The remaining concentrated sulfuric acid is available for sale, use, or disposal depending on the circumstances, while boiled off water and HBr is condensed. The resulting hydrobromic acid solution is sent to an electrolyzer before being mixed back into the reactor solution. Electrolysis dissociates the hydrogen-carrier HBr to produce hydrogen ($H_2$) and regenerate $Br_2$ as shown in FIG. 1-1 of U.S. Patent Application Ser. No. 61/646,576 incorporated by reference herein in its entirety.

The aqueous bromine is carried by the less concentrated aqueous HBr solution for further bromination of $H_2S$. The dissociation reaction for a concentrated aqueous HBr solution is shown below along with the Gibb's Free Energy ($\Delta G°$) which is most relevant to the amount of electricity needed to electrolyze HBr:

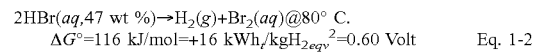

Eq. 1-2

The bromination process takes advantage of rapid and essentially irreversible reactions to convert hydrogen sulfide waste into sulfuric acid and relatively easy to dissociate hydrobromic acid. The hydrobromic acid solution can be electrolyzed at less than half the energy of water, thereby reducing the cost of producing electrolytic-grade hydrogen.

The large amount of heat released by the bromination reaction can be captured for the concentration of product sulfuric acid and to reduce the amount of electrical energy required to electrolyze HBr.

When high $Br_2$ concentrations in the solution and high $H_2S$ concentrations in the gas stream are combined with a low reactor temperature, sulfur is produced as follows:

$$H_2S(g)+Br_2(aq) \rightarrow S(s)+2HBr(aq) \Delta H° = -220 \text{ kJ/mol} = -66 \text{ kWh}_t/\text{kgH}_{2eqv}^2 \quad \text{Eq. 1-3}$$

This pathway provides an opportunity to produce sulfur if sulfuric acid and hydrogen are not desired. The sulfur is filtered from the hydrobromic acid solution, washed, and dried.

In accordance with the present disclosure, a bromine rich solution of bromine in dilute hydrobromic and sulfuric acid oxidizes $H_2S$ to sulfuric acid and more concentrated hydrobromic acid in an exothermic reaction that releases 24 kWh of heat per kilogram of hydrogen ($kWh_t/kgH_2$). The spent bromine solution is pumped to an electrolysis cell, where the HBr is electrolyzed to produce hydrogen, and regenerate bromine reagent—which is recycled back to the process for further $H_2S$ treatment. FIG. 1-2 of U.S. Patent Application Ser. No. 61/646,576 incorporated by reference herein in its entirety shows a simple schematic of the process.

The $H_2S$ bromination reactor can be an open spray, packed or solution filled absorption column operated at elevated pressures to reduce equipment size and increase throughput. Methane and other higher-carbon hydrocarbons in sour gas pass through the bromination reactor unreacted, and exit in a sweetened sulfur-free state. The sulfuric acid product is removed from the reactor solution by concentrating a fraction of the spent scrubbing solution in a packed column. This concentration step removes any appreciable bromine and hydrobromic acid content from the sulfuric acid.

In the present process, the hydrogen sulfide contaminant is removed from a hydrocarbon rich sour-gas, and 8 kilograms of hydrogen and 98 kilograms of sulfuric acid are produced for every 32 kilograms of hydrogen sulfide treated.

The electrolyzer can be a standard Proton Exchange Membrane (PEM) cell as used presently by the chlor-alkali industry, or a more custom matrix or diaphragm cell. The former has the benefit of lower overvoltages, while the latter may be operated at higher temperatures. The difference between these two types of cells is elaborated and illustrated below for future reference.

A solid polymer electrolyte cell uses a Proton Exchange Membrane (PEM) that is sandwiched between the cathode and anode. NAFION® is a common PEM material made up of sulfonated TEFLON® which selectively allows positive ions to cross it, while inhibiting anion transport. In actual practice these membranes are not 100% selective, and some anions can migrate to the cathode via diffusion. NAFION® is limited to a maximum operating temperature of 150° C., however newer membranes can withstand higher temperatures exceeding 190° C. The cross section of a typical solid polymer electrolyte cell is shown in FIG. 1-3 of U.S. Patent Application Ser. No. 61/646,576 incorporated by reference herein in its entirety.

During electrolysis, hydrobromic acid passes along the anode side where protons are pulled out and passed through the membrane to combine with electrons on the cathode side to form hydrogen. Hydrogen gas is evolved, while a less concentrated (dilute) hydrobromic acid and more concentrated (rich) bromine solution exits the anode side. Bromine remains in solution as it is highly soluble in hydrobromic acid.

PEM cell electrodes are permanently bonded to the membrane forming a Membrane Electrode Assembly (MEA). This reduces the internal resistive losses of the cell to the thickness of the membrane, prevents non-conductive gas phases from causing high current density hot spots, and facilitates the embedding of high surface area catalysts into the electrodes. Despite these advantages, cation exchange membranes are penalized by membrane resistance and water transport limitations at high acid concentrations due to membrane dehydration.

Another cell configuration is the matrix or diaphragm cell, which has a spatially separated anode and cathode with a physical barrier in between to prevent the mixing of gaseous and aqueous products. These cells benefit from the high conductivity of hydrobromic acid solutions, may utilize laminar flow to further reduce mixing between anode and cathode compartments, do not suffer from water transport limitations, and can operate at higher temperatures. They can suffer from high internal resistance due to the formation of gaseous hydrogen and the requirement for spatially separated electrodes. The cross section of a diaphragm cell is shown in FIG. 1.4 of U.S. Patent Application Ser. No. 61/646,576 incorporated by reference herein in its entirety.

In a diaphragm cell, hydrobromic acid is passed along both sides of the diaphragm and bromide ions migrate to the anode side where they donate an electron and form bromine, while protons migrate to the cathode side where they accept an electron and form hydrogen. Hydrogen gas evolves up and out of the cell, while a dilute hydrobromic acid and bromine-rich solution exits the bottom of the cell in a counter-current configuration. The spent hydrobromic acid and bromine-rich solution could also exit the top of the cell if a co-current configuration is used. These cells can operate without a diaphragm separator to increase conductivity, thereby decreasing resistance, but this often results in a lower current efficiency due to recombination of hydrogen and bromine.

The process for removing $H_2S$ in accordance with the present disclosure using an aqueous bromine solution, and its theoretical performance may be evaluated using reaction equilibrium calculations, and process flow analysis with mass and energy balances.

The two reactions of particular interest are:

$$H_2S(g)+4Br_2(aq, 1 \text{ m})+4H_2O(l)H_2SO_4(aq, 1 \text{ m})+8HBr (aq, 1 \text{ m}) \Delta H° = -707 \text{ kJ/mol} = -24 \text{ kWh}_t/\text{kgH}_{2eqv}^2 \quad \text{Eq. 3-1}$$

$$2HBr(aq, 1 \text{ m})H_2(g)+Br_2(aq, 1 \text{ m}) \Delta G° = 212 \text{ kJ/mol} = -29 \text{ kWh}_e/\text{kgH}_{2eqv}^2 = 1.1 \text{ Volt} \quad \text{Eq. 3-2}$$

The reactions do not occur in their standard states as we expect to use bromine solutions less than 1 molal and hydrobromic acid and sulfuric acid solutions greater than 1 molal. Table 3-1 shows molality, molarity, mole fraction, and weight percent for some solutions.

Table 3-2 shows concentrations expected in an operational reactor system which prefers medium concentration of hydrobromic and sulfuric acids to reduce bromine evaporation and facilitate decomposition and concentration respectively.

The reversible cell voltage for HBr electrolysis is calculated from the Nernst equation:

$$E_{decomposition} = \Delta G/nF \quad \text{Eq. 3-3}$$

For our example reaction (2HBr→Br$_2$+H$_2$) the Gibbs energy is related to concentrations, pressure, and temperature as follows:

$$\Delta G_{T2,P0,Ni} = \Delta G_{T0,P0,N1m} + (C_{P,Br2} + C_{P,H2} - 2C_{P,HBr})(T_2 - T_0)1n(T_2/T_0) + RT(1n(a_{Br2}) + 1n(p_{H2}) - 21n(a_{HBr}))$$  Eq. 3-4

As the equation suggests, an increase in bromine activity or hydrogen pressure increases the reversible cell voltage, while an increase in hydrobromic acid (proton and bromide ions) activity or temperature decreases the reversible voltage.

The most important parameters affecting the HBr reversible voltage are the HBr concentration and temperature with the bromine activity and hydrogen pressure having a smaller overall effect at conditions of interest.

FIG. 3-1 of U.S. Patent Application Ser. No. 61/646,576 incorporated by reference herein in its entirety shows the theoretical decomposition voltage for hydrobromic acid at different temperatures and concentrations. For comparison, experimental results at 25° C. are included. These results are higher than the theoretical decomposition voltage due to overvoltages at the hydrogen cathode and internal cell resistance, but are still quite close to the minimum reversible voltage.

Water electrolysis requires at least 1.23 Volts and in actual practice more than 1.8 Volts as discussed above. Thus electrolyzing HBr at elevated temperatures can further reduce the electricity required to produce hydrogen to 60-80% of water electrolysis.

Equilibrium calculations were undertaken using HSC CHEMISTRY® software to identify what species are thermodynamically stable under which conditions, and to evaluate the conditions in which solid sulfur and/or sulfuric acid are preferred. An additional result is the identification of species to be sought out in the reaction mixture.

The method relies on minimizing the Gibbs free energy of solution based on the amount of initial species present and the different forms each species can take in each other's presence. Table 3-3 shows the species considered in the thermodynamic calculations.

Many of the above species are not expected to occur in any significant quantity. Including them in some initial calculations confirmed their insignificance and allowed their removal in follow on analyses. The principal species of concern are retained and shown bolded in Table 3-3. The non-bolded species are not considered in further calculations because combined they are less than $10^{-5}$ percent of the species present.

These equilibrium calculations do not conclusively identify what species are actually formed, but the calculations do show what is thermodynamically favored. Activation energies required for each step of a reaction mechanism can prevent the formation of the most stable and lowest energy species, but these calculations provide insight on what products are favored if given unlimited time for equilibrium to establish.

Unless noted otherwise, all calculations are done at a pressure of 1 bar with 0.1 kmol of nitrogen present. The nitrogen, being inert, maintains a gas phase and allows reasonable gas phase equilibrium products to be considered. All other species identified in Table 3-3 are given an initial quantity of $10^{-9}$ moles to facilitate the calculation.

Thermodynamic equilibrium results are shown in FIG. 3-2 of U.S. Patent Application Ser. No. 61/646,576 incorporated by reference herein in its entirety for a model system at 25° C. as the quantity of bromine is increased. The solution starts with 1 kmol of H$_2$S gas, 55 kmol of H$_2$O, and 5 kmol of aqueous hydrobromic acid. This corresponds to a 5 molal solution of HBr in water. The quantity of bromine is then increased from zero to 6 kmol, corresponding to a maximum molality of 6 molal in water.

The results match what the preliminary research suggests. When no bromine is present some H$_2$S dissolves into the water forming an aqueous form while the majority remains as a gas above solution. To a very small extent H+ and HS− are formed from H$_2$S. Hydrobromic acid alone does not affect H$_2$S, and is present as HBr, H+ and Br− in solution. As bromine is added it reacts with H$_2$S to form elemental sulfur first, raising sulfur's oxidation state from −2 to zero. Upon one equivalent of bromine being added, all the H$_2$S is thermodynamically stable as elemental sulfur.

As additional bromine is added, the sulfur is oxidized further to sulfate with two principal forms H$_2$SO$_{4-}$ and SO$_4^{-2}$ becoming most prevalent. This represents a change in sulfur's oxidation state from zero to +6. Upon reaching four equivalents of bromine to H$_2$S, all the sulfur exists as sulfate. Adding more bromine above four equivalents does not change sulfur's state, but as expected the bromine concentration increases, and the bromide ions form a complex with Br$_2$ resulting in Br$_{3-}$ and Br$_{5-}$ ions in solution. Gaseous bromine also starts to occur as expected in this relatively concentrated bromine solution.

FIG. 3-3 of U.S. Patent Application Ser. No. 61/646,576 incorporated by reference herein in its entirety shows the next most important species in this equilibrium calculation. HS− anion decreases with bromine addition. Between one and four bromine equivalents H$_2$SO$_3$ and H$_2$S$_2$O$_3$ rise, but then fall in the presence of excess bromine. All together these species can be eliminated from consideration due to the small amounts expected.

The above thermodynamic snapshot was for room temperature when bromine was the varied reagent. Bromine was also at much higher concentrations than would be found in the expected process design. This resulted in a small but significant fraction of bromine being in gaseous phase when all sulfur was in the form of sulfate.

Actual reactor operation has bromine in excess to encourage complete removal and conversion of H$_2$S from any passing sour-gas stream. Under such conditions sulfuric acid formation is preferred as pure sulfur is not favored thermodynamically when bromine is in excess. It is conjectured that to produce sulfur the reaction will have to be performed in the gas phase with a stoichiometric amount of bromine and H$_2$S.

A range of conditions examined did not show preference for an aqueous phase reaction occurring between H$_2$S and bromine to produce sulfur when bromine was in excess. In all cases the bromine sought to oxidize the sulfur to sulfate. However, if the reaction is performed in the presence of sulfuric acid it is possible to convert the H$_2$S to sulfur by oxidizing it with sulfuric acid to produce water and sulfur as follows:

$$3H_2S(g) + H_2SO_4(aq) \rightarrow H_2O(l) + 4S(s)$$  Eq. 3-5

With the bromination reaction serving to regenerate sulfuric acid:

$$H_2S(g) + 4H_2O(l) + 4Br_2(aq) \rightarrow H_2SO_4(aq) + 8HBr(aq)$$  Eq. 3-6

Such that the net reaction is:

$$4H_2S(g) + 4Br_2(aq) \rightarrow 4S(s) + 8HBr(aq)$$  Eq. 3-7

FIG. 3-4 of U.S. Patent Application Ser. No. 61/646,576 incorporated by reference herein in its entirety shows a calculation performed with varied H$_2$S in a 70 wt % H$_2$SO$_4$, 15 wt % HBr, and 2 wt % bromine solution. Equilibrium favors the production of HBr and sulfuric acid when in excess of 4 equivalents of bromine per $H_2S$ is present. As the fraction of $H_2S$ increases to be more than one fourth of the bromine present, sulfur formation is favored at the expense of sulfate.

Three additional equilibrium calculations are shown below for solutions with different sulfuric acid concentrations, and $H_2S$ to bromine ratios. All solutions contain 1 kmol of $Br_2$, 11.35 kmol of HBr, 44.18 kmol of $H_2O$, start with no $H_2SO_4$, and end with 50 kmol of $H_2SO_4$. This corresponds to an initial 8.5 wt % $Br_2$, 49.0 wt % HBr and 42.5 wt % water solution that ends as a 2.4 wt % $Br_2$, 13.5 wt % HBr, 11.7 wt % water, and 72.4 wt % $H_2SO_4$ solution.

FIG. 3-5 of U.S. Patent Application Ser. No. 61/646,576 incorporated by reference herein in its entirety shows when $H_2S$ and bromine are in a 1:4 ratio which corresponds to the stoichiometric requirements for the formation of sulfuric acid. Under these conditions, the lowest energy state of sulfur is as sulfuric acid.

FIG. 3-6 of U.S. Patent Application Ser. No. 61/646,576 incorporated by reference herein in its entirety shows when $H_2S$ and bromine are in a 1:3 ratio. The thermodynamics predict that some sulfur will exist in elemental form, and none as $H_2S$.

FIG. 3-7 of U.S. Patent Application Ser. No. 61/646,576 incorporated by reference herein in its entirety shows when $H_2S$ and bromine are in a 1:5 ratio. The thermodynamics predict that all sulfur will exist as sulfuric acid, albeit different forms of the acid in water.

The equilibrium results suggest that while sulfuric acid is the preferred product of the bromination reaction in the presence of water, it may be possible to produce elemental sulfur by adequately controlling the reaction conditions. A staged reactor could react bromine with one fourth the $H_2S$ first to produce sulfuric acid, then react this sulfuric acid with the remaining three-fourths $H_2S$ to produce sulfur which may be filtered out prior to the solution going to an electrolyzer for bromine regeneration.

Several runs are performed at conditions closer to the anticipated quasi-steady reactor conditions with a 1 wt % bromine, 15 wt % hydrobromic acid, and 15 wt % sulfuric acid solution in a 1 to 4.5 and 2.2 to 1 $H_2S$ to bromine ratio from 25° C. to 300° C. The reactor solution is selected to maintain a relatively low HBr and $Br_2$ vapor pressure to reduce their losses. The 1 to 4.5 (1:4.5) and 2.2 to 1 (2.2:1) $H_2S$ to bromine ratios are selected to allow comparison between the two extremes of expected reaction products.

The 1:4.5 $H_2S$ to bromine ratio is shown in FIG. 3-8 of U.S. Patent Application Ser. No. 61/646,576 incorporated by reference herein in its entirety. As the temperature increases, the species shift to gaseous form. At high temperatures, sulfur is present as sulfate, and bromine is gaseous HBr and $Br_2$ in steam. The increasing volatility of bromine is evident from its transition at low temperature from the $Br{a_3}_-$ ion to $Br_2$ gas.

FIG. 3-9 of U.S. Patent Application Ser. No. 61/646,576 incorporated by reference herein in its entirety shows the 2.2:1 $H_2S$ to bromine ratio mix. As the temperature increases the species transition to gaseous form again, but with $H_2S$ in excess, it becomes prevalent in the calculations above 100° C., where bromine is found in HBr gas along with steam.

The generation of bromine and $H_2S$ gas respectively in the two cases above at high temperature suggest a need to examine higher pressures. Since most natural gas processing occurs at high pressure the two systems were considered again at 1000 bar over an increased temperature range of 25° C. to 600° C. The 2.2:1 $H_2S$ to bromine ratio is shown in FIG. 3-10 of U.S. Patent Application Ser. No. 61/646,576 incorporated by reference herein in its entirety, with respect to temperature at 1000 bar. The components remain in liquid phase as expected and all sulfur is in the form of sulfate.

FIG. 3-11 of U.S. Patent Application Ser. No. 61/646,576 incorporated by reference herein in its entirety shows the 2.2:1 $H_2S$ to bromine ratio for 1000 bar pressure at the same temperature range. Here $H_2S$ is converted to sulfur and then $H_2S$ at higher temperatures.

Higher temperatures improve the kinetics and allow faster equilibrium. Raising pressure is necessary to reduce the equipment size and maintain the species in aqueous solution. High pressure also allows the flashing of reaction products to separate bromine and HBr from the sulfuric acid solution. From the thermodynamic equilibrium analyses it appears a reactor could operate at elevated pressure and temperature to make use of the oxidation of $H_2S$ by bromine and water to produce sulfuric acid.

Returning to the first equilibrium calculation, FIG. 3-12 of U.S. Patent Application Ser. No. 61/646,576 incorporated by reference herein in its entirety shows the expected products from a reactor solution with variable $Br_2$ content. The solution starts with no bromine in 18.4 wt % hydrobromic acid and 20.4 wt % sulfuric acid, and ends with a 2.4 wt % bromine concentration in 17.9 wt % hydrobromic acid and 19.9 wt % sulfuric acid.

FIG. 3-13 of U.S. Patent Application Ser. No. 61/646,576 incorporated by reference herein in its entirety shows the preferred products between bromine, water and methane as bromine is increased. In the case of bromine and methane in the presence of water, carbon is preferred up until a stoichiometric ratio of 2:1 bromine to carbon occurs. At higher ratios of bromine to carbon the most stable carbon compound is $CO_2$.

While these are the favored species equilibrium will approach, in practice they do not occur in significant quantities until temperatures exceeding 600° C. are reached as documented in the literature. [Reference 77]. Because there is no viable mechanism for methane and other hydrocarbons to react with bromine, they are expected to pass through a bromine scrubber unaffected. Additional evidence supporting this is the relative low solubility of methane and higher hydrocarbons in aqueous solutions as discussed below.

Sulfuric acid is favored under all conditions where water is present and bromine is in excess of 4 times the $H_2S$ concentration. The most $H_2S$ is removed when the reactor is operated bromine rich, but the reactor must not be too rich or significant gaseous bromine emissions may occur that would require additional steps in a final water scrubber.

If very large and dilute sour ($H_2S$) gas volumes are handled, operating bromine lean would reduce the bromine partial pressure which would decrease the bromine that leaves the reactor with the sweetened gas. Doing this would result in some $H_2S$ remaining in the mostly-sweetened gas stream.

There are many engineering decisions that must be made on a case by case basis depending on the specific gas stream. In the above case, the decision would be based on a trade-off between the amount of $H_2S$ remaining in the gas stream, and the gas residence time and recirculation rates of the reactor and final scrubber.

Equilibrium calculations suggests sulfur is the preferred product when:

sulfuric acid is allowed to oxidize $H_2S$ in the absence of bromine, bromine is provided in stoichiometric quantities in the absence of sulfuric acid, or the reaction occurs in the gas phase at elevated temperature It appears $H_2S$ will be oxidized in the presence of bromine to sulfuric acid, but that in the presence of concentrated sulfuric acid a solid sulfur state can form. This agrees with the oxidation state of reactants and their electro-negativities.

Several reaction mechanisms are proposed for the anticipated reactions. Initially it was thought that kinetics data could be obtained for these mechanisms, but early in the experiments it was found that the reaction happened very fast and was essentially irreversible at the conditions considered.

Sulfuric acid is the predominant product of hydrogen sulfide bromination in water:

$$H_2S + 4Br_2 + 4H_2O \rightarrow 8HBr + H^2SO^4 \qquad \text{Eq. 3-8}$$

The following outlines a potential pathway to produce sulfuric acid:

$$Br_2 + H_2O \rightarrow HOBr_2^- + H^+ \rightarrow HBrO + H^+ + Br^- \rightarrow BrO^- + 2H^+ + Br^- \qquad \text{Eq. 3-9}$$

$$HBrO + HS^- \rightarrow HSOH + Br^- \rightarrow HSO^- + H^+ + Br^- \qquad \text{Eq. 3-10}$$

$$HBrO + HSO^- HSO_2H + Br^- \rightarrow HSO_2^- + H^+ + Br^- \qquad \text{Eq. 3-11}$$

$$HBrO + HSO_2^- HSO_3H + Br^- \rightarrow HSO_3^- + H^+ + Br^- \qquad \text{Eq. 3-12}$$

$$HBrO + HSO_3^- H_2SO_4 \rightarrow Br^- \qquad \text{Eq. 3-13}$$

$$H_2SO_4 \rightarrow H^+ + HSO_4^- \rightarrow 2H^+ + SO_4^{-2} \qquad \text{Eq. 3-14}$$

Sulfur is a secondary product of the bromination reactions:

$$H_2S + Br_2 \rightarrow 2HBr + S \qquad \text{Eq. 3-15}$$

In order for this reaction to proceed multiple steps must occur. As an aqueous phase reaction, $H_2S$ must diffuse into and be absorbed by the $Br_2/HBr/H_2O/H_2SO_4$ solution, then it must react to form sulfur. In aqueous solution the following occurs:

$$H_2S \rightarrow HS^- + H^+ \text{ alt. } H_2S + H_2O \rightarrow H_3O^+ + HS^- \qquad \text{Eq. 3-16}$$

$$HBr \rightarrow H^+ + Br^- \text{ alt. } HBr + H_2O \rightarrow H_3O^+ + Br^- \qquad \text{Eq. 3-17}$$

$$Br^- + Br_2 \rightarrow Br_3^- \text{ alt } HBr + \frac{1}{2}Br_2 + H_2O \rightarrow H_3O^+ + Br_3^- \qquad \text{Eq. 3-18}$$

$$Br_2 + H_2O \rightarrow HBrO + HBr \rightarrow HBrO + H^+ + Br^- \rightarrow BrO^- + 2H^+ + Br^- \qquad \text{Eq. 3-19}$$

These would then be followed by bromine oxidation:

$$H_2S + BrO^- \rightarrow HS + Br^- + OH^- \rightarrow H_2O + Br^- + S \qquad \text{Eq. 3-20}$$

Previous thermodynamic studies and experiments suggest that $H_2S$ is not converted to elemental sulfur in aqueous solution with bromine, or in the presence of sulfuric acid. It is possible that it is produced, but then consumed in other reaction pathways that lead to sulfuric acid. A potential gas phase reaction pathway follows:

$$H_2S + Br_2 \rightarrow H_2SBr_2 \rightarrow HSBr + HBr \qquad \text{Eq. 3-21}$$

$$HSBr + HBr \rightarrow 2HBr + S \qquad \text{Eq. 3-22}$$

Sulfur may form from hydrogen sulfide reacting with sulfuric acid as it is a thermodynamically stable product from mixtures of these two species. In the absence of bromine, concentrated sulfuric acid is a strong enough acid to oxidize $H_2S$ to sulfur.

$$H_2S(g) H_2SO_4(aq) \rightarrow H_2SO_3(aq) + S(s) + H_2O \qquad \text{Eq. 3-23}$$

Carbon bromide formation is avoided by maintaining an excess of water and keeping the reactor at a low temperature (<400 Celsius). Doing so prevents the following reactions from occurring:

$$CH_4 + Br_2 \rightarrow CH_3Br + HBr \qquad \text{Eq. 3-24}$$

$$CH_3Br + Br_2 \rightarrow CH_2Br_2 + HBr \qquad \text{Eq. 3-25}$$

$$CH_2Br_2 + Br_2 \rightarrow CHBr_3 + HBr \qquad \text{Eq. 3-26}$$

$$CH_3Br + Br_2 \rightarrow CBr_4 + HBr \qquad \text{Eq. 3-27}$$

Carbon and carbon dioxide formation is avoided by keeping the reactor temperature low (<500° C.). The following reactions are thermodynamically very favorable, but are not observed at temperatures less than 500 Celsius as confirmed by previous work [Reference 78]:

$$CH_4 + 2Br_2 \rightarrow 4HBr + C \qquad \text{Eq. 3-28}$$

$$CH_4 + 4Br_2 + 2H_2O \rightarrow 8HBr + CO_2 \qquad \text{Eq. 3-29}$$

If any carbon bromides do form they will be hydrolyzed in a very favorable reaction with water to form alcohols as follows:

$$CH_3Br + H_2O \rightarrow CH_3OH + HBr \qquad \text{Eq. 3-30}$$

Carbon, $CH_3Br$, $CH_2Br_2$, $CHBr_3$, $CBr_4$, $C_2H_5Br$, $C_2H_3Br$, as well as $CH_3OH$ and other alcohols were sought out in the reaction product mixture to determine the conversion of hydrocarbons through bromination into undesirable products. None of these hydrocarbon products from reaction between bromine and methane were found in the reactor solutions. These reactions can occur as demonstrated by other research, but do not occur to any significance at the low temperatures evaluated for the $H_2S$ bromination process. [Reference 79].

The partial pressure of each species is considered in the system mass balance and process flow. The partial pressure of hydrogen bromide and water at a wide range of temperatures and concentrations of interest are presented. FIG. 3-14 of U.S. Patent Application Ser. No. 61/646,576 incorporated by reference herein in its entirety shows the partial pressure of HBr in different concentrations of HBr at 300° C., 400° C., 500° C. and 600° C.

The HBr partial pressure is very small at low HBr concentrations and modest temperatures, a result of the solubility of HBr in water. This allows the near elimination of fugitive HBr vapors by contacting exhaust gases in a water scrubber with low HBr content. A similar situation occurs for bromine which is very soluble in HBr solutions. [Reference 80].

FIG. 3-15 of U.S. Patent Application Ser. No. 61/646,576 incorporated by reference herein in its entirety shows the partial pressure of HBr and $H_2O$ in different concentrations of sulfuric and hydrobromic acids.

As the sulfuric or hydrobromic acid concentration increases the water vapor pressure decreases and HBr vapor pressure increases. At high concentrations, water stays with the sulfuric acid, resulting in HBr preferentially being boiled off or evaporated. This property is why sulfuric acid is used as a dehydrating agent.

FIG. 3-16 of U.S. Patent Application Ser. No. 61/646,576 incorporated by reference herein in its entirety shows the partial pressure of HBr and $H_2O$ in 20 wt % hydrobromic acid at different concentrations of sulfuric acid and temperature.

The partial pressures of HBr remain small at low temperatures and sulfuric acid concentration. The vapor pressure of bromine is of interest due to its presence in the reactor. Bromine is only a little soluble in pure water, but becomes very soluble in hydrobromic acid due to formation of $Br_3^-$ anions in solution. This causes bromine's vapor pressure to be very low when in aqueous solution with hydrobromic acid, and prevents it from being carried out of the reactor along with unreacted gases.

Sulfuric acid will need to be removed from the reactor to prevent its concentration from increasing to the point that excessive HBr is boiled off. The method for doing this is to take a slip stream of reactor solution and add heat to boil off its HBr and water content in a controlled manner that allows their condensation and redirection to the electrolyzer before being put back in the reactor.

FIG. 3-17 of U.S. Patent Application Ser. No. 61/646,576 incorporated by reference herein in its entirety shows the energy to concentrate a solution of sulfuric acid per kilogram of $H_2$ resulting from its formation. Much of the 24 kWh of heat released for each kilogram of $H_2$ produced is available to concentrate the acid, but some additional heat will be required to achieve a pure sulfuric acid product.

It is important to concentrate the sulfuric acid because doing so removes its bromide content and makes it easier to transport to market. If the acid is to be disposed or used onsite it need only be concentrated to 70 wt % sulfuric acid since this is acceptable for the production of fertilizers, tanning of leather, and pickling of steel. [Reference 81].

FIG. 3-18 of U.S. Patent Application Ser. No. 61/646,576 incorporated by reference herein in its entirety shows the bromide content of sulfuric acid versus its concentration. Only a few ppm of bromine are present in 93 wt % sulfuric acid, but 70 wt % sulfuric acid has approximately 0.1 wt % hydrobromic acid. This corresponds to one kg of bromine per tonne of sulfuric acid.

Choosing the proper temperature and concentration of sulfuric and hydrobromic acid in the reactor leads to a solution that does not boil away, but is still of high enough concentration to minimize the heat required to concentrate sulfuric acid and electricity required to decompose hydrobromic acid. An HBr concentration of 10 wt % in 30 wt % sulfuric acid at 300° C. is preferred.

The following solubility charts are for pure water and are useful in understanding the tendency of species to dissolve and become available for reaction. [Reference 82]. FIG. 3-19 and FIG. 3-20 of U.S. Patent Application Ser. No. 61/646,576 incorporated by reference herein in its entirety show the solubility of $H_2S$ and methane ($CH_4$) in water.

$H_2S$ is 200 times more soluble on a mass basis than methane, which partially explains why aqueous bromine preferentially reacts with $H_2S$ and not methane. When $H_2S$ dissolves in water, it becomes available for reaction. This was shown in the tube worm and methane clathrate example described in section 1.4.4.

FIG. 3-21 and FIG. 3-22 of U.S. Patent Application Ser. No. 61/646,576 incorporated by reference herein in its entirety show the solubility of ethane ($C_2H_6$) and ethylene ($C_2H_4$), respectively. They are more soluble on a mass basis than methane, but are also heavier. Ethylene is much more soluble than ethane or methane, and it was found to react with bromine. Fortunately it is not a very large component of sour-gas.

Higher hydro-carbon components occur in small quantities in most sour-gases and are difficult to brominate at low temperatures, but are more reactive than methane, in part due to their increased solubility. Tests to be described later have confirmed these higher hydrocarbons do not react with aqueous bromine at the conditions considered.

An implementation of the process for cleaning sour-gas stream in accordance with the present disclosure is described below. More in particular, the following describes the process flow, the specific equipment required, and the constituents of each stream.

FIG. 3-23 of U.S. Patent Application Ser. No. 61/646,576 incorporated by reference herein in its entirety is a simplified diagram for the flows within the system. A storage tank for product HBr and reactant $Br_2$ is included, as well as an $H_2$ scrubber, cooler and dryer to produce $H_2$ of marketable quality. If the $H_2$ is to be mixed into the sweetened natural gas these two pieces of equipment may be eliminated by passing the hydrogen stream directly through the off-gas HBr absorber column.

The following describes each of the major pieces of equipment highlighted above. Adequate plumbing, pumps, sensors, and passive safety features will also have to be provided in acid compatible materials.

Reactor—The scrubbing column can be Polyvinyl Chloride (PVC) with a Polytetrafluoroethylene (PTFE) liner or many other $Br_2$ and $H_2S$ compatible materials. The geometry of this column should be large enough to keep the gas velocity low enough to not entrain the scrubbing solution. There should be enough scrubbing solution sprayed in small enough drops to thoroughly contact the $H_2S$ with bromine solution. Packing should be avoided to minimize the surfaces in which sulfur may contact and deposit.

The column should be a counter current absorption tower so the incoming sour-gas enters at the bottom and exits at the top, while the scrubbing solution enters at the top and flows down through multiple trays. The purpose of this reactor is to adequately mix the $Br_2$ rich scrubbing solution with the sour-gas.

It is possible to bubble the gas stream through a column of liquid solution by breaking the gas into a collection of small bubbles. This is usually not the best method to encourage contact due to high gas stream pressure losses, but can result in a simpler reactor at small implementations.

HBr Absorber Column—Some $H_2O$ and HBr will evaporate into the outgoing sweetened gas stream which will then pass through a water absorbing column to remove HBr and any unreacted and soluble $H_2S$. As with the reactor, the column must be large enough to maintain low gas velocities, and the water must be circulated at a high enough rate to ensure intimate contact between gas and solution. Most of this water is recirculated, but a fraction is taken off for delivery to the HBr storage tank. Additional water is introduced to this scrubber from the $H_2$ scrubber and dryer.

Distillation column—The reactor product HBr stream is split with a smaller stream going to a distillation column to remove its sulfuric acid content. In the above implementation 6 wt % of the stream goes to the distillation column where heat is added to boil off the HBr and $H_2O$ content. The remaining liquid is 92 wt % concentrated sulfuric acid with a very small (<1 ppm) amount of HBr. The majority of HBr and $H_2O$ vapors boiled off are condensed and mixed with the other 94% of the reactor product HBr stream and sent to the storage or surge tank. In an alternate set up this HBr and $H_2O$ stream can be sent directly to the electrolyzer where its higher temperature and HBr concentration reduce the required electrolysis voltage.

Because the reactor solution is at pressure and an elevated temperature, the heat required for distillation can be reduced by flashing the solution to boil off some of the HBr and $H_2O$ content. Some of the heat required may also come from the condensation of these vapors such that very little heat input is required to concentrate the sulfuric acid.

Br$_2$/HBr Storage Tank—The storage tank is made of Polyvinylidene Fluoride (PVDF) or another bromine compatible material. It has a diaphragm in it which separates the top from the bottom, allowing two different solutions to be stored. The top section contains the reactor product HBr solution, while the bottom solution has the denser reactor reactant Br$_2$/HBr solution that comes out of the electrolyzer.

The storage tank may be unnecessary if the system does not do energy storage. A system which continuously removes H$_2$S without any energy storage may integrate the electrolyzer (to be discussed) with the reactor column and store all solution required within the column.

HBr Electrolyzer Stack—This is where the HBr is decomposed to H$_2$ and Br$_2$ through the addition of electrical energy. The stack can use a Proton Exchange Membrane (PEM) or have simpler graphite or titanium electrodes. A stack is made up of many cells aligned next to each other with each cell discharging at approximately 1.2 Volts.

Operating at a higher current density decreases the efficiency, but also decreases the electrode area and overall stack size and cost, whereas decreasing the current density allows a more efficient utilization of electricity.

Rectifier—This converts the AC current from the grid or a generator to the DC current required by the electrolyzer. Alternatively this equipment may be substituted for a simpler power conditioning package if DC power is available from, for instance, use of the product hydrogen in a fuel cell, or a directly coupled wind turbine or solar panel.

Hydrogen Scrubber—This washes the product H$_2$ with water to remove any HBr vapors that may cross the PEM with protons, or evolve with H$_2$ from solution during electrolysis. This may be integrated with the HBr absorber column if the H$_2$ is just being mixed with the sweetened natural gas.

Hydrogen Cooler and Dryer—This removes moisture from the H$_2$ which puts it in a form that can be stored and sold. Additional equipment associated with this device to compress and store the H$_2$ is also required. Water from this process goes to both the HBr absorber and the H$_2$ scrubber.

The process flow above serves as the basis for performing a mass balance to estimate what each solution contains. Assumptions on the overall reaction yields, and known relations for the partial pressure of H$_2$O, HBr, Br$_2$ and H$_2$SO$_4$ over their solutions are used to calculate the makeup of each gas and liquid stream identified in FIG. 3-23 of U.S. Patent Application Ser. No. 61/646,576 incorporated by reference herein in its entirety. The mass balance allows equipment to be sized, and the pumping requirements estimated for the economic calculations presented below.

The molar flow rates for an example 100 mole/min gas stream containing 96 vol % methane and 4 vol % H$_2$S are shown in FIG. 3-24 of U.S. Patent Application Ser. No. 61/646,576 incorporated by reference herein in its entirety.

The reactor is maintained at 10 atm, while the majority of other equipment is held at 1.5 atm to allow a reduction in equipment size. The maximum temperature of 180 Celsius occurs in the sulfuric acid distillation column. The amount of HBr leaving the hydrogen scrubber is negligible, but some does leave with the concentrated sulfuric acid. The volumetric and mass flow rates for the different streams are shown in FIG. 3-25 of U.S. Patent Application Ser. No. 61/646,576 incorporated by reference herein in its entirety.

FIG. 3-26 of U.S. Patent Application Ser. No. 61/646,576 incorporated by reference herein in its entirety shows the solution and gas wt % concentrations, the partial pressure of HBr and water, and a written description of the streams shown in FIG. 3-23 of U.S. Patent Application Ser. No. 61/646,576 also incorporated by reference herein in its entirety.

The process of the present disclosure centers around understanding the bromination of hydrogen sulfide, as is discussed in detail below. In particular, the present disclosure presents:

Confirmation of the removal of H$_2$S in excess of 99.9% with aqueous Br$_2$ solution;

Determination of reaction rates;

Evaluation of the effect of temperature and solution concentration;

Identification of the form of sulfur product;

Confirmation of the efficacy of water scrubber to capture bromine/HBr vapors; and Close bromine and sulfur mass balances The methods used to analyze the gas, liquid and solid phases of reactants and products are described in greater detail below.

Gas Chromatography (GC) is used to analyze incoming-untreated and outgoing-treated gas streams. The GC's Thermal Conductivity Detector (TCD) measures changes in thermal conductivity of a sample gas in comparison to a reference gas. The sample gas is carried through a long tube filled with a packing material by helium, which also serves as the reference gas. The different gases in the sample adsorb to the packing material with different affinity, which over the 20+ foot length of piping separates the different gases from each other. When the sample is carried across the TCD a different thermal conductivity compared to the reference helium gas thermal conductivity is recorded. This difference shows up as a quantifiable peak area which is used to measure the concentration of a given gas species in the original sample.

A combination of HayeSep Q and HayeSep D packing material was found to work well for gas separation. A traditional GC setup may not allow accurate measurements of H$_2$S at low concentrations (~1-10 ppm) because: 1) H$_2$S may react with the flow path plumbing, and 2) the GC's TCD may not be sensitive enough to detect such low concentrations. To improve the detection limits, all wetted parts are made of stainless steel or glass, and pure H$_2$S was run through and maintained in the flow path for several weeks prior to the experimental runs to deactivate the plumbing.

Work performed quantified the sensitivity limits of the GC to be at least 150 ppm H$_2$S, corresponding to 0.015 vol % of H$_2$S. Alternative H$_2$S detection methods, such as a flame photometric detector, and inert tubing treated with silane (SiHd to render it more resistant to H$_2$S attack can be used to achieve lower threshold detection limits. It is noted that during successful experiments, no H$_2$S "rotten egg" smell was detected, suggesting H$_2$S was present at less than 5 ppb.

The GC has a low sensitivity which attenuates the peak height of all detected peaks when used, such that larger ones are shown in their entirety on the chromatogram, but small peaks are reduced to undetectable levels.

The relation between GC peak area and H$_2$S concentration was determined. Carefully metered gases of 0.02%, 0.1%, 1%, 5%, and 10% H$_2$S concentrations were sent to the GC. The TCD readings of five samples at each concentration were averaged to determine the normalized coefficients for each species. FIG. 4-1 and FIG. 4-2 of U.S. Patent Application Ser. No. 61/646,576 incorporated by reference herein in its entirety show the coefficients for peak area to concentration for high and low GC sensitivity respectively.

In the low sensitivity mode data was only collected for concentrations of 1% $H_2S$ and above, as the 0.1% and 0.02% feed streams led to no detection of $H_2S$. Intermediate concentrations were also measured individually (not shown) to confirm it was appropriate to assume a linear relationship between peak area and concentration.

Titration was used to analyze the liquid scrubbing portion of the solution. To measure the $Br_2$, HBr and $H_2SO_4$ concentrations in solutions, 1 ml samples of solution were mixed with 99 ml of deionized water. The following procedures were then followed: Bromine Analysis—Approximately 10 times excess KI was added to the sample to convert any bromine to bromide, and produce the yellow to deep brown iodine:

$$2KI(aq)+HBr_3(aq) \rightarrow HBr(aq)+2KBr(aq)+I_2(aq)$$

A starch indicator was added to the sample that turned purple in the presence of iodine.

The solution was then titrated with a 0.1 M solution of sodium thiosulfate:

$$I_2(aq)+2Na_2S_2O_3(aq) \rightarrow 2NaI(aq)+Na_2S_4O_6(aq)$$

When the sample turns clear from light yellow, the titration is complete. Excess KI does not affect the sample, but must be added before the starch indicator.

Total Acid Analysis—A few drops of sodium thiosulfate were added until the solution is clear to remove bromine which may have a brownish color:

$$HBr_3(aq)+2Na_2S_2O_3(aq) \rightarrow 2NaBr(aq)+Na_2S_4O_6(aq)+HBr(aq)$$

Phenolphthalein indicator was added that turned pink at the pH of 8 endpoint.

The solution was then titrated with 1 M NaOH to a pH of 8:

$$HBr(aq)+NaOH(aq) \rightarrow NaBr(aq)+H_2O$$

and $$H_2SO_4(aq)+2NaOH(aq)Na_2SO_4(aq)+2H_2O$$

When the sample turns pink the titration is complete. Excess sodium thiosulfate is not a problem at the beginning because it is a neutral solution.

Total Bromide Analysis—A few drops of sodium thiosulfate were added until the solution was clear to remove bromine which may have a brownish color:

$$HBr_3(aq)+2Na_2S_2O_3(aq) \rightarrow 2NaBr(aq)+Na_2S_4O_6(aq)+HBr(aq)$$

Potassium Chromate, $K_2CrO_4$, was added that turned brick red at the endpoint in the presence of $Ag^+$ ions.

$$K_2CrO_4(aq)+2AgNO_3(aq) \rightarrow 2AgCrO_4(s)+2KNO_3(aq)$$

The solution was then titrated with 1 M $AgNO_3$:

$$HBr(aq)+AgNO_3(aq) \rightarrow AgBr(s)+HNO_3(aq)$$

When a brick red precipitate occurs the titration is complete. Excess sodium thiosulfate is not a problem at the beginning, and sulfuric acid does not interact with silver nitrate.

The bromine ($Br_2$) concentration is calculated from the amount of sodium thiosulfate titrant added in the first titration. The hydrobromic acid (HBr) concentration is determined by subtracting twice the bromine concentration from the calculated bromide concentration in the third titration, and the sulfuric acid ($H_2SO_4$) concentration is found by subtracting the calculated hydrobromic acid concentration from the total acid ($H^+$) concentration from the second titration and then dividing by two.

The titration methods devised for analyzing solution compositions were tested on known $Br_2$, HBr, and $Br_2$/HBr solutions to verify their accuracy. The execution of the test titrations went as expected with regards to indicator color changes.

Initially the amount of titrant required for $Br_2$ and HBr analysis were within 5% of that expected, but upon further practice and refinement of the procedure an error margin of 1% was achieved. The initial errors are explained by not properly mixing the solutions before titrating.

The first set of titrations was of an aqueous solution expected to be 48.1 wt % HBr. The average composition determined from three titrations was 48 wt %, as shown in Table 4-1.

The second set of titrations was that of $Br_2$ diluted in water to approximately 0.155 M (2.44 wt %). The solution was made by mixing 2 ml of $Br_2$ with 250 ml of water. The titration required 2.4 ml of 0.0640 M of $Na_2S_2O_3$, which corresponds to a $Br_2$ concentration of 0.151 M. In practice it was difficult to measure the exact volume of $Br_2$ added to the solution as its volatility in its pure state causes it to vaporize and push out of the pipette. The titrations performed yielded the results shown in Table 4-2. The third set of titrations was of a solution of 1.8 ml $Br_2$ and 1.8 ml HBr (aq, 47 wt %) in 97 ml of water. The total volume of this solution was 100.5 ml. The solution was expected to be 0.345 M (5.3 wt %) $Br_2$ and 0.209 M (1.7 wt %) HBr, and it was titrated to be 0.336 M (5.2 wt %) $Br_2$ and 0.215 M (1.7 wt %) HBr, as shown in Table 4-3.

Some additional titrations were performed and the amount of titrant required for $Br_2$ and HBr analysis were within a few percentage of expectation. These results for known $Br_2$, HBr, and $Br_2$/HBr solutions are summarized in Table 4-1.

Due to initial difficulty in verifying solution concentrations it was a relief to have such consistent results. The pictures in FIG. 4-3 of U.S. Patent Application Ser. No. 61/646,576 incorporated by reference herein in its entirety show the standard $Br_2$ and HBr solutions on left, and the standard titrant solutions made to confirm the titration methods on right.

A quick and simple method for detecting sulfuric acid is to convert it to a solid insoluble sulfate that would precipitate out of solution. This solid is visible, and can be separated, dried and weighed to estimate the amount of sulfuric acid present, though this later method is not used due to the improved accuracy of the titration methods.

The complication comes from hydrobromic acid also being present, which runs the risk of competitively forming an insoluble bromide. By example lead sulfate is very insoluble, but so is lead bromide, so mixing a lead compound into the solution and finding a precipitate will not confirm only one is present. An additive that is soluble in hydrobromic acid, does not form an insoluble bromide and does form an insoluble sulfate is needed.

Most nitrates and hydroxides are soluble in water, while most sulfates are not. Bromides of calcium, strontium, and barium are all soluble in water and acids. $Ba(OH)_2$, $Sr(OH)_2$, $Sr(NO_3)_2$, and $Ba(NO_3)_2$ would all work, but $Ca(NO_3)_2$ was selected because it is readily available. To confirm, $Ca(NO_3)_2$ was put in a solution of hydrobromic acid and sulfuric acid. In the former case no precipitate was detected, while in the later a significant amount of precipitate formed. When a spent reactor solution was mixed with $Ca(NO_3)_2$ a precipitate occurred, confirming sulfuric acid was being formed by the reaction.

X-ray photoelectron spectroscopy (XPS) is a surface chemical analysis technique for analyzing the surface chemistry of a material. It works by irradiating a material sample with a beam of x-rays, and measuring the kinetic energy and quantity of electrons that escape from the top 10 nm of surface. It can determine the empirical formula and elemental composition of a material, as well as the chemical and electronic states of the elements present. The method requires analysis under ultra high vacuum conditions, which necessitates the sample be a solid. FIG. 4-4 of U.S. Patent Application Ser. No. 61/646,576 incorporated by reference herein in its entirety illustrates the basic process.

XPS detects all elements present to parts per thousand concentration except hydrogen and helium. It is possible to detect down to parts per million, but this requires special conditions, equipment modifications, and potentially very long collection times. Additional details on how XPS works are provided in the references. [Reference 83].

Example 1: Initial Bench Scale Process

An initial process setup in accordance with the present disclosure, including equipment, flow paths, sample analysis points and principal components are illustrated in FIG. 4-5 of U.S. Patent Application Ser. No. 61/646,576 incorporated by reference herein in its entirety. Recycling bromine in a closed cycle is not performed due to the unnecessary burden it places on the initial experiments. The initial process is described in detail as it is the basis for and very similar to a subsequent process setup.

Correlated rotometers regulate the amount of gas coming from three source tanks: 100% nitrogen ($N_2$), 10% $H_2S$ with 90% $N_2$ carrier gas, and 100% methane ($CH_4$). These gases are mixed and then bubbled through a column filled with the $Br_2/HBr/H_2O/H_2SO_4$ solution. The gas is forced through a glass frit at a regulated pressure just above atmospheric to create small bubbles for improved mass transport between gas and solution. At this point $H_2S$ is removed from the gas through reaction with aqueous $Br_2$.

A part of the gas stream is bled off for gas chromatography (GC) analysis prior to entering the reactor and after exiting the water scrubbers to detect and quantify $H_2S$, $Br_2$, HBr, $H_2O$, $CH_4$, $N_2$ and other species present.

A small amount of $H_2O$ and HBr can evaporate into the $N_2$ and $CH_4$ carrier gas stream and leave the reactor. Therefore the gas stream passes through a water filled column to remove highly soluble HBr prior to being sent to the GC. Before collecting data, $H_2S$ is run through these scrubbers until saturation to prevent the absorption of unreacted $H_2S$ into these solutions. This allows for a more accurate measurement of $H_2S$ removed by the reactor. After the water scrubber the gas is vented to the environment.

FIG. 4-6 of U.S. Patent Application Ser. No. 61/646,576 incorporated by reference herein in its entirety shows the initial process setup in its entirety. Three gas cylinders containing ultra high purity nitrogen (99.999%), 10% hydrogen sulfide in nitrogen balance (±2%), and industrial grade methane (99%) furnished by Air Gas South are shown in FIG. 4-7 (10% $H_2S/N_2$, $N_2$, and $CH_4$) of U.S. Patent Application Ser. No. 61/646,576 incorporated by reference herein in its entirety. The cylinders fed three correlated rotometers and a static gas mixer as shown in FIG. 4-8 of U.S. Patent Application Ser. No. 61/646,576 incorporated by reference herein in its entirety, where the gases were metered and mixed to the desired concentration.

The feed stream then entered a 125 ml reactor column where a glass frit created small bubbles to increase contact with the reactant solution composed of aqueous $Br_2$ and HBr. This column was placed in a water bath on a hot plate to control its temperature. The reactor gas stream flowed to a water scrubber to capture fugitive HBr vapors for analysis and to prevent corrosion of the Gas Chromatograph's inner components. The reactor and the initial water scrubber are shown in FIG. 4-9 of U.S. Patent Application Ser. No. 61/646,576 incorporated by reference herein in its entirety.

Following the water scrubber, the effluent gas stream flowed through a length of Teflon® tubing to a Valco® six-port valve, as shown in FIG. 4-10 of U.S. Patent Application Ser. No. 61/646,576 incorporated by reference herein in its entirety, with ~1 µL sample loop for injection into the GC where it was analyzed by a thermal conductivity detector (TCD.) This reduces the possibility of contamination and gives consistently repeatable samples since it avoids the human variability inherent to using a syringe for the injection. The HP 5890A Gas Chromatograph (GC) used for sample analysis is shown in FIG. 4-11 of U.S. Patent Application Ser. No. 61/646,576 incorporated by reference herein in its entirety.

A second line of tubing with three valves allowed diversion of the gas flow around the reactor and scrubber straight to the GC. This allowed the reactant feed stream to be analyzed periodically to check that a consistent feed is maintained throughout the experiments. The tee, multiple valves, bypass line and reactor line with common outlet to GC are shown in FIG. 4-12 of U.S. Patent Application Ser. No. 61/646,576 incorporated by reference herein in its entirety.

Four additional tasks were necessary to make the apparatus functional and ready for experiments: setting up and calibrating the rotometers, assembling the reactor system, and getting the gas chromatograph operational for analyzing the gas streams with an appropriate GC column and proper GC settings for accurate analysis.

A Cole-Parmer Flowmeter System consisting of a multi-tube frame, three 65 mm flow tubes with glass floats and aluminum wetted parts was used. It was initially a challenge to control the flow rates because the lowest delivery pressure (~2 psig) resulted in very high flow rates through the rotometers, pushing the glass floats beyond full scale after turning the knobs only a fraction. Several metering valves were obtained and placed inline between the cylinders and rotometers, providing a second stage of regulation, and better control of the flow rates. One such valve is shown in FIG. 4-13 of U.S. Patent Application Ser. No. 61/646,576 incorporated by reference herein in its entirety.

Initially several difficult to detect leaks caused inconsistencies and prevented a steady flow rate over extended periods of time. Immersing the rotometer in water revealed bubbles from the leaks, and allowed them to be sealed properly. After adding the metering valves and correcting the leaks, the rotometers gave consistent results and were calibrated using a soap film flow meter and stopwatch to obtain the flow rates of the individual gases over the 65 mm rotometers scale. FIG. 4-14 of U.S. Patent Application Ser. No. 61/646,576 incorporated by reference herein in its entirety shows the volumetric flow rate versus rotometer metering scale.

Various combinations of glassware and tubing were trialed until the reactor setup was achieved. Vinyl tubing was used to couple stainless steel tubing to glass connections. TEFLON® tubing connected the scrubber outlet to the GC inlet, and the bypass line from the rotometers directly to the GC. A 125 ml column was chosen for the reactor and two 40 ml columns with fritted stems were used for water scrubbers.

The frits split the flow into many small gas bubbles that rise through the liquid with a large surface area. This increases the gas-liquid interface available for reaction and thereby increases the reactor and scrubber efficiencies.

FIG. 4-15 of U.S. Patent Application Ser. No. 61/646,576 incorporated by reference herein in its entirety shows the experimental setup. The titration equipment used for analyzing $Br_2$ and HBr content is visible in the left of the photo. The reactor is on the right, with tubing connecting it to two water scrubbers located in the middle. Rotometers for measuring flow are on the far right. This was the test bed for a more precise second set up.

A Hewlett-Packard 5890A GC was obtained, and a packed column that would adequately recognize and separate the peaks of interest ($N_2$, $H_2S$, $H_2O$, $Br_2$, HBr, $CH_4$) was sought. Four columns with three different packing materials were tested. An 8'33 1/8" stainless steel column with HayeSep Q packing from Alltech was tested based on product information suggesting it would recognize $H_2S$ and provide separation of the $H_2S$ and $H_2O$ peaks. Then a 1/8" molecular sieve 5A column, a 10'×1/8" HayeSep D column and a newly packed 23'×1/8" HayeSep D column were also tested. Two GC results for HayeSep D and Q for nitrogen, methane and hydrogen sulfide flows are shown in FIG. 4-16 and FIG. 4-17, respectively, of U.S. Patent Application Ser. No. 61/646,576 incorporated by reference herein in its entirety.

Methane is eluted early after nitrogen (identified as air since it elutes alongside oxygen), but unfortunately in all cases, the $H_2S$ and $H_2O$ peaks eluted from each column after similar retention times and when one peak became large (i.e. high concentration of one or both components) the two peaks would become indistinguishable.

A lower oven temperature and column flow rate were tested to spread the peaks out, at the sacrifice of longer analysis times, but this led to an unstable baseline and the presence of unknown peaks that did not correspond to any actual species. Since a longer column can help separate close peaks, the 10' and 23' HayeSep D columns were coupled to the 8' HayeSep Q column yielding better results but still not enough to use in experiments.

In a last effort the column temperature was further reduced. Previous experiments went as low as 80° C. but no lower due to the trend of decaying baseline stability. By lowering to 60° C. the data showed adequate separation of the $H_2S$ and $H_2O$ peaks along with a stable, well-defined baseline. After switching back to the 10' HayeSep D column and adjusting the column flow rate, a usable set of operating conditions was established.

After testing almost thirty different configurations at a variety of conditions, the GC was operated at column/oven temperature of 70° C., injector temperature of 100° C., detector temperature of 140° C., column pressure of 40 psig, column flow rate of 26 cc/min, and reference gas flow rate of 33 cc/min. These conditions were found favorable for separating $H_2O$ and $H_2S$, and give a column-to-reference flow ratio of 1:1.27.

Initially 1 cc samples were drawn through a septum port on the scrubber outlet into a syringe and injected manually into the GC, but this led to very large peaks in the chromatogram. A micro liter syringe was obtained and 0.5 µL samples gave more manageable peak sizes, but the results were inconsistent and contaminated with water.

The syringe allowed too much sample size error, which led to inconsistent peak sizes. Without wetting the syringe plunger, the sample would be pushed out the back of the syringe rather than into the GC, which in turn added water to the sample. At this point a VALCO® injector valve was obtained, and several different sized sample loops were tried before converging on a ~1 µL loop as shown in FIG. 4-10 of U.S. Patent Application Ser. No. 61/646,576 incorporated by reference herein in its entirety.

During the course of preliminary exploration and setup, several discoveries were made regarding the behavior of the system. Initial runs were performed with only water in both the reactor and scrubber. $N_2$ carrier gas was sent through the reactor/scrubber and the dry bypass line. Then 10% $H_2S/N_2$ was passed through the reactor/scrubber and the bypass line. These series of runs revealed that only three distinguishable and measurable peaks appeared in the chromatogram and clearly belonged to $N_2$, $H_2S$ and $H_2O$. At the stated GC settings, $N_2$ elutes from the column at 0.9 min, $H_2S$ at 8.8 min and $H_2O$ at 10.6 min as shown in FIG. 4-18 of U.S. Patent Application Ser. No. 61/646,576 incorporated by reference herein in its entirety.

After replacing the water in the reactor and scrubber for the first time in several weeks the $H_2S$ peak in the GC chromatogram was much smaller than previously measured and shown in FIG. 4-18 of U.S. Patent Application Ser. No. 61/646,576 incorporated by reference herein in its entirety. Over time the size of this peak slowly increased despite the feed concentration being constant. As expected, the $H_2S$ was dissolving in the water.

$H_2S$ is soluble in water as shown above. At 20° C. the solubility of $H_2S$ is 3.9 g/kg water, which is more than twice as soluble as $CO_2$ (1.2 g/kg water), and a hundred times greater than methane (0.035 g/kg water). This is expected to encourage the desired bromination reactions since $H_2S$ dissolves in the liquid readily, becoming available for reaction. Methane is not soluble and should pass through the bromine solution unaffected.

As $H_2S$ was permitted to flow for sufficient time through the reactor and scrubber, the $H_2S$ peak increased in size until it reached a maximum. FIG. 4-19 of U.S. Patent Application Ser. No. 61/646,576 incorporated by reference herein in its entirety shows a small $H_2S$ peak at the start of flowing a 10% $H_2S/N_2$ balance feed stream through newly replaced water not saturated with $H_2S$. FIG. 4-18 of U.S. Patent Application Ser. No. 61/646,576 incorporated by reference herein in its entirety shows the peaks after the 10% $H_2S/N_2$ balance feed stream saturates the water with $H_2S$.

FIG. 4-20 of U.S. Patent Application Ser. No. 61/646,576 incorporated by reference herein in its entirety shows a GC chromatogram of 10% $H_2S/N_2$ through the dry bypass line. The total peak area of $H_2S$ matches that of the wet reactor line after $H_2S$ saturation of the water shown in FIG. 4-18 of U.S. Patent Application Ser. No. 61/646,576 incorporated by reference herein in its entirety, indicating that the water was saturated, and thus the $H_2S$ entering the saturated water scrubber equaled the $H_2S$ leaving the scrubber.

To understand the time to saturate the water solution with $H_2S$ the system was filled with 160 ml of deionized water, and the rotometers were set to allow 4 cc/min of 10% $H_2S$ in $N_2$. The outlet stream was periodically sampled with the GC to measure the $H_2S$ peak area until it reached a maximum as shown in FIG. 4-21 of U.S. Patent Application Ser. No. 61/646,576 incorporated by reference herein in its entirety, at which point the water was saturated with $H_2S$. This took ~36 hours and the total amount of $H_2S$ passed through the solution was ~10 g (7250 cc @20° C., 1 atm) while 0.621 g (440 cc) is thought to have been absorbed into the water solution.

Concern arose over $H_2S$ being removed through its absorption into water, and not through its reaction with bromine in the water solution. If the water absorbed $H_2S$ without reacting it should show up as less $H_2S$ coming out AND no $Br_2$ converted to HBr. Alternatively if saturated water were used to make the scrubbing solution, the $H_2S$ in solution should react with $Br_2$ to make HBr before any $H_2S$ is flowed, then causing the removal of $H_2S$ from its absorption into solution based on its solubility alone.

To test the latter, a known quantity of $Br_2$/HBr was added to water saturated with $H_2S$, and the solution was titrated to see if the $Br_2$ was consumed from mixing the two together. Upon saturating the water in the reactor and two scrubbers with $H_2S$, a solution of 3 ml $Br_2$ and 15 ml HBr (aq, 48 wt %) was added 1 ml at a time with a pipette to 80 ml of $H_2S$ saturated solution. The 1st ml caused the clear $H_2S$/water solution to turn pale yellow with slight cloudiness and a small number of bubbles to be generated for several seconds. The 2nd ml made the color turn pale red with no further bubbling or clouding, and subsequent addition led to a darkening to a brownish red color.

The reactor solution was then titrated, and results showed a trend consistent with expectation: a decrease in $Br_2$ concentration, and an increase in HBr and sulfuric acid concentration. The concentration in the reactor immediately prior to reaction should be 0.60 M $Br_2$ and 1.35 M HBr if there were no reaction with dissolved $H_2S$, and 0.43 M $Br_2$ and 1.69 M HBr if the water were 100% saturated with $H_2S$ at 25° C. (3.6 gram $H_2S$ per kg water) and all of it reacted with bromine in the expected reaction.

The post-reaction titrations found concentrations of 0.44 M $Br_2$, 1.67 M HBr, and 0.08 M $H_2SO_4$ corresponding to a consumption of 0.015 mol $Br_2$ and production of 0.031 mol HBr along with 0.008 mol of $H_2SO_4$. The 98 ml of solution held 0.008 moles or 0.27 grams of $H_2S$, which is 92% of the expected amount of $H_2S$ when saturated. The values obtained are consistent with sulfuric acid being the main sulfur product.

$H_2S$ was bubbled through a 1.1 wt % $Br_2$ and 13.4 wt % HBr solution, and over the course of five hours all the bromine reacted to form HBr as evidenced by the solution turning clear and the detection of increased HBr in the reactor solution.

The removal of $H_2S$ was verified through gas chromatograph results which did not detect $H_2S$ in the post-reactor gas stream while bromine was visible in the reactor. The GC output in FIG. 4-22 of U.S. Patent Application Ser. No. 61/646,576 incorporated by reference herein in its entirety shows the $H_2S$ going into the reactor. The small water peak is from some water condensation that was visible in the GC sample feed line.

The GC output in FIG. 4-23 of U.S. Patent Application Ser. No. 61/646,576 incorporated by reference herein in its entirety shows the same gas stream coming out of the reactor during the five hour run. The presence of water is because the reactor and scrubbers saturate the exiting gas with water, which has a strong peak due to its high conductivity.

These GC outputs were the first conclusive proof that the $Br_2$/HBr solution removed $H_2S$. A second run showed that without bromine, a HBr solution did not remove any $H_2S$.

The eight images in FIG. 4-24 of U.S. Patent Application Ser. No. 61/646,576 incorporated by reference herein in its entirety show the reactor solution color transition during the run, and illustrate the conversion of red bromine into clear hydrobromic acid. After turning clear, signaling the absence of $Br_2$ in solution, $H_2S$ rapidly appeared in the GC output.

The two water bubbler solutions were analyzed at the end of the experimental run for HBr content. No measureable HBr was found in the bubblers, which agrees with HBr being highly soluble in the reactor water. At more concentrated hydrobromic acid reactor solutions, higher temperatures, and larger gas flow rates, a measureable quantity of HBr may be transferred to the water bubblers.

$H_2S$ was bubbled through 100 ml of 10 wt %, 20 wt %, 30 wt %, and 40 wt % $H_2SO_4$ solutions. It was expected that one of two processes would occur. If $H_2S$ reacted with $H_2SO_4$ then the $H_2S$ peak would reduce or disappear from the GC chromatogram. If the two species do not react, then the $H_2S$ may be absorbed by the water, causing the $H_2S$ GC peak to reduce until the water became saturated with $H_2S$ (up to 5 hours). No new gas species were observed and the liquid concentration of $H_2SO_4$ did not decrease, indicating that no reaction occurred between $H_2S$ and $H_2SO_4$.

A feed gas of 10 vol % $H_2S$ in $N_2$ was flowed through the four sulfuric acid solutions at a rate of 19.5 cc/min. If the $H_2S$ peaked reduced and returned after less than five hours, then it could be due to absorption by the water with no reaction occurring. If it took significantly longer for the peak to return, a reaction may be occurring.

Interestingly, the $H_2S$ peak did not disappear significantly from the GC chromatograms during the first two hours of reactor flow. In prior runs, $H_2S$ was absorbed by the water until saturation (<0.4g/100 mL at 20° C.), after which point all $H_2S$ would pass through and show up as a full peak in the GC data. However, when the $H_2S$ peak was observed it was 60% of the area corresponding to full concentration, and quickly increased to full concentration (10 vol %) over 2 hours where it remained for each run.

After 8 hours in each run, samples were drawn from the reactor and titrated with NaOH. Since no bromine was present, all acid detected was considered to be sulfuric acid. The $H_2SO_4$ concentration in the reactor increased from 1-4% in each run. This is attributed to water vapor being carried out of the reactor to the secondary water column by the gas feed. Since $H_2SO_4$ would not be carried off and none appeared to react, the concentration of $H_2SO_4$(aq) would therefore increase slightly over time.

For these experiments the glass frit was replaced by an open-ended tube. This was expected to cause a large decrease in mass transfer of $H_2S$ between the gas and liquid because the gas comes out as large bubbles instead of the many small bubbles of the fritted tub. This may explain why $H_2S$ is detected prior to its expected saturation in the sulfuric acid. The solubility of $H_2S$ in sulfuric acid may also be less than as calculated for pure water.

Initially it was not known whether sulfur, sulfuric acid, or some combination of the two along with other sulfur species would form. The process by which reaction products were produced and identified is now described.

Early on it became important to determine if sulfuric acid was being formed. The calcium nitrate precipitate method confirmed sulfuric acid was a product, but after running a series of experiments with high bromine concentrations, a small but visible amount of solid particulate accumulated at the bottom of the reactor column.

It appeared as a whitish-yellow-brown color, and lacked the typical yellow color of elemental sulfur. The amount was very small, about 0.1% of the amount that would be expected if all the $H_2S$ were converted to solid sulfur, but it could not be ignored since the formation of any precipitate has implications for process design and maintenance.

The exact sulfur compound was in question, and the color suggested it may be a sulfur bromine compound. To identify the solid precipitate a series of concentrated $Br_2$ runs were undertaken with high $H_2S$ flow rates to move as much sulfur through the reactor as possible and produce a larger quantity of the precipitate. Experimental precision was not required for this, since the purpose of these runs was to collect enough solid material to analyze with x-ray photoelectron spectroscopy (XPS) in order to determine the composition of this solid material.

The runs began by flowing 10% $H_2S$ in $N_2$ through a relatively concentrated 1 M $Br_2$ solution (~14 wt %). The gas flowed until the color of the solution turned clear, indicating consumption of all the bromine, then more $Br_2$ was added and the run was repeated. As the runs progressed the solid became more noticeable. FIG. 4-25 of U.S. Patent Application Ser. No. 61/646,576 incorporated by reference herein in its entirety shows the accumulation at the end of ten such runs, and the total amount collected.

After each run the solid was collected by pouring the spent reactor solution through a filter paper and allowing sufficient time to air dry. The resulting powder was inserted into an ultra-high vacuum chamber for analysis with x-ray photoelectron spectroscopy and spectra were obtained that confirmed elemental sulfur as the predominant species.

The XPS survey spectrum shown in FIG. 4-26 of U.S. Patent Application Ser. No. 61/646,576 incorporated by reference herein in its entirety was obtained with excellent signal-to-noise ratio, and shows characteristic peaks for sulfur, carbon, oxygen, and bromine. The C is peak is typical of most samples and is due to adventitious carbon, or hydrocarbon contamination from the atmosphere. This peak was shifted to 284.6 eV and used as the reference for shifting all spectra. The large O 1s oxygen peak centered at 532.3 eV is indicative of physisorbed water, which is expected when analyzing an air-dried sample recovered from an aqueous solution. The S $2p$, S $2s$, and Br $3p$ data are difficult to analyze due to their small signal, but suggest one state of sulfur and one of bromine.

The S $2s$ peak at 164 eV and S $2p$ peak at 235 eV indicates the presence of elemental sulfur. The bromine peak of interest is the Br $3p$ peak at 69 eV, which could result from a sulfur bromine compound, or bromine physisorbed on the surface of sulfur since the volatility of $Br_2$ would prevent it from remaining on the filter paper under vacuum. Additional XPS runs were performed which yielded much higher S-to-Br peak ratios, suggesting there is far more S than Br on the surface.

High resolution XPS data shown in FIG. 4-27 of U.S. Patent Application Ser. No. 61/646,576 incorporated by reference herein in its entirety confirms one state of oxygen making it unlikely the solid compound contains any oxygen since no other oxygen states are apparent. The presence of the one, smooth peak in the S $2p$ spectrum indicates only one species of sulfur is present. This peak is centered at 163.4 eV, which is indicative of elemental sulfur. The Br $3p$ spectrum had a poor signal to noise ratio due to the low amount of Br present on the sample, but shows one main feature centered at 70.0 eV with a shoulder at lower BE. It is believed that the feature at 70.0 eV is due to physisorbed $Br_2$, while the shoulder may either be due to noise or the small presence of a bromide salt.

This initial process setup in accordance with the present disclosure proved that elemental sulfur can be produced during the reaction between $H_2S$ and concentrated $Br_2$. It has also shown that small amounts of $Br_2$ can remain unreacted when adsorbed to the surface of the sulfur precipitate, and that S—Br, SO and/or S—Br—O compounds are highly unlikely.

The solid precipitate was only produced with relatively concentrated bromine solutions of 1 M or ~14 wt %. The process is expected to operate with a 0.05 M (0.8 wt %) bromine solution, and will certainly not exceed 0.2 M so the formation of this precipitate is not. Further experiments at lower bromine concentrations did not produce any solids.

Several limitations were identified with the initial process setup. Its dead volume is relatively large, so gas that enters the reactor does not reach the GC for analysis until 15 minutes have elapsed. The reactor does not have a sample port, and must be filled through a tedious process of disassembly.

Not being able to draw samples of the reactor solution and the delay between what is visible in the reactor and what is detected by the GC makes it difficult to know what is happening at the crucial limiting condition when bromine is nearly depleted.

Another drawback of the apparatus is that the rotometers do not allow precise and reproducible control of the inlet gases. Rotometers measure flow, they do not control it, and unfortunately it became difficult to achieve a consistent flow rate over multi-hour test runs. The rates of gas flow would vary during a run, making it nearly impossible to accurately assess how much $H_2S$ was entering the reactor.

Example 2: Modified Bench Scale Process

An improved process set up with a mechanical mixer, temperature probe and outer jacket for heating and cooling the solution was assembled. Shorter connections between reactor and scrubber, and smaller diameter bypass and exit lines were used to reduce the time for gas to pass through the system. Ports on the reactor and water scrubbers allowed solution samples to be withdrawn for analysis without opening the vessels and interrupting experiments, and wetted parts were made of glass to eliminate contamination from materials that might react. FIG. 4-28 of U.S. Patent Application Ser. No. 61/646,576 incorporated by reference herein in its entirety shows the improved process setup.

FIG. 4-29 of U.S. Patent Application Ser. No. 61/646,576 incorporated by reference herein in its entirety shows two views of the reactor. The three items at the top from left to right are the gas entry/exit, the mechanical mixer connection and the temperature probe. The image at right shows a detail of the reactor and heating/cooling jacket.

The left image of FIG. 4-30 of U.S. Patent Application Ser. No. 61/646,576 incorporated by reference herein in its entirety shows the new mass flow controllers and the plumbing that connects the reactor, scrubber, gas tanks and analytical equipment. The image at right shows from left to right the gas entry and exit, the mixer, and the temperature probe. The back right shows the water column for capturing any $Br_2$ or HBr vapors that may escape the reactor. In the back left are two three-way valves for directing flow through the reactor or the bypass line, and for positive isolation of the unused line.

The $CH_4$, $N_2$ and $H_2S/N_2$ gas streams are controlled by electronic thermal mass flow controllers shown in FIG. 4-31 of U.S. Patent Application Ser. No. 61/646,576 incorporated by reference herein in its entirety. These devices provide precision accuracy in controlling each gas's flow rate, and therefore the overall gas mixture composition.

The reactor is heated by an electric heating tape. Temperature is controlled by adjusting the heating tape voltage with a variable AC transformer (Variac) and monitoring the temperature with the thermocouple with digital readout. Cooling is achieved by running chilled water around the reactor's outer jacket.

The line from the MFCs to the reactor, the bypass line, and the line from the reactor to the GC is Teflon tubing since glass tubing is impractical for these applications. ⅛" tubing was used in place of ¼" to minimize the time the gas takes to travel.

Upon assembling the new reactor a few runs were performed to become familiar with its operation and to draw samples during the experiment to see how the reactor solution was varying over time. A 90 ml solution containing 0.141 moles of bromine and 0.159 moles of HBr at 25° C. was exposed to 0.00049 moles per minute of $H_2S$. Each hour a sample was taken and titrated for $Br_2$, HBr and $H_2SO_4$ content. FIG. 4-32 of U.S. Patent Application Ser. No. 61/646,576 incorporated by reference herein in its entirety shows the expected species concentration over the experiment along with the actual results from the titration.

The reaction progressed as expected with one mole of sulfuric acid and four moles of HBr being generated for every mole of $H_2S$ and $Br_2$ consumed. The variation from the expected line seen in the above chart is associated with the titration. Similar results were obtained when starting with some initial sulfuric acid content.

Using reaction mechanisms proposed in the prior chapter a generalized reaction rate of the following form was found:

$$\partial(H_2S)/\partial t = k_1(T)(H_2S)^v(Br^2)^w(H_2O)^x - k_2(T)(S)^u (H_2SO_4)^y(HBr)^z \quad \text{Eq. 4-1}$$

In all the experiments run, all $H_2S$ passed through bromine solution reacted to form HBr. There may be a period at very low bromine concentration when some $H_2S$ does not react, but it was not possible to investigate this region with the existing setup.

Experiments with 10%, 35%, 70% and 100% $H_2S$ feed gas concentrations were run in order to determine rate coefficients and reaction order for $Br_2$ and $H_2S$ concentrations. A constant feed gas rate of 9.89 cc/min (8.10 cc/min for the 100% case) and an aqueous solution of ~0.2-0.3 mol/L $Br_2$ in ~0.3-0.4 mol/L HBr were used. Liquid samples were taken from the reactor every ~5 mins during the reaction to obtain $Br_2$ and HBr concentration during reaction. $Br_2$ concentration is plotted versus time in FIG. 4-33 of U.S. Patent Application Ser. No. 61/646,576 incorporated by reference herein in its entirety.

FIG. 4-34 of U.S. Patent Application Ser. No. 61/646,576 incorporated by reference herein in its entirety presents the natural log of $Br_2$ and inverse of $Br_2$ concentration plotted versus time.

For all four $H_2S$ concentrations the plot of $Br_2$ concentration versus time shown in FIG. 4-33 of U.S. Patent Application Ser. No. 61/646,576 incorporated by reference herein in its entirety was reasonably linear, whereas the plots shown in FIG. 4-34 of U.S. Patent Application Ser. No. 61/646,576 incorporated by reference herein in its entirety were not. The linearity observed with respect to $Br_2$ concentration indicates the formation of HBr is zero order with respect to $Br_2$ and thus $Br_2$ concentration does not affect the reaction rate. FIG. 4-35 of U.S. Patent Application Ser. No. 61/646,576 incorporated by reference herein in its entirety displays data taken from low and high (0.074 and 0.30 mol/L) concentration $Br_2$ solutions during reaction with a 10% $H_2S/N_2$ feed stream. The two trend lines both have −0.009 slope, which indicates both experiments yielded the same rate coefficient. This further confirms that the system is zero order with respect to $Br_2$.

Similar experiments with different HBr and $H_2SO_4$ concentrations up to 4 M (22 wt % HBr and 26 wt % $H_2SO_4$) each did not have an effect on the $H_2S$ reaction rate, which was found to be dependent on the $H_2S$ flow rate. This suggests that the generalized reaction equation simplifies to a constant value equal to the $H_2S$ flow rate.

The reaction appears to be irreversible, and therefore mass transfer limited, by the diffusion of $H_2S$ into the aqueous bromine solution. In the reactor, the rising gas bubble contains $H_2S$ and a little water vapor with other essentially inert species such as methane and nitrogen. Methane is slightly soluble in hydrobromic acid, but this amount is inconsequential as there is no valid reaction mechanism for its consumption.

The $H_2S$ is absorbed into solution where it encounters a bromine depleted region. A little further from the bubble surface is the reaction horizon where $H_2S$ diffusing into the solution meets and reacts with bromine diffusing from the bulk solution. Up until this point the concentration of $H_2S$ is decreasing. As one moves further into the solution, bromine begins to appear and eventually meets its bulk concentration.

FIG. 4-36 of U.S. Patent Application Ser. No. 61/646,576 incorporated by reference herein in its entirety illustrates how these concentrations may vary relative to the sour gas bubble.

Rate coefficients are temperature dependent, so the above experiments were repeated at elevated and reduced temperatures. This information could then be used to obtain the rate coefficient as a function of temperature, according to the equation:

$$k(T) = A \exp(-E_{act}/RT) \quad \text{Eq. 4-2}$$

where k is the rate coefficient, $E_{act}$ the activation energy, T the temperature in Kelvin, R the ideal gas constant (8.314 J/mol·K), and A the pre-exponential factor.

A pump circulated cold water from an ice bath around the reactor jacket, allowing experiments to be run at ~10° C. Then hot water was pumped through the reactor's heating/cooling jacket, allowing the experiments to be repeated at ~35° C. Table 4-5 shows the rate coefficients calculated from the present experiments.

In all three cases the incoming $H_2S$ reacted with the solution at the same rate, which goes against expectations for a faster reaction at higher solution temperatures. The explanation could lie in a couple overlapping areas. For one, the rate is roughly proportional to the $H_2S$ flow rate, so the $H_2S$ flow rates used may have been low enough that there was plenty of time for the $H_2S$ to react with $Br_2$ regardless of the temperature.

Another explanation could be that the very small temperature difference between 10 and 35 Celsius was not large enough to cause a measureable change (i.e. the difference was between 99.99 and 99.999% of the $H_2S$ reacting, etc.). A third explanation is the experimental set up not being capable of measuring a difference in rates due to limitations in its own precision.

A constant gas feed rate of 9.89 cc/min (8.10 cc/min for the 100% case) was used. Each $H_2S$ setting was used with both low and high $Br_2$ concentration solutions. The dilute solution contained 0.091 M $Br_2$ in 0.134 M HBr, and the concentrated solution contained 0.371 M $Br_2$ in 0.336 M HBr. For both these solution concentrations the rate coefficient was dependent on the amount of $H_2S$ being introduced into the reactor, not the concentration of bromine or HBr.

It is noted that at the more concentrated $H_2S$ gas streams not all $H_2S$ reacted. Assuming the 10% gas stream has 100% of all $H_2S$ reacted, the higher concentrated solutions only remove 95%, 81% and 76% of the $H_2S$ respectively. This can be attributed to the very brief residence time the $H_2S$ gas experienced in the above experiments as the 2nd reactor solution level was only ½" above the bottom of the gas sparger (dispersion tube). This effect is discussed further below.

Experiments were run with both the first and second reactor set ups to quantify the effect of residence time, mixing, and bromine concentration. The two setups are in FIG. 4-37 of U.S. Patent Application Ser. No. 61/646,576 incorporated by reference herein in its entirety.

A principal difference between the two setups is the residence time of the gas within the liquid. The second reactor has only ~½" of liquid above the outlet of the gas dispersion tube, whereas the first reactor column has ~6", resulting in significantly longer residence times for the $H_2S$ bubbles within the first reactor's $Br_2$ solution. Each system used the same fine-frit gas dispersion tube and the same conditions (gas flow rates, feed compositions, atmospheric pressure and ambient temperature of ~21° C.). Gas feed compositions of 10%, 35% and 70% $H_2S$ in $N_2$ balance at 9.89 cc/min, and 100% $H_2S$ at 8.10 cc/min were used. Two liquid solutions were made with low- and high-$Br_2$ concentrations (0.05 M and 0.28 M $Br_2$ in 0.33 M HBr respectively), and 100 ml of each solution was contained in each experimental run.

Instead of measuring when $H_2S$ appeared in the exiting gas stream, the color change of rector solution was used to determine when all bromine was consumed. This change occurs relatively quickly, and eliminates errors associated with the gas residence time between the reactor and GC, as well as time for the GC to examine each gas sample.

FIG. 4-38 of U.S. Patent Application Ser. No. 61/646,576 incorporated by reference herein in its entirety shows the rate of $Br_2$ consumption by the reaction versus percent composition of $H_2S$ in the feed gas for the 1st reactor column, the 2nd reactor with mixing, and the $2^{nd}$ reactor without mixing. Results were identical for both the low- and high-concentrated bromine solutions.

The red line in FIG. 4-38 of U.S. Patent Application Ser. No. 61/646,576 incorporated by reference herein in its entirety shows 100% of $H_2S$ being removed using the tall column used in the original experimental setup. This agrees with the initial GC results in which all $H_2S$ was removed for all conditions considered. The blue and green lines show the amount of $H_2S$ removed with the new short reactor with the mixer, turned on and off respectively.

At higher $H_2S$ concentrations the short reactor is unable to react with all $H_2S$ present, but there is an improvement when the mixer is turned on. This is hypothesized to occur due to entrainment of the bubbles in the solution, which results in an increased residence time in the solution. These results further confirm the reaction is mass transfer limited.

Example 3: Bench Scale $H_2S$ Removal from Sour-Gas

Natural gas is a complex mixture containing more than twenty compounds, but many of these compounds lie in classes such as alkanes and alkenes. Higher hydrocarbons are less soluble or insoluble in water, but are not necessarily inert in the presence of bromine. Systematic experiments were performed to understand how members of these classes react with bromine.

The experiments of Examples 1 and 2 above utilized a mixture of methane, hydrogen sulfide and nitrogen carrier gas. Later experiments added ethane and ethene, to determine if they react with bromine.

The objectives of this work was to identify undesirable reactions between bromine, hydrocarbons and sulfur, evaluate the effect of temperature, concentrations, pressure, and evaluate reaction of bromine with ammonia.

Initial work explored the amount of methane reacting in the following reaction:

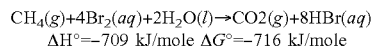
$$CH_4(g)+4Br_2(aq)+2H_2O(l) \rightarrow CO2(g)+8HBr(aq)$$
$$\Delta H°=-709 \text{ kJ/mole } \Delta G°=-716 \text{ kJ/mole} \qquad \text{Eq. 5-1}$$

As noted above, many other carbonated bromides are possible, but the above reaction is one in particular that thermodynamic equilibrium calculations predicts. It is expected that methane's limited solubility will allow it to pass through a dilute bromine-water solution unreacted so long as the temperature remains modest. However, $H_2S$, which is a hundred times more soluble than methane, is expected to react at the lower temperatures.

The experimental setup was the same as used for the $H_2S$ only work. There was no need to modify any of this equipment as it was designed and constructed from the beginning to be used for experimentation with methane and other hydrocarbons also. The only modifications involved the inclusion of additional source cylinders for the respective gases, and calibration of the GC to confirm that separation of each of the compounds of interest was reasonable.

Experiments were run incorporating methane into the reaction stream to see how $CH_4$ would affect the system. In one run, an 80 ml solution of 0.0754 M $Br_2$ and 0.3076 M HBr was put in the reactor. The total reactant gas flow rate was kept at 8.9 cc/min with 70% $CH_4$, 3% $H_2S$, 27% nitrogen, and the temperature was held at 30° C. (29.4-30.5° C.). The run lasted almost six hours.

The reaction solution began with a clear orange color, steadily lightened to yellow and then became clear, just as observed in the reactions without $CH_4$. GC data showed the same trends as before with the addition of methane.

Upon titration, the spent solution showed no detectable presence of $Br_2$, and the measured amount of HBr was within expectations. An initial $Br_2$ concentration of 0.0754 M should have yielded an HBr increase of 0.151 M, and an increase of 0.148 M was measured.

The $CH_4$ peak area ranged between 1.30-1.39 million throughout the reaction, which is the same as when run through the bypass line prior to reaction. No new peaks appeared in the GC chromatogram that would indicate a new gaseous species being formed, shown in FIG. 5-2 of U.S. Patent Application Ser. No. 61/646,576 incorporated by reference herein in its entirety. It is therefore concluded that $CH_4$ appears to be inert in this reaction at these conditions.

To start, the reaction gas mixture was run through the bypass line and GC chromatograms were obtained to confirm the initial gas concentrations. After obtaining consistent GC results, as shown in FIG. 5-1 of U.S. Patent Application Ser. No. 61/646,576 incorporated by reference herein in its entirety, the bypass line was switched to divert the reaction gas to the reactor.

Initially there was a small $H_2S$ bump. The reason for this is that, after pre-saturating the two water scrubbers, residual $H_2S$ gas remained in the inter-column lines. After approximately 2 hrs, all residual $H_2S$ in the inter-column lines disappeared from the GC chromatogram and no $H_2S$ was detected in the exhaust stream as shown in FIG. 5-2 of U.S. Patent Application Ser. No. 61/646,576 incorporated by reference herein in its entirety. At this point the $H_2S$ peak remained undetected for the duration of the reaction.

FIG. 5-3 of U.S. Patent Application Ser. No. 61/646,576 incorporated by reference herein in its entirety shows visually what the reactor column looked like during the above GC chromatograms. The solution lightened as bromine was consumed.

After 3.25 hrs from starting the reaction, all color from the reactor solution was gone (signifying the end of the reaction), with the exception of a small amount in the bottom where a stagnation region existed. Within another hour a small $H_2S$ bump appeared again in the GC chromatogram as shown in FIG. 5-4 of U.S. Patent Application Ser. No. 61/646,576 incorporated by reference herein in its entirety.

It took about an hour for the $H_2S$ bump to reappear after the reactor solution turned colorless This is attributed not only to lag time within the system (time gas takes to flow from the reactor to the GC) but also to the fact that the reactor solution began to dissolve $H_2S$ following consumption of the $Br_2$. The reactor solution did not initially contain any $H_2S$ so it could not begin to saturate itself with $H_2S$ until after all the $Br_2$ was consumed.

By 6 hrs, the red portion of reactor solution had turned colorless, and the $H_2S$ peak had returned to its original size as shown in FIG. 5-5 of U.S. Patent Application Ser. No. 61/646,576 incorporated by reference herein in its entirety.

FIG. 5-6 of U.S. Patent Application Ser. No. 61/646,576 incorporated by reference herein in its entirety shows visually what the reactor column looked like during the two GC chromatograms above. The solution turned clear as all bromine was converted to HBr.

As previously discussed, sour-natural gas typical contains higher hydrocarbons alongside methane. Ethane and ethylene, while accounting for much less than a percent of most sour-gases, are of particular interest since their reaction products can build up when large volumes of gas are treated. To start, it was verified that ethane ($C_2H_6$) and ethylene ($C_2H_4$) were detected with the gas chromatograph. FIG. 5-7 of U.S. Patent Application Ser. No. 61/646,576 incorporated by reference herein in its entirety shows the distinct peak of these two species along with water vapor, $H_2S$ and $N_2$. In this particular GC chromatogram the ethylene had been turned off and had already started decreasing.

To test for bromine reacting with ethane, a 19 cc/min stream of 50 vol % ethane in nitrogen (50/50 v/v) was flowed through the bypass line for several hours to reach a steady concentration and flush out older gases. The ethane GC peak area for the reactor inlet flow was 3.1 million.

An aqueous solution of $Br_2$ (0.379 mol/L) and HBr (0.384 mol/L) was made and 99 mL was added to the reactor at room temperature (24° C.). Upon starting reactor flow, the GC peak area began at 90,000 and steadily increased to 3.1 million after 1 hour. This peak area corresponds to the concentration of ethane in the sample as measured by the GC. There was no color change in the reactor solution to signal bromine being consumed. The GC peak starts lower because ethane is slightly soluble in water and some dissolves in the water before saturation allows all of it to pass through to the GC. The ethane GC peak area of 3.1 million was quickly established, and it is evident that ethane does not react with $Br_2$.

The above experiment was repeated with $H_2S$ to see if there were any changes to the $H_2S/Br_2$ reaction in the presence of ethane. After 2.4 hours the reactor and water column had turned clear, signifying that all $Br_2$ had been consumed. The reaction gas continued to be fed to the reactor until the GC area remained constant for $H_2S$. At this point, the reactor solution was titrated to obtain final concentrations which agreed with results obtained without ethane.

No new peaks were observed in the GC chromatograms during the course of the reaction, signifying that no new gaseous species were formed as a result of reaction with ethane. Also, the ethane peak area remained constant throughout the reaction, verifying further that ethane does not partake in this reaction.

Ethylene's ($C_2H_4$) reactivity with bromine was evaluated in several experiments where 40 cc/min of 50 vol % ethylene and 50 vol % $N_2$ at room temperature was passed through 100 mL of aqueous 0.5 M $Br_2$ and 2.13 M HBr.

FIG. 5-8 of U.S. Patent Application Ser. No. 61/646,576 incorporated by reference herein in its entirety shows the reactor from start to finish. It took ~2.5 hours to turn the solution completely clear, indicating consumption of all $Br_2$ (A=0 min, B=60 min, C=95 min, D=120 and E=145 min).

The exiting gas stream was analyzed with the gas chromatograph for ethylene content. FIG. 5-9 of U.S. Patent Application Ser. No. 61/646,576 incorporated by reference herein in its entirety shows the increase in $C_2H_4$ detected by the GC with respect to reaction time for two reaction runs. Initially no $C_2H_4$ passes through unreacted but as $Br_2$ is consumed, its concentration decreases, and more $C_2H_4$ goes through to the GC. Eventually when all bromine is gone as evidenced by the color change, all $C_2H_4$ passes through unreacted.

FIG. 5-10 of U.S. Patent Application Ser. No. 61/646,576 incorporated by reference herein in its entirety shows the post-reaction solution containing two separate phases, the heavier smaller one being of an oily consistency. The color of both phases started very pale yellow before becoming clear. The light phase is likely aqueous HBr, and the oily phase is 1,2-Dibromoethane ($C_2H_4Br_2$), also known as ethylene dibromide which is produced when $Br_2$ and ethylene react.

The formation of ethyl bromide ($C_2H_5Br$) from ethylene reacting with HBr is not considered feasible as it does not align with the GC results. After all the bromine was consumed and the solution turned clear ethylene passed through the reactor unaffected despite HBr still being present.

The fresh and spent reactor solutions from the ethylene-bromine reaction were analyzed by titration. The initial 100 mL reactor solution was 0.50 mol/L $Br_2$ and 2.23 mol/L HBr in water. The final solution contained no $Br_2$. It was expected that all $Br_2$ would be converted to ethylene dibromide, and this was confirmed by the HBr concentration only increasing to 2.25 mol/L. This is within the analyses range of error, but it is possible a small amount of water evaporated into the gas stream during the experiment, thereby increasing the HBr concentration by 1%.

Ethylene dibromide reacts with potassium iodide at elevated temperatures according to the following:

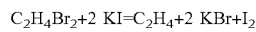

$$C_2H_4Br_2 + 2\ KI = C_2H_4 + 2\ KBr + I_2$$

Starch added to this solution turns purple if $I_2$ is present, thus indicating the presence of ethylene bromide. Titration of this solution with $Na_2S_2O_3$ determined the $I_2$ concentration and then the amount of ethylene bromide produced by the experiment which corresponded to the production of ethylene dibromide.

As predicted based on solubility, methane and ethane do not react with aqueous bromine solutions. Ethylene does react with aqueous bromine, but it is not present in significant quantities most sour-gases, and therefore should not prevent a process from operating.

Aqueous bromine/HBr solution can be used in a process to sweeten sour gases that will not react with the methane and ethane hydrocarbon component of the gas. It is expected that higher-hydrocarbons, especially ones with double-carbon bonds will react more readily with bromine. These species are not very common to most sour-gases, and will have to be evaluated in future work.

Example 4: Bench Scale Electrolysis of Hydrobromic Acid

The production of hydrobromic acid (HBr) from hydrogen sulfide ($H_2S$) oxidation is interesting, but irrelevant unless the bromine reactant can be regenerated. Bromine is expensive and its loss would make the proposed process uneconomical. Past work with small single-cell demonstrations show bromine can be recovered from the electrolytic decomposition of hydrobromic acid.

Hydrobromic acid electrolysis experiments were undertaken to provide more information relevant to the development of the two step hydrogen sulfide removal process. This work is novel because it utilized a 20 cell PEM stack rated at 10 kW of capacity. Prior results for PEM electrolyzers were derived from much smaller, single cell devices.

The objective of the present electrolysis tests was to confirm the operational cell voltages for different concentrations of hydrobromic acid at different current densities in a multi-cell electrolyzer stack. A secondary goal was to identify unexpected behavior that arises in scaling up to a 10 kW stack. The specific objectives were as follows:

Determine voltage versus current relationships for different HBr concentrations;
Measure the current efficiency;
Estimate the stack and cell internal resistance;
Evaluate effect of bromine concentration on HBr electrolysis voltage; and
Identify issues that may affect further scale up A hydrobromic acid PEM electrolyzer rated at 10 kW power was obtained for HBr electrolysis work. A similar 50 kW fuel cell stack is pictured in FIG. 6-1 of U.S. Patent Application Ser. No. 61/646,576 incorporated by reference herein in its entirety.

Initially the eight bolts holding the stack together were tightened to 25 ft-lbs torque. The two inlet ports (for HBr-rich electrolyte and carrier gas) were piped together, and its two outlet ports (for HBr-lean electrolyte and hydrogen) were also piped together to insure the two sides of the membrane would be at the same pressure. The stack was flushed with softened water to remove any debris. Ball valves were placed on the inlet and outlet pipes, and a pressure gauge and regulator were added to the outlet pipe. FIG. 6-2 of U.S. Patent Application Ser. No. 61/646,576 incorporated by reference herein in its entirety shows a schematic of the apparatus.

FIG. 6-3 of U.S. Patent Application Ser. No. 61/646,576 incorporated by reference herein in its entirety shows the connected stack. During electrochemical testing the electrolyzer is positioned vertically, but for the pressure tests shown in the figure it is set on its side.

After flushing the stack of debris and displacing any internal air that was present the inlet (water outlet) ball valve was closed and the internal pressure was raised to 10 psig using a 40 psig source. The outlet (water inlet) valve was closed, and the internal pressure was monitored as the stack was visually inspected for leaks. Some small leaks (weeping) occurred between the cells and so the stack bolts were tightened to 50 ft-lbs of torque. The stack was pressurized to 14 psig at which point more weeping was detected. The bolts were tightened to 70 ft-lbs, and the pressure was raised to 20 psig.

Over three hours the pressure dropped one psig. The pressure was lowered to 10 psig, and over 72 hours no pressure drop was detected. Testing was planned at no more than 5 psig, so the stack successfully passed its pressure test.

FIG. 6-4 of U.S. Patent Application Ser. No. 61/646,576 incorporated by reference herein in its entirety shows the small amount of weeping that occurred between two of the 20 cells at 20 psig internal pressure.

To verify the anolyte pump used in electrochemical testing was acceptable the pressure drop versus flowrate was determined. At a flow rate of 3 gallons per minute a back pressure of 2 psig developed in the stack. FIG. 6-5 of U.S. Patent Application Ser. No. 61/646,576 incorporated by reference herein in its entirety shows the results of these tests.

A test rig was designed to allow the safe testing of the HBr electrolyzer. A schematic is shown in FIG. 6-6 and the actual set up is shown in FIG. 6-7 of U.S. Patent Application Ser. No. 61/646,576 incorporated by reference herein in its entirety. The principal components include the electrolyzer stack, a source tank of HBr-rich anolyte, a receiving tank for HBr-lean catholyte, PURAFIL PURACARB® absorptive media, and a power supply. [Reference 84]. The absorptive media captures any fugitive bromine or HBr vapors, and the power supply is a rectifier that converts grid AC power to the DC power required by the electrolyzer.

The test stand is isolated from the surrounding environment to prevent exposure to bromine during the HBr electrolyzer tests. The area is enclosed in plastic and blowers are engaged to circulate the air surrounding the equipment through the absorptive media. The HBr tanks also vent to this absorptive media. FIG. 6-8 of U.S. Patent Application Ser. No. 61/646,576 incorporated by reference herein in its entirety shows the rectifier that provides power, and the blower that pulls air from the test set up and pushes it through the absorber (also pictured).

The equipment is connected through plastic PVDF pipes, and pumps are employed to circulate the liquids. HBr is introduced to the system from a 48 wt % HBr drum purchased from Albemarle chemical, and diluted with de-ionized water to the desired concentration.

Instrumentation in the form of voltage meters, current meters, temperature sensors, pressure gauges and flow meters collect data during testing. An Allen Bradley SLC500 microprocessor is used for process control and data logging.

FIG. 6-9 of U.S. Patent Application Ser. No. 61/646,576 incorporated by reference herein in its entirety depicts the assembled system with the tanks, pumps sensors, and other equipment used in the test system identified. This is a photo of the system during bromine generation, and the purplish coloration of the $HBr_3$ solution in the anolyte tank and PVDF piping is obvious.

After the set up was assembled and leak checked a predetermined set of conditions were analyzed. The results are presented below.

A set of runs were undertaken in which the electrolyzer was operated at fixed currents to determine the voltage characteristics as a function of current density for different HBr concentrations. The anolyte source tank was filled with 48 wt % HBr which was circulated through the system. The solution was passed through the electrolyzer at increasing amperage up to 480 amps (2.25 $kA/m^2$ current density) and then decreasing amperage at the same amperage values. The anolyte source HBr solution was diluted with softened water to obtain the HBr concentration desired in the next experimental runs.

Starting HBr weight concentrations of 43 wt %, 38.5 wt %, 30 wt %, 22 wt %, and 13 wt % were analyzed. The individual cell voltage in the electrolyzer stack (stack voltage/20 cells) as a function of the applied current density and HBr concentration for the entire set of runs is shown in FIG. 6-10 of U.S. Patent Application Ser. No. 61/646,576 incorporated by reference herein in its entirety. The 13 wt % HBr cell voltage at 0.25 kA/m$^2$ is thought to be a measurement error.

The results agree with expectations for the decomposition voltage increasing at lower HBr concentrations and higher current densities. Greater voltage for 43 wt % than 38.5 wt % or 30 wt % HBr at higher current densities is due to membrane dehydration. At high acid concentrations, there is less water in the membrane for proton transport, which causes an increase in the membrane resistance and resulting decomposition voltage.

FIG. 6-11 of U.S. Patent Application Ser. No. 61/646,576 incorporated by reference herein in its entirety shows the decomposition voltage at different HBr concentrations.

As theory suggests the voltage decreases at increased concentrations and lower current densities, while the rise in voltage for the highest 43 wt % HBr concentration can be explained by membrane dehydration increasing the cell resistance. The HBr cell voltages for an unoptimized electrolyzer with no catalyst are much lower than the 1.85 Volts required for water electrolysis.

FIG. 6-12 of U.S. Patent Application Ser. No. 61/646,576 incorporated by reference herein in its entirety shows the bromine current efficiency as a function of HBr concentration.

The bromine concentration in the initial HBr solution was kept low to minimize its effect on current efficiency. The 41.5 wt % HBr and 30 wt % HBr runs had current efficiencies of 94% and 92.4% respectively, and the 20 wt % and 16 wt % HBr runs had lower current efficiencies of 87.9% and 85.9% respectively.

Gas bubbles were visible in the electrolyzer outlet during the 16% and 20% HBr runs. The gas is most likely oxygen, which is a byproduct of competing water electrolysis at the carbon anodes at these lower HBr acid concentrations and relatively high 2 kW/m$^2$ current density.

An example current efficiency run shown in FIG. 6-13 of U.S. Patent Application Ser. No. 61/646,576 incorporated by reference herein in its entirety illustrates how the electrolyzer voltage and anolyte temperature increase during one bromine current efficiency run.

The temperature increases with time because power is being put into the electrolyzer to decompose HBr, and some of this manifests itself as heat. The required electrolysis voltage increases during the run due to a decrease in HBr concentration and increase in Br$_2$ concentration during the run which both work to decrease the current efficiency due to competing reactions to split water and reform HBr respectively.

FIG. 6-14 of U.S. Patent Application Ser. No. 61/646,576 incorporated by reference herein in its entirety shows the effect of anolyte bromine concentration on the electrolyzer bromine current efficiency (CE) at an operating current density of 2 kA/m$^2$.

These results came from a sequential series of batch runs with a starting concentration of 42 wt % HBr and 1.7 wt % Br$_2$. The anolyte solution was electrolyzed in four current efficiency runs. The first run ended with a solution of 12.5 wt % Br$_2$, and the last ended with 28 wt % Br$_2$. As can be seen from the graph, the bromine current efficiency decreased from ~94% to ~79%, which is significant, but understandable considering the large increase in final bromine concentration in the last run.

The effect of anolyte bromine concentration on current efficiency is important in defining the optimum conditions to operate the HBr/Br$_2$ electrolyzer in an energy storage system or other related applications, both of which are beyond the scope of this work.

The electrolyzer operated very well with no liquid leakage at up to 50 Celsius. As anticipated, increasing anolyte HBr concentration reduced the voltage, and increasing bromine concentration raised the voltage.

The 43 wt % HBr voltage versus current density scan did not have the lowest cell voltage as expected, and the slope did not run parallel to the other HBr solution concentration lines. This is likely the effect of membrane dehydration due to lower available water in the solution, which at 43 wt % HBr solution concentration may significantly decrease proton transport and increase cell voltage.

Decreasing HBr concentration from 42 wt % to 15 wt % reduced the current efficiency from 94% to 86%. Increasing the bromine concentration had a significant impact on the current efficiency, dropping it from 94% to 79% as bromine concentration went from 1.7 wt % to 28 wt %. Both of these appear reasonable at the high current density of 2 kW/m$^2$.

This voltage versus current density data can be compared with values in the literature that have depicted HBr cell voltage versus current density at various HBr concentrations. The test results obtained are similar to earlier referenced data. The slopes of the cell voltage versus current density data are steeper for the tested electrolyzer than the literature results, possibly a result of the increased resistance of the multi-cell stack, as well as it not being optimized nor loaded with any catalyst.

Important differences to consider in the literature values are temperature, current density, the presence/concentration of any bromine in the HBr solutions and the actual HBr concentrations. Most references do not provide enough information for direct data comparisons. It is likely the experimental electrolyzer voltage intercept (open circuit voltage) and slope (IR losses) can be reduced an additional 20-40% through membrane, electrode, and systems optimization work. Thus, further optimization of the stack should allow comparable voltages.

As shown in the preceding Examples, the bromination process has been shown to behave as anticipated, and is expected to be a viable method for treating H$_2$S. The major questions that require answers concern the economic and long term operational consequences of the process, neither of which were fully investigated in this research.

The following are the key findings from the preceding Examples:

Reaction between bromine and hydrogen sulfide occurs readily;

Sulfuric and hydrobromic acid are the products of the said reaction;

Methane and ethane do not react with hydrobromic acid;

Ethylene does react with aqueous bromine;

Hydrobromic acid can be electrolyzed at room temperature for less than 1 Volt; and Process economics appear favorable over existing H$_2$S treatment solutions.

The bromination process takes advantage of two thermodynamic shortcuts that reduce the energy and equipment cost required to treat H$_2$S and produce hydrogen compared to alternative methods.

First, at moderate temperatures and pressures the bromination of H$_2$S is fast with high HBr product yields, which allows rapid processing of $H_2S$. Second, the HBr bond is weak and is decomposed in a simple and robust electrolyzer for less energy than obtained from burning hydrogen with oxygen. These characteristics minimize the size of reaction equipment, and maximize the utilization of $H_2S$ and electricity.

Based on the experimental data and economic analysis, presented below, the potential benefits of the present bromination process are significant. All components for an integrated prototype, including PVDF bromination absorber columns and HBr electrolysis systems are commercially available. The next steps are to scale-up the process to an integrated demonstration, and run the process continuously with a simulated sour-gas source to allow greater quantification of the economic and environmental benefits and liabilities.

FIG. 8-1 of U.S. Patent Application Ser. No. 61/646,576 incorporated by reference herein in its entirety is illustrative of one prototype system in accordance with the present disclosure.

A wider range of conditions should be investigated, continuous operation for days at a time should be achieved, and greater attempts to analyze the scrubbing solution with liquid chromatography to detect the formation of new species should be performed.

Large quantities of industrial $H_2S$ are a burdensome byproduct waste from refineries, natural gas treatment plants, and waste water treatment plants. Dilute but significant $H_2S$ quantities are also produced in landfills and agricultural anaerobic digesters. Producing hydrogen from any $H_2S$ source, large or small could enhance the utilization of sour-(bio)gas resources, be financially rewarding, help transition towards a hydrogen economy, and benefit the environment.

The bromination process can reduce electricity production costs by allowing the exploitation of sour domestic natural gas reserves, reduce fuel consumption by displacing natural gas and other fuels with co-produced hydrogen, and reduce the environmental impacts of energy by eliminating hydrogen sulfide emissions. Some consequences of commercialization could include:

Increased revenue, profitability and/or reduce operating cost;
Reduced disposal liability and plant footprint;
Reduced fossil-fuel use, cost and dependence, increased sustainability; and
Reduced waste, greenhouse gas emissions and pollution.

The proposed process provides two important end-user benefits. First, it processes a negative-value, environmentally harmful feedstock into an essential chemical commodity, hydrogen, which is electrolytic quality or 99.999% pure and can be used without additional clean up in demanding applications such as polymer fuel cells, food processing, chip manufacture, and electric generator cooling among many other traditionally 'merchant' hydrogen demand categories.

Second, the process is potentially much more efficient, less-expensive and environmentally cleaner at producing hydrogen than established production processes, such as steam-methane-reforming and water electrolysis.

Example 5: Pilot Scale Process for Desulphurization and Hydrogen Recovery

Subsequent to the performance of the tests described above as disclosed in Applicant's Doctorate Dissertation entitled "METHOD FOR REMOVING HYDROGEN SULFIDE FROM SOUR GAS AND CONVERTING IT OT HYDROGEN AND SULFURIC ACID", by Melahn Parker, June 2010, work began on developing a pilot scale process for desulphurization and hydrogen recovery, as descried herinafter.

FIG. 1 is illustrative of one embodiment of a pilot scale process for desulphurization and hydrogen recovery 100 in accordance with the present invention. As illustrated in FIG. 1, the pilot scale process for desulphurization and hydrogen recovery 100 includes an $H_2S$ reactor column 40, having a sour gas influent stream 1, including an amount of a hydrocarbon gas, i.e., methane, an undesirable amount of hydrogen sulfide, and water vapor. In the illustrative embodiment of FIG. 1, a sour gas influent stream 1 enters the bottom of the $H_2S$ reactor column 40, and is contacted countercurrently with an aqueous reaction solution 15 comprising bromine and hydrogen bromide in solution, along with small amounts of hydrobromic acid and sulfuric acid. In at least one embodiment, a dilute aqueous hydrobromic acid solution 22 is introduced near the top of the rector column 40.

The bromine/hydrogen bromide in the aqueous reaction solution 15 reacts with the hydrogen sulfide in the sour gas influent 1 and forms an aqueous solution of hydrobromic acid, sulfuric acid, and an amount of solid sulfur which is discharged in an aqueous effluent stream 4 from the bottom of the column 40 and may be extracted from the solution 4, such as via a mechanical filter 50. It is noteworthy, as illustrated in the corresponding mass balance in FIG. 2, essentially all of the methane present in the sour gas influent 1 passes through the $H_2S$ reactor column 40 unreacted, and is present in a gaseous effluent stream 2 of the $H_2S$ reactor column 40, along with amounts of carbon dioxide, hydrogen bromide, and water vapor.

As shown in FIG. 1, a first HBr absorber 70 is employed to remove and recover a first amount of a dilute aqueous hydrobromic acid solution 21 for subsequent recirculation back to the $H_2S$ reactor column 40 via solution 22. A water makeup stream may be introduced into the first HBr absorber 70, as well as a second HBr absorber 80, once again, as demonstrated in the illustrative embodiment of FIG. 1.

The effluent stream 6 of the $H_2S$ reactor column 40, following filtration, is further treated via a condenser/evaporator array 60, before transfer to an HBr storage tank 65, once again, as shown in the embodiment of FIG. 1. The hydrobromic acid solution from the HBr storage tank 65 is processed through an electrolyzer 90, resulting in a disassociation of hydrogen gas 16 and water vapor, along with negligible amounts of hydrobromic acid, which is further processed via a second HBr absorber 80. In at least one embodiment, the second HBr absorber 80 comprises a solid absorbant-dessicant 84 in a packed column 82, and in one further embodiment, the gas effluent 17 of the second HBr absorber 80 is further processed via a hydrogen cooler 86 and drier 88.

In at least one embodiment, electrolyzer 90 comprises at least one proton exchange membrane cell 94, and in one further embodiment, the electrolyzer 90 comprises a plurality of proton exchange membrane cells 94. In yet one further embodiment, the electrolyzer 90 comprises a plurality of proton exchange membrane cells 94 disposed in a series configuration in an electrolyzer stack 92. The electrolyzer stack 92 further results in the production of bromine and hydrogen bromide from the hydrobromic acid, which is then stored in solution in the HBr—$Br_2$ Storage tank 66, and is subsequently pumped back to the H$_2$S reactor column 40 as aqueous reaction solution comprising an amount of bromine 15.

As readily seen from FIG. 1, the present inventive process is utilized to remove hydrogen sulfide from a sour gas influent 1, via reaction with an amount of bromine/hydrogen bromide in an aqueous reaction solution 15, producing a substantially clean methane effluent stream 3, and a solid sulfur 5/sulfuric acid 8 side stream, while requiring only the addition of some makeup water to the process, such as, for example, where indicated in FIG. 1. A further significant benefit for the present inventive process 100 is the production of hydrogen gas 16/17 as a result of processing the hydrobromic acid/sulfuric acid solution via electrolyzer stack 92.

As noted above, FIG. 2 provides mass balances corresponding to the pilot scale process for desulphurization and hydrogen recovery 100 as presented in the illustrative embodiment of FIG. 1, based on a computer simulation of the operation of the same.

Economic Evaluation

Many of the components required for the bromination process are available off the shelf, or have well known industry cost estimates. This allows an estimation of the economics for a commercial implementation of the proposed bromination process. The financial feasibility of the process is based on a revenue minus cost analysis to determine the charge or income received to sweeten a stream of sour gas. Capital costs are estimated from equipment prices, and operating costs are calculated from what the process consumes and reasonable maintenance factors for similar equipment. Revenue comes from the sulfuric acid and hydrogen byproduct of the gas sweetening process.

Typical natural gas wells can produce from 10 thousand to 15 million scf of gas a day. A common production profile may be 1 million scf initially that reduces within a few years to a hundred thousand scf a day for the next decade. [Reference 85]. Sour-gas content varies greatly between different wells: values of a few percent are common in developed natural gas resources, 3-15 vol % is common from oil production associated gas, and some wells in Texas and the Middle East can have over 80% H$_2$S content. [Reference 86]. A 4 vol % H$_2$S sour-gas stream of 100 thousand standard cubic feet per day (scf/d) is taken as the baseline gas stream for sweetening. Many wells of this size and H$_2$S content are found in North America and are of particular interest because they are often not produced due to their H$_2$S content. [Reference 87]. The bromination process may be first adopted at these smaller wells where much larger modified-Claus process sulfur plants or H$_2$S corrosion resistant transmission pipelines are too expensive to be installed.

To simplifying the economic analysis, the baseline plant treats 100% of the incoming H$_2$S stream with the only other constituent being methane. In actual practice higher hydrocarbons will be present that may react with bromine and need to be removed from the system as they accumulate. The financial viability is presented as the cost to treat a MMBtu of natural gas which is converted to a cost per kg of H$_2$S removed for comparison with alternative methods. For our assumed 4 vol % H$_2$S gas stream in methane, 1.7 kg of H$_2$S is present with each MMBtu of methane.

A baseline system to clean 100 thousand standard cubic feet per day (~23 normal cubic meters per day) sour-natural gas with 4 vol % H$_2$S content costs 12 cents per MMBtu of cleaned gas or 7 cents per kg of H$_2$S removed. [Reference 88]. The installed system is projected to cost ~$79 k with material and subsystem costs accounting for ~$40 k of the turn-key cost. The annual operating costs are ~$25 k per year, and revenues of ~$33 k per year may be obtained from the sale of hydrogen and sulfuric acid.

The baseline system produces 96 kg of hydrogen a day and requires a 114 kW electrolyzer. Different revenue scenarios are evaluated, and sensitivities to the range of assumptions are assessed to estimate the cost to clean a range of sour gas streams. The process economics are heavily dependent on assumptions regarding the price of hydrogen and concentration of H$_2$S in the gas stream, thus these assumptions are evaluated further.

The system component costs come from standard industry relations for common equipment such as power transformers and absorption columns, and forecasts for future costs of newer equipment such as electrolyzers and hydrogen purification equipment. [Reference 89]. Table 7-1 shows equipment and subsystem cost estimates.

The values are an estimate for what equipment will cost when low-rate manufacturing of ~5 units a month is achieved. The major pieces of equipment are described above, and many smaller pieces are not identified separately, but are lumped together under their respective subsystems. All prices are quoted in a metric related to the equipment's size which can be related to the total gas flow rate, the amount of H$_2$S, or the power required. The component cost breakdown for the baseline system is shown in FIG. 7-1 of U.S. Patent Application Ser. No. 61/646,576 incorporated by reference herein in its entirety.

Equipment costs do not include the assembly, installation, manufacturer margin and other costs that must be covered in the purchase price. It is assumed that $1 million will need to be invested to develop a production unit. Much of this may not be paid back if it comes in the form of grants or cost shared agreements, but for this analysis it is assumed to be amortized over 200 units. These additional costs are shown in Table 7-2. [References 90, 91].

FIG. 7-2 of U.S. Patent Application Ser. No. 61/646,576 incorporated by reference herein in its entirety shows the total purchase price, estimated to be $78,870, for a turn-key system.

A discounted cash flow method determines the income necessary to generate the required returns on the capital investment. Assumptions on weighted average cost of capital (WACC), utilization and lifetime allow the purchase price to be allocated over the services performed. Table 7-3 shows these assumptions.

The annual capital payment is calculated to be $11,229 per year from Equation 7.1.

This allows the purchase price to be paid back with interest. When the facility capacity and utilization are taken into account a charge of $0.36 per MMBtu of gas is required to pay for the purchase of the equipment alone. Equation 7.1 used Equation 7.2.

Electricity for HBr electrolysis is the dominant operational cost followed by heat for concentrating sulfuric acid, electricity for H$_2$ compression and the solution pumps, maintenance of the capital equipment, and bromine replacement. Table 7-4 shows the assumptions used for these calculations.

HBr is electrolyzed at 0.9 Volts with electricity from a 95% efficient AC/DC converter. Approximately 10 kWh is required to concentrate the sulfuric acid product, but a lot of heat is released by the bromination reaction, so it is assumed that only 2 kWh of high temperature heat is required to reach the final concentration of 70 wt % H$_2$SO$_4$.

In practice, a trade off will occur between the heat required to concentrate sulfuric acid, and the cost to transport less concentrated sulfuric acid and replace the bromine content removed from the process with the sulfuric acid product. If sweetened natural gas is used to run a generator for the electricity required, there will be some waste heat available that could further reduce the amount of heat required.

FIG. 7-2 of U.S. Patent Application Ser. No. 61/646,576 incorporated by reference herein in its entirety shows the operational cost breakdown for the baseline system. A total annual cost of $25,381 is projected, of which 84% are variable costs. When capital costs are included, variable costs account for 59% of total costs.

Electricity for regenerating bromine reagent and producing hydrogen is the dominant operational cost. The electricity price of 4.3 cents per kWh is justified through the use of a natural gas generator at the well site that operates on part of the sweetened natural gas stream. These generators are relatively inexpensive and common, but their capital cost is not included because the electric power could also come from alternate sources. [Reference 92]. The electricity cost is based on the revenue lost from not selling the gas at its assumed price of $5 per MMBtu, and operating the generator at 40% efficiency.

Revenue for the process comes from the sale of hydrogen and sulfuric acid. The baseline uses values of $2 per kg of hydrogen and $50 per tonne of $H_2SO_4$. The price for these chemicals is heavily dependent on where they are, and the quantities available. The price for hydrogen is equivalent to the cost to produce a kilogram of hydrogen from natural gas at $5 per MMBtu using Steam Methane Reforming as shown in FIG. 2-11 of U.S. Patent Application Ser. No. 61/646,576 incorporated by reference herein in its entirety. The sulfuric acid value is approximately half of its current value. [Reference 93].

Small amounts of sulfuric acid less than 10 tonnes may not prove commercially viable to ship to market. In such situations alternate uses of the acid, such as converting it to more valuable iron sulfate fertilizer or using it in local water treatment applications can occur.

FIG. 7-4 of U.S. Patent Application Ser. No. 61/646,576 incorporated by reference herein in its entirety shows the revenue available to the baseline system depending on the hydrogen and sulfuric acid sale price. It is evident from the chart that the price of hydrogen has a much larger impact on revenue than the price of sulfuric acid.

At a minimum, hydrogen can be given price of $0.57 per kg based on the energetic value of natural gas at $5 per MMBtu since it can be mixed back in with the sweetened gas. Doing this would reduce the capital costs $10,000 by eliminating the need for hydrogen drying, compression, and storage.

At a maximum, hydrogen may be valued at $4 to $6 per kg, which is a price hydrogen distributors are willing to pay for "green" hydrogen. [Reference 94]. The hydrogen produced in the bromination process may be considered "green" by using renewable electricity for the electrolysis and because the hydrogen comes from what would normally be a waste.

The prices assumed for hydrogen do not take into account any "green" credit, but this could be an option depending on the specific implementation. By avoiding the need to remove $H_2S$ from the sour gas in an amine plant, and convert to sulfur in a modified-Claus plant, there may be a carbon abatement opportunity.

Economic estimates are reasonable for the proposed process considering the small size of its implementation (100 kscf), but heavily dependent on $H_2$ and sulfuric acid revenue. FIG. 7-5 of U.S. Patent Application Ser. No. 61/646, 576 incorporated by reference herein in its entirety shows the cost to sweeten a MMBTu of sour-gas and remove a kg of $H_2S$. Throughout this section net costs are presented as positive values. If a profit occurs from sweetening due to hydrogen and sulfuric acid revenue, it is shown as a negative value.

The process is estimated to sweeten 4 vol % $H_2S$ sour-gas for approximately 12 per MMBtu of natural gas produced or 7¢ per kg of $H_2S$ removed. This is very competitive with large scale amine and modified-Claus process systems, but much less than competing small scale solutions. If no revenue came from hydrogen or sulfuric acid the costs would be $1.18 per MMBtu and 68 ¢ per kg of $H_2S$ removed.

As previously discussed, an amine system alone for a 250 kscf per day 0.6 vol % $H_2S$ well can cost $2.3 per kg of $H_2S$ removed, and an accompanying modified-Claus plant can cost over 70 ¢ per kg of $H_2S$ treated.

The cost of other $H_2S$ removal methods is largely dependent on the sacrificial material used, but is approximately $2-6 per kg of $H_2S$ removed. [Reference 95]. The higher end of this range is for scavenger methods intended for gases with very low $H_2S$ concentrations and very simple implementations. To avoid an unfair comparison the baseline system economics are estimated for very low $H_2S$ concentrations in the sensitivities section.

The baseline plant economic assumptions are varied around sensitivities for the $H_2S$ content of the gas stream, the capital cost of the installation, and the fixed maintenance costs, along with the electricity, hydrogen and sulfuric acid price. High and low values are selected to cover the extremes of what may be expected and are shown in Table 7-5.

FIG. 7-6 of U.S. Patent Application Ser. No. 61/646,576 incorporated by reference herein in its entirety shows the impact of the above values on the final cost to sweeten the sour gas.

Capital cost, electricity price, and hydrogen sale price have the greatest effect on the processes economics, and at the higher range of values assumed, the process becomes profitable. Specific assumptions are varied further to understand their impact. FIG. 7-7 of U.S. Patent Application Ser. No. 61/646,576 incorporated by reference herein in its entirety shows the sweetening cost versus $H_2S$ content of the sour gas and hydrogen price.

Significant revenue from hydrogen and sulfuric acid favors higher $H_2S$ concentrations in the gas stream because it leads to greater production of these byproducts. When the hydrogen price is less than $2 per kg its revenue is not enough to overcome the variable costs and the process becomes more expensive at higher $H_2S$ concentrations.

FIG. 7-8 of U.S. Patent Application Ser. No. 61/646,576 incorporated by reference herein in its entirety shows the impact of electricity and hydrogen price on the sweetening cost. Electricity is the dominant cost and has a big part in making the process expensive, but by selling hydrogen at higher prices the process can still break even at much higher electricity prices. On the other hand if cheap power is available from excess wind generation for instance, the process can more easily turn a profit while being less impacted by the $H_2S$ content of the sour-gas stream.

FIG. 7-9 of U.S. Patent Application Ser. No. 61/646,576 incorporated by reference herein in its entirety provides a map of the hydrogen versus electricity price tradeoff with the process, illustrating lower electricity prices leading to less expensive hydrogen.

The baseline plant capital costs and variable costs are 31% and 59% of the annual costs, respectively. As scale or capacity increase the costs will shift further to the operating cost of electricity due to economies of scale reducing the cost of larger capacity installations on a per unit of capacity basis.

Despite 59% of the baseline bromination process costs being variable costs (electricity, heat, bromine), there are significant benefits from increasing the scale of an installation, especially at low $H_2S$ concentrations when variable costs are relatively low. Equation 7.3 is used to account for scale effects.

Table 7-6 shows the economy of scale exponentials or "scaling factors" used. Equipment with large scale benefits receives a 0.6 factor, electrolyzers receive a 0.9 factor due to limited economy of scale benefits, and some equipment does not receive any benefit.

FIG. 7-10 of U.S. Patent Application Ser. No. 61/646,576 incorporated by reference herein in its entirety shows how the sweetening costs decrease as the plant capacity increases.

FIG. 7-11 of U.S. Patent Application Ser. No. 61/646,576 incorporated by reference herein in its entirety shows the cost to remove a kilogram of $H_2S$ for different $H_2S$ concentrations and gas stream volumes. The economics are better for higher $H_2S$ concentrations, but costs are still competitive for dilute $H_2S$ gas streams at large implementations.

FIG. 7-12 of U.S. Patent Application Ser. No. 61/646,576 incorporated by reference herein in its entirety presents the cost to sweeten different sour gas stream $H_2S$ concentrations and volumes which ranges from a 10 per MMBtu profit or loss for the samples considered. In all cases the costs appear reasonable when compared to a sweetened natural gas value of $5 per MMBtu. As a reminder the amine plant example from chapter 2 cost 58 ¢ per MMBtu with the modified-Claus plant adding an extra 15 ¢ per MMBtu to the removal and treatment of $H_2S$.

At 200 thousand scf per day of 4 vol % $H_2S$ sour-natural gas and a $2 per kg hydrogen price the sweetening process is able to break even. Higher hydrogen prices and $H_2S$ concentrations will make the bromination process more profitable, but the electricity price must align with the hydrogen price to avoid a significant penalty for essentially converting electricity into hydrogen.

Tables

TABLE 2-1

Typical constituents of various sour gases

| Parameter | Unit | Alberta Sour-well | Tunisia Sour-well | Biogas | Coal-bed Methane | Landfill |
|---|---|---|---|---|---|---|
| Hydrogen Sulfide | Vol % | 3.3 | 0.092 | 0.1-3 | 0.001 | 0.1 |
| Methane | Vol % | 77.1 | 96.91 | 63 | 95 | 45 |
| Carbon Dioxide | Vol % | 1.7 | 0.82 | 37 | 3 | 40 |
| Nitrogen | Vol % | 3.2 | 0.68 | 0.2 | 2 | 15 |
| Oxygen | Vol % | — | | — | | 1 |
| Ammonia | Vol % | — | | 0.1 | | 0.0005 |
| Hydrogen | Vol % | — | | — | | 0-3 |
| Higher Hydrocarbons | Vol % | 14.7 | 1.59 | — | | — |

TABLE 3-1

Concentrations of aqueous solutions of $Br_2$, HBr and $H_2SO_4$

| $Br_2$ | | | | HBr | | | | $H_2SO_4$ | | | |
|---|---|---|---|---|---|---|---|---|---|---|---|
| Molality $m_{Br2}$ mol/kg | Molarity $M_{Br2}$ mol/liter | mol % $X_{Br2}$ mol/mol | wt % $x_{Br2}$ kg/kg | Molality $m_{HBr}$ mol/kg | Molarity $M_{HBr}$ mol/liter | mol % $X_{HBr}$ mol/mol | wt % $x_{HBr}$ kg/kg | Molality $m_{H2SO4}$ mol/kg | Molarity $M_{H2SO4}$ mol/liter | mol % $X_{H2SO4}$ mol/mol | wt % $x_{H2SO4}$ kg/kg |
| 0.01 | 0.010 | 0.02% | 0.16% | 0.1 | 0.099 | 0.18% | 0.80% | 0.1 | 0.099 | 0.18% | 0.97% |
| 0.05 | 0.050 | 0.09% | 0.79% | 0.2 | 0.198 | 0.36% | 1.59% | 0.2 | 0.197 | 0.36% | 1.92% |
| 0.1 | 0.099 | 0.18% | 1.57% | 0.5 | 0.489 | 0.89% | 3.89% | 0.5 | 0.486 | 0.89% | 4.67% |
| 0.2 | 0.198 | 0.36% | 3.10% | 1 | 0.960 | 1.77% | 7.49% | 1 | 0.948 | 1.77% | 8.93% |
| 0.5 | 0.487 | 0.89% | 7.40% | 2 | 1.848 | 3.48% | 13.93% | 1.5 | 1.39 | 2.63% | 12.83% |
| 1 | 0.949 | 1.77% | 13.78% | 3 | 2.672 | 5.13% | 19.53% | 2 | 1.80 | 3.48% | 16.40% |
| 1.5 | 1.39 | 2.63% | 19.34% | 4 | 3.440 | 6.72% | 24.45% | 3 | 2.58 | 5.13% | 22.73% |
| 2 | 1.81 | 3.48% | 24.22% | 5 | 4.156 | 8.26% | 28.80% | 4 | 3.29 | 6.72% | 28.18% |
| 3 | 2.59 | 5.13% | 32.41% | 7 | 5.454 | 11.20% | 36.16% | 5 | 3.94 | 8.26% | 32.90% |
| 4 | 3.31 | 6.72% | 39.00% | 9 | 6.599 | 13.95% | 42.14% | 6 | 4.54 | 9.75% | 37.05% |
| 5 | 3.97 | 8.26% | 44.41% | 11 | 7.62 | 16.54% | 47.09% | 7 | 5.09 | 11.20% | 40.71% |
| Pure | 19.43 | 100% | 100% | Azeo. | 7.83 | 17.11% | 48.11% | Azeo. | 18.20 | 91.67% | 98.36% |

TABLE 3-2

Concentration of aqueous mixtures of $Br_2$, HBr and $H_2SO_4$

| Br₂ | | | | HBr | | | | H₂SO₄ | | | | H₂O | | | |
|---|---|---|---|---|---|---|---|---|---|---|---|---|---|---|---|
| Molality $m_{Br2}$ mol/kg | Molality $M_{Br2}$ mol/L | mol % $X_{Br2}$ mol/mol | wt % $x_{Br2}$ kg/kg | Molality $m_{HBr}$ mol/kg | Molality $M_{HBr}$ mol/L | mol % $X_{HBr}$ mol/mol | wt% $x_{HBr}$ kg/kg | Molality $m_{H2SO4}$ mol/kg | Molality $M_{H2SO4}$ mol/L | mol % $X_{H2SO4}$ mol/mol | wt % $x_{H2SO4}$ kg/kg | Molality $M_{H2O}$ mol/L | mol % $X_{H2O}$ mol/mol | wt % $x_{H2O}$ kg/kg | all density g/cc |
| 0.1 | 0.10 | 0.17% | 1.3% | 1 | 0.97 | 1.7% | 6.8% | 1 | 0.97 | 1.7% | 8.2% | 54.07 | 96.4% | 83.7% | 1.164 |
| 1.0 | 1.03 | 1.71% | 11.9% | 1 | 1.03 | 1.7% | 6.0% | 1 | 1.03 | 1.7% | 7.3% | 56.91 | 94.9% | 74.7% | 1.373 |
| 0.1 | 0.09 | 0.16% | 1.0% | 6 | 5.17 | 9.6% | 30.3% | 1 | 0.86 | 1.6% | 6.1% | 47.84 | 88.7% | 62.5% | 1.379 |
| 1.0 | 0.87 | 1.57% | 9.2% | 6 | 5.23 | 9.4% | 27.8% | 1 | 0.87 | 1.6% | 5.6% | 48.43 | 87.4% | 57.4% | 1.521 |
| 0.1 | 0.07 | 0.15% | 0.8% | 12 | 8.78 | 17.5% | 46.6% | 1 | 0.73 | 1.5% | 4.7% | 40.63 | 80.9% | 48.0% | 1.526 |
| 1.0 | 0.73 | 1.44% | 7.2% | 12 | 8.77 | 17.3% | 43.6% | 1 | 0.73 | 1.4% | 4.4% | 40.55 | 79.9% | 44.9% | 1.628 |
| 0.1 | 0.09 | 0.16% | 1.1% | 1 | 0.87 | 1.6% | 5.4% | 4 | 3.49 | 6.6% | 26.3% | 48.36 | 91.6% | 67.2% | 1.298 |
| 1.0 | 0.89 | 1.63% | 9.8% | 1 | 0.89 | 1.6% | 5.0% | 4 | 3.57 | 6.5% | 24.0% | 49.52 | 90.2% | 61.2% | 1.457 |
| 0.1 | 0.08 | 0.15% | 0.8% | 6 | 4.59 | 9.1% | 25.6% | 4 | 3.06 | 6.1% | 20.7% | 42.51 | 84.6% | 52.8% | 1.450 |
| 1.0 | 0.77 | 1.50% | 7.8% | 6 | 4.61 | 9.0% | 23.8% | 4 | 3.08 | 6.0% | 19.3% | 42.69 | 83.5% | 49.1% | 1.567 |
| 0.1 | 0.07 | 0.14% | 0.7% | 12 | 7.89 | 16.8% | 40.8% | 4 | 2.63 | 5.6% | 16.5% | 36.51 | 77.5% | 42.0% | 1.565 |
| 1.0 | 0.66 | 1.38% | 6.3% | 12 | 7.86 | 16.5% | 38.5% | 4 | 2.62 | 5.5% | 15.5% | 36.36 | 76.6% | 39.6% | 1.653 |
| 0.1 | 0.07 | 0.15% | 0.8% | 1 | 0.72 | 1.5% | 4.1% | 9 | 6.51 | 13.7% | 44.6% | 40.15 | 84.6% | 50.5% | 1.432 |
| 1.0 | 0.73 | 1.50% | 7.5% | 1 | 0.73 | 1.5% | 3.8% | 9 | 6.55 | 13.5% | 41.6% | 40.40 | 83.5% | 47.1% | 1.545 |
| 0.1 | 0.06 | 0.14% | 0.7% | 6 | 3.85 | 8.5% | 20.4% | 9 | 5.78 | 12.7% | 37.0% | 35.63 | 78.6% | 41.9% | 1.530 |
| 1.0 | 0.64 | 1.40% | 6.3% | 6 | 3.85 | 8.4% | 19.2% | 9 | 5.77 | 12.6% | 34.9% | 35.57 | 77.6% | 39.6% | 1.620 |
| 0.1 | 0.06 | 0.13% | 0.6% | 12 | 6.74 | 15.7% | 33.8% | 9 | 5.06 | 11.7% | 30.8% | 31.18 | 72.5% | 34.8% | 1.612 |
| 1.0 | 0.56 | 1.29% | 5.3% | 12 | 6.70 | 15.5% | 32.2% | 9 | 5.03 | 11.6% | 29.3% | 31.01 | 71.6% | 33.2% | 1.683 |

TABLE 3-3

Species considered in thermodynamic calculation

| GASEOUS | GASEOUS | AQUEOUS | AQUEOUS | AQUEOUS | AQUEOUS |
|---|---|---|---|---|---|
| Br(g) | OBrO(g) | Br(-a) | $H_2S_2O_3$(a) | $O_2$(-2a) | $S_3O_3$(-2a) |
| $Br_2$(g) | OH(g) | $Br_3$(-a) | $H_2S_2O_4$(a) | $O_2$(-3a) | $S_3O_6$(-2a) |
| BrBrO(g) | S(g) | $Br_5$(-a) | $HSO_3$(-a) | OH(a) | $S_4O_3$(-2a) |
| BrO(g) | $S_2$(g) | BrO(a) | $HSO_4$(-a) | OH(-a) | $S_4O_6$(-2a) |
| $BrO_3$(g) | $S_3$(g) | BrO(-a) | $HSO_5$(-a) | S(-2a) | $S_5O_3$(-2a) |
| BrOBr(g) | $S_4$(g) | $BrO_3$(-a) | HS2O3(-a) | $S_2$(-2a) | $S_5O_6$(-2a) |
| BrOO(g) | $S_5$(g) | $BrO_4$(-a) | HS2O4(-a) | $S_3$(-2a) | $S_6O_3$(-2a) |
| H(g) | $S_6$(g) | $H_2$(a) | HS2O5(-a) | $S_4$(-2a) | $S_6O_6$(-2a) |
| $H_2$(g) | $S_7$(g) | H(+a) | HS2O6(-a) | $S_5$(-2a) | $S_7O_3$(-2a) |
| HBr(g) | $S_8$(g) | HBrO(a) | HS2O7(-a) | $S_6$(-2a) | $S_7O_6$(-2a) |
| $HO_2$(g) | $SBr_2$(g) | $H_2O_2$(a) | HS2O8(-a) | $SO_2$(a) | PURE |
| $H_2O$(g) | $S_2Br_2$(g) | $HO_2$(-a) | HS3O3(-a) | $SO_3$(a) | H2SO4 |
| $H_2O_2$(g) | SO(g) | $H_2S$(a) | HS4O3(-a) | $SO_3$(-2a) | $H_2SO_4*H_2O$ |
| HS(g) | $SO_2$(g) | HS(-a) | HS5O3(-a) | $SO_4$(-2a) | $H_2SO_4*2H_2O$ |
| $H_2S$(g) | $SO_3$(g) | $HS_2$(-a) | HS6O3(-a) | $S_2O_3$(-2a) | $H_2SO_4*3H_2O$ |
| $H_2S_2$(g) | $S_2O$(g) | $HS_3$(-a) | HS7O3(-a) | $S_2O_4$(-2a) | $H_2SO_4*4H_2O$ |
| $H_2SO_4$(g) | $SOBr_2$(g) | $HS_4$(-a) | $O_2$(a) | $S_2O_5$(-2a) | $H_2SO_4*6.5H_2O$ |
| O(g) | | AQUEOUS | $HS_5$(-a) | $O_3$(a) | Br |
| $O_2$(g) | | $H_2O$ | $HS_6$(-a) | O(-a) | $Br_2$ |
| $O_3$(g) | | $Br_2$(a) | $H_2SO_3$(a) | $O_2$(-a) | S |
| | | | | $S_2O_7$(-2a) | |
| | | | | $S_2O_8$(-2a) | |

TABLE 4-1

HBr titration results

| Sample | Expected HBr | Calculated HBr | % error |
|---|---|---|---|
| 1 | 7.83M (48.1 wt %) | 7.76M (47.8 wt %) | 0.6% |
| 2 | 7.83M (48.1 wt %) | 7.81M (48.0 wt %) | 0.2% |
| 3 | 7.83M (48.1 wt %) | 7.71M (47.5 wt %) | 1.2% |

TABLE 4-2

$Br_2$ titration results

| Sample | Expected $Br_2$ | Calculated $Br_2$ | % error |
|---|---|---|---|
| 1 | 0.155M (2.44 wt %) | 0.149M (2.35 wt %) | 1.1% |
| 2 | 0.155M (2.44 wt %) | 0.157M (2.47 wt %) | 3.8% |
| 3 | 0.155M (2.44 wt %) | 0.151M (2.38 wt %) | 2.5% |

TABLE 4-3

HBr and Br$_2$ titration results

| Sample | Expected Br$_2$ | Calculated Br$_2$ | % error | Expected HBr | Calculated HBr | % error |
|---|---|---|---|---|---|---|
| 1 | 0.345 M | 0.330 M | 4.3% | 0.209 M | 0.215 M | 2.9% |
| 2 | 0.345 M | 0.342 M | 0.7% | 0.209 M | 0.221 M | 5.7% |
| 3 | 0.345 M | 0.336 M | 2.6% | 0.209 M | 0.209 M | 0% |

TABLE 4-4

Additional HBr and Br$_2$ titration results

| Sample | Expected Concentration | Titrated Concentration | % Error |
|---|---|---|---|
| Br$_2$ | 0.039M | 0.039M | 0.4% |
| Br$_2$ | 0.097M | 0.102M | 4.6% |
| HBr | 0.707M | 0.731M | 3.3% |
| HBr | 1.767M | 1.795M | 1.5% |
| HBr | 8.836M | 8.932M | 1.1% |

TABLE 4-5

Rate coefficient vs. temperature and H$_2$S concentration

| | Rate Coefficient k (mol/L · s) | | | |
|---|---|---|---|---|
| Temperature | 10% H$_2$S | 35% H$_2$S | 70% H$_2$S | 100% H$_2$S |
| 10/21/35° C. | $1.5 \times 10^{-5}$ | $5.0 \times 10^{-5}$ | $8.5 \times 10^{-5}$ | $9.3 \times 10^{-5}$ |

TABLE 7-1

Material cost assumptions

| Equipment | Cost | Unit |
|---|---|---|
| HBr electrolysis stack | $300 | $/kW |
| Power conversion (DC/AC rectifier) | $120 | $/kW |
| Sour-gas absorption column | $50 | $/kscf gas/day |
| Water scrubber | $25 | $/kscf gas/day |
| Sulfuric acid distillation column | $10 | $/kg H$_2$S/day |
| Fluid management (pumps and pipes) | $20 | $/kg H$_2$S/day |
| H$_2$ drier and compressor | $60 | $/kg H$_2$/day |
| H$_2$ storage tank (2,500 psi) | $80 | $/kg H$_2$/day |
| Br$_2$/HBr storage system (incl. Br$_2$/HBr) | $7 | $/kg Br$_2$ |
| Instrumentation and Controls | $2,000 | $/unit |
| Structure | $500 | $/unit |

TABLE 7-2

Installed cost assumptions

| Additional costs | Value | Unit |
|---|---|---|
| Assembly and installation (mostly Labor) | 40% | % of Material[1] |
| SG&A (Overhead) | 25% | % of Material |
| R&D amortized | $5,000 | $/unit[2] |
| Margin | 20% | % of Material |

[1] Material refers to the total equipment costs in prior table
[2] Assume $1 million in R&D expense is allocated over 200 units

TABLE 7-3

Annualized capital cost assumptions

| Assumption | Value | Unit |
|---|---|---|
| Lifetime | 10 | Years |
| Interest rate (WACC) | 7% | % |
| Utilization | 90% | % of year |

TABLE 7-4

Annualized capital cost assumptions

| Item | Value | Unit |
|---|---|---|
| Maintenance, Labor | 5% | % of Capex |
| Electricity - electrolyzer | 26.3 | kWh /kg H$_2$ |
| Electricity - H$_2$ compressor | 1.5 | kWh /kg H$_2$ |
| Electricity - solution pumps | 2 | kWh/kscf gas |
| Heat - concentrate H$_2$SO$_4$ | 2 | kWh/kg H$_2$SO$_4$ |
| Bromine losses | 0.02% | % per reaction |
| Electricity price (natural gas generator) | 4.3 | ¢/kWh |
| Heat price (natural gas at $5/MMBtu) | 1.7 | ¢/kWh |
| Bromine price | $2 | $/kg |

TABLE 7-5

Cost sensitivites

| Metric | Low | Baseline | High |
|---|---|---|---|
| H$_2$S content | 1% | 4% | 10% |
| Capital cost | 50% | 100% | 200% |
| Maintenance | 2.5% | 5% | 10% |
| Electricity price | 2.1 ¢/kWh, | 4.3 ¢/kWh, | 8.5 ¢/kWh, |
| H$_2$ price | $1/kg | $2/kg | $3/kg |
| H$_2$SO$_4$ price | $0/tonne | $50/tonne | $100/tonne |

TABLE 7-6

Scaling factors

| Equipment | Scaling factor |
|---|---|
| HBr electrolysis stack | 0.9 |
| Power conversion (DC/AC rectifier) | 0.9 |
| Sour-gas absorption column | 0.6 |
| Water scrubber | 0.6 |
| Sulfuric acid distillation column | 0.6 |
| Fluid management (pumps and pipes) | 0.6 |
| H$_2$ drier and compressor | 0.6 |
| H$_2$ storage tank (2,500 psi) | 0.6 |
| Br$_2$/HBr storage system (incl. Br$_2$/HBr) | 0.6 |
| Instrumentation and Controls | 1.0 |
| Structure | 1.0 |

REFERENCES

1 All thermodynamic data is taken from the CRC handbook at STP. Two reactions are shown to illustrate the thermodynamics under different assumptions, with (aq) representing an aqueous 1 molal solution.

2 kgH$_{2eqv}$ represents the amount of the reaction required to eventually yield a kilogram of hydrogen.

3 G. Scheutz, P. Fiebelmann, EURATOM-Communication, COM 3234, 1974; G. Farbman, L. Brecher, Hydrogen production by Water Decomposition Using a combined Electrolytic-Thermochemical Cycle, First World Hydrogen Conference, Miami Beach, paper 9A-29, March 1976.
4 D. van Velzen, et al., Development, design and operation of a continuous laboratory-scale plant for hydrogen production by the mark-13 cycle, Hydrogen Energy Progress III, pg 649-665, 1979; D. van Velzen, et al., Development and design of a continuous laboratory-scale plant for hydrogen production by the mark-13 cycle, International Journal of Hydrogen Energy, Vol 5, pp. 131-139, 1980; D. van Velzen, et al. Status report on the Operation of the Bench-Scale Plant for Hydrogen Energy Production by the Mark-13 Process, Hydrogen Energy Progress III, pg 423, 1980.
5 E. Bilgen, R. K. Joels, An assessment of solar hydrogen production using the mark 13 hybrid process, International Journal of Hydrogen Energy, Vol 10, No. 3, pp. 143-155, 1985
6 H. Langenkamp, D. van Velzen, Ispra 13A Process 'Sulphur Dioxide and Nitrogen Oxides in Industrial Gases: Emission Legislation and Abatement' Kluwer Academic Press 1991.
7 D. van Velzen, The Ispra Flue Gas Desulphurization Process—Research, Development and Marketing Aspects, Corporate communication, 1993; D. van Velzen, H. Langenkamp and A. Martiho, A New Flue Gas Desulphurization Process, Ispra Mark 13B, Symposium 'Energia ed Ambiente verso it 2000' Capri, 3-5 Jun. 1993.
8 Personal communication with Gottfried Besenbruch from General Atomics.
9 U.S. Pat. No. 5,433,828, Method for the removal of hydrogen sulfide and/or carbon disulfide from waste gases, Daniel van Velzen, Heinrich Langenkamp, 1995.
10 Personal communication with Heinrich Langenkamp, and Daniel van Velzen. 2006-2008.
11 G. H. Schuetz, Hydrogen Producing Cycles Using Electricity and Heat—Hydrogen Halide Cycles: Electrolysis of HBr, Int. Journal of Hydrogen Energy, 1977 Vol 1. Pp 379-388; G. H. Schuetz and P. J. Fiebelmann, Electrolysis of Hydrobromic Acid, Int. Journal of Hydrogen Energy, 1980 Vol 5. Pp 305-316; E. N. Balko, J. F. McElroy and A. B. LaConti, Halogen Acid Electrolysis in Solid Polymer Electrolyte Cells, Int. Journal of Hydrogen Energy, 1981 Vol 6. No. 6, Pp 577-587; The Influence of Noble Metal Catalysts on the Electro-chemical Decomposition of H. Feess, K. Koster and G. H. Schuetz, Concentrated Hydrobromic Acid at Graphite Electrodes, Int. Journal of Hydrogen Energy, 1981 Vol 6. No. 4, Pp 377-388; I. Uehara, E. Ishii, H. Ishikawa, M. Nakane, Electrolytic Decomposition of Aqueous Hydrogen Bromide, Nippon Kagaku Kaishi 1981, (2) Pp 221-227; E. N. Balko, Heat Rejection and Thermal Efficiency in Model Hydrogen-Halogen Fuel Cell Systems, Journal of Applied Electrochemistry II (1981) Pp 91-102; W. Kondo, S. Mizuta, Y. Oosawa, T. Kumagai and K. Fujii, Decomposition of Hydrogen Bromide or Iodide by Gas Phase Electrolysis, Bulletin of Chemical Society of Japan, 56, 1983, Pp 2504-2508; N. Miura, K. Ohta, R. Onizuka, N. Yamazoe, Gas Phase Electrolysis of Hydrobromic Acid, Nippon Kagaku Kaishi 1986, (1) Pp 73-78; Y. Shimizu, N. Miura, N. Yamazoe, Gas Phase Electrolysis of Hydrobromic Acid using a PTFE-bonded Carbon Electrode, Nippon Kagaku Kaishi 1987, (8) Pp 1513-1517.
12 Scheutz, G. H., Fiebelmann, P. J., Lalonde, D. R., Electrolysis of Hydrobromic Acid, 1977.
13 Shimizu, Y., Miura, N., Yamazoe, N., Gas-Phas Electrolysis of hydrogen Bromic Acid Using PTFE bonded Carbon Electrode, Int. J. of Hydrogen Energy. Vol 13, No. 6, pp. 345-349, 1988.
14 Balko, E., McElroy, J., LaConti, A., Halogen Acid Electrolysis in Solid Polymer Electrolyte Cells. Int. J. of Hydrogen Energy, Vol 6, No. 6, pp. 577-587, 1981.
15 See prior references for complete review of work done in field.
16 http://www.accessexcellence.org/BF/bf01/arp/bf01p2.php; http://seawifs.gsfc.nasa.gov/OCEAN_PLANET/HTML/ps_vents.html
17 http://suprememastertv.com/bbs/board.php?bo_table=sos&wr_id=509&url=link1_0
18 http://www.treehugger.com/files/2007/08/searching_for_alternative_energy.php
19 http://electrochem.cwru.edu/encycl/art-b01-brine.htm
20 L. Broussard, T. Hamby Jr, and J. Peterson, Drilling and Producing High Pressure Sour Gas Reserves, 11th World Petroleum Congress, London, August 1983.
21 http://www.rigzone.com/news/article.asp?a_id=76449
22 Acid Gas Removal Options for Minimizing Methane Emissions, Occidental Petroleum Corporation, August 2007.
23 http://www.mnforsustain.org/natural_gas_supply_in_decline_youngquist_duncan_1203.htm; http://www.naturalgas.org/business/analysis.asp
24 http://www.eia.doe.gov/oiaf/analysispaper/elasticity/index.html; http://www.utilitysavings.com/Resource/free/Gas_1-yr.gif
25 http://michaelbluejay.com/electricity/cost.html
26 http://www.inchem.org/documents/cicads/cicads/cicad53.htm
27 http://www.infoplease.com/ipa/A0778281.html
28 M. Price, J. Bennett, The High Cost of Canada's Oil and Gas Export Strategy, Natural Resources Defense Council, October 2002.
29 http://www.osha.gov/SLTC/etools/oilandgas/general_safety/h2 s_monitoring.html; http://www.stockinterview.com/News/03042007/molybdenum-energy-US-pipelines.html
30 U.S. Geological Survey, Mineral Commodities Summaries, January 2006 pg. 164-165.
31 http://manure.unl.edu/adobe/v7n10_01.pdf; http://www.mnproject.org/pdf/Haubyrptupdated.pdf
32 Department of Energy, November 1999 website at http://www.net1.doe.gov/publications/press/1999/t1_gasupgrade99.html
33 Swain, E. J., U.S. refinery-sulfur prod. peaked in 1996, Oil & Gas Journal; Mar. 8, 1999; 97 10; pg. 77.
34 T-Raissi, A. Technoeconomic Analysis of Area II Hydrogen Production—Part 1, in Proceedings of the 2001 DOE Hydrogen Program Review, DE-FC36-00G010603, 2001.
35 http://tonto.eia.doe.gov/dnav/pet/hist/mcrslus2 m.htm
36 Energy Information Administration, U.S. Natural Gas Resource Estimates, website at http://www.naturalgas.org/overview/resources.asp
37 Kidnay, A., Parrish, W. Fundamentals of Natural Gas Processing, CRC Press, 2006.
38 www.cbc.ca/news/background/environment/sour_gas.html; http://www.yaleinsider.org/view supportinfo.jsp?infold=10
39 msnmoney.brand.edgar-online.com/EFX_d11/EDGARpro.d11?FetchFilingHTML1?ID=5792057&SessionID=jD3hWZnjVRJFbg9
40 www.shell-me.com/english/apr2002/technology.htm; www.egyptoilgas.com/read article_local.php?NID=245

41 http://www.ec.gc.ca/energ/oilgas/flaring/flaring_general2_e.htm

42 John Squarek and Mike Dawson, Coalbed methane expands in Canada, Oil & Gas Journal, 24 Jul. 2006, p. 37-40.

43 Wells with such high $H_2S$ were initially exploited for their $H_2S$ content and to make sulfur at the beginning of the 21st century.

44 Image courtesy of: Gas Purification Handbook 5th ed. 1997.

45 Confidential conversation with Texas natural gas production engineer.

46 Interview with Rick Manner from KBCat, January 2009

47 http://www.naturalgas.org/naturalgas/processing_ng.asp 48 flickr.com/photos/gord99/280466011/; flickr.com/photos/library_of_congress/2179911364/in/pool-462899@N23

49 http://energypriorities.com/entries/2005/08/nw_symposium_1.php 50 www.osseismic.com/Images/Environmental/flaring.jpg; http://mesaalberta.com/Photos/Sites/index.htm 51 http://www.globalgreenenergyfoundation.org/educational.html 52 University of Alberta—Flare Research Project http://www.ec.gc.ca/cleanair-airpur/caol/OGEB/oilgas/flaring/flaring/exec_summ_e.htm 53 Conversation with Vallejo Refinery.

54 Only Natural Gas feedstock cost (no capital fixed charge) and DOE Hydrogen LHV of 51,682 Btu/lb.

55 http://www.ec.gc.ca/cleanair-airpur/caol/OGEB/oilgas/flaring/flaring_general2_e.htm 56 Hydrogen Analysis Resource Center, 2007 Hydrogen Production Data, hydrogen.pnl.gov/cocoon/morf/hydrogen/article/706

57 Hydrogen Analysis Resource Center, http://hydrogen.pnl.gov/cocoon/morf/hydrogen/article/706

58 USDA Report on ammonia production in the U.S.

59 Balat, M., Potential importance of hydrogen as a future solution to environmental and transportation problems, Int. Jour. Of Hydrogen energy 33 pp. 4013-4039 2008.

60 From Department of Energy Hydrogen Analysis Resource Center: hydrogen.pnl.gov/cocoon/morf/hydrogen/article/706 which references Cryogas International; February 2008; Vol. 46, No. 2 for total U.S. 2007 H2 production of 21.014 million tons, which (if produced from natural gas as 96% of domestic hydrogen is produced) requires 3,120 TBtu of the total 2006 domestic consumption of 23,772 TBtu of natural gas, or 13% of the natural gas consumed. The Booz-Allen-Hamilton (BAH) report cited in the first endnote above quotes that only 10% of U.S. natural gas goes to the chemical industry. The underestimate can be explained by 1) the report referencing old data when less hydrogen was produced because the crude oil being refined was less sour and increased sulfur standards in diesel had not come into effect, or 2) the hydrogen produced from natural gas for refineries was not accounted for in the natural gas consumed by the chemical industry.

61 From Department of Energy Hydrogen Analysis Resource Center: hydrogen.pnl.gov/cocoon/morf/hydrogen/article/706 113,940 Btu of hydrogen requires 156,249 Btu of natural gas and 1,942 Btu of electricity, which (at an average generation efficiency of 33%) requires 5,883 Btu of fossil fuels results in a net hydrogen-from-fossil energy efficiency of 70.3%.

62 Lower Heating Value of H2 at 51,600 Btu/lb.

63 In the 1980's and 90's natural gas cost an average of $2/MMBtu which made hydrogen ~$10/MMBtu.

64 The Hydrogen Economy: Opportunities, Costs, Barriers, and R&D Needs; Committee on Strategies for Future Hydrogen Production and Use, National Research Council, 2004 www.nap.edu/books/0309091632/html 65 www4.nationalacademies.org/news.nsf/isbn/0309091632?OpenDocument 66 Henri Maget Slurry Electrodes for Halogen Electrolysis, U.S. Pat. No. 4,239,607.

67 $H_2O \rightarrow H_2 + \frac{1}{2}O_2$ Electrolytic Potential at 25° C.-1.229 Volt, In actual practice requires 1.8-2.0 Volt, or 21.71-24.12 kWh/lb $H_2$.

68 Production of Hydrogen from Renewable Resource: Final subcontract Report, Energy Systems Group, Rockwell International, December 1983, SERI/STR-231-1875, Darnell, A. J. et al. 74 pp. NTIS Order No. DE84000082

69 One Volt is the equivalent of 12.06 kWh/lb of hydrogen: 1 Faraday or 96,485 Coulombs liberates 1 gram mole of H2, or 1 gram mole of ions. Thus, 1 mole H2=2 e−×96,485 Coulomb×1 Volt×1 hr/3600 sec=53.60 Whr; $H_2$=2.016 gram, Therefore, 1 lb of $H_2$ requires: 53.60 Whr/2.016 g×1000 g/kg=26.59 kWh/2.205 kg/lb=12.06 kWh.

70 Water electrolysis cells may operate up to 70% efficient at lower hydrogen production rates, but in practice operate at 50% efficiency to maximize cell power. www.dti.gov.uk/energy/renewables/publications/pdfs/F0300239.pd 71 http://www.newscientist.com/article/dn11364-hydrogen-injection-could-boost-biofuel-production.html 72 http://www.blm.gov/nstc/air/73

73 EPA, Green Book, 8-Hour Ozone Area Summary. http://www.epa.gov/air/oaqps/greenbk/gnsum.html 74 Danger in the Air: Unhealthy Levels of Air Pollution in 2003, PennEnvironment, September 2004.

75 Methanol synthesis: $CO_2 + 3H_2 \rightarrow CH_3OH + H_2O$, $\Delta H = -9.8$ kCal/mole; Ethanol: $2CH_3OH \rightarrow CH_3CH_2OH + H_2O$, $\Delta H = -20.6$ kCal/mole.

76 Brookhaven National Laboratory, General Electric Co., Bechtel, Oronzio de Nora, the National Fire Protection Association, Compressed Gas Association, Association of Casualty and Surety Companies, Manufacturing Chemists Association, National Safety Council, American Conference of Governmental Industrial Hygienists, I. N. Sax: Hazardous Industrial Chemicals, Matheson Gas Products, and the Manufacturing Chemists Association.

77 R. Bradshaw, R. Larson, Production of hydrobromic acid from bromine and methane for hydrogen production, Proceedings of 2001 DOE Hydrogen program review, NREL/CP-570-30535, 2001

78 http://www.sandia.gov/hydrogen/research/production/reactionKinetics.html 79 http://www.grt-inc.com/go/technology/grt-technology/

80 M. Menkovskii, N. Petrov, K. Litvin, D. Chernayskii, Studies on the miscibility of bromine, hydrobromic acid and water, Journal of Inorganic Chemistry, USSR, pg 215-221, 1956.

81 "Sulphuric acid", Encyclopedia Britannica, 26 (11th ed.), 1910-1911, pp. 65-69; Conversations with both Jim Keller and Daniel van Velzen.

82 http://www.engineeringtoolbox.com/gases-solubility-water-d_1148.htm

83 Handbook of X-ray Photoelectron Spectroscopy, J. F. Moulder, W. F. Stickle, P. E. Sobol, and K. D. Bomben, published by Perkin-Elmer Corp., 1992, Eden Prairie, Minn., USA.

84 http://www.purafiltracion.com/Puracarb.pdf
85 http://www.theoildrum.com/node/6488#more
86 http://www.rigzone.com/news/article.asp?a_id=49533
87 Interview with Andrew Kendrick.
88 It is common in the oil & gas industry to express quantities in English units. Whereas this thesis attempts to use SI units whenever possible, for the purpose of describing gas flows, the more standard English unit system is adopted.
89 Gas Purification Handbook and multiple interviews.
90 Material refers to the total equipment costs in prior table.
91 Assume $1 million in R&D expense is allocated over 200 units.
92 A google search found several 100 kW generators commercially available for $2,000.
93 Market Innovations Group.
94 Private communication with major hydrogen supplier.
95 Sour-gas conference in Calgary, 2009.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A process for desulphurization and hydrogen recovery from a sour gas influent stream including an amount of methane and/or ethane and/or carbon dioxide gas and an undesirable amount of hydrogen sulfide, said process comprising:

a gas-liquid reactor column structured to facilitate reaction of said sour gas influent stream with an amount of aqueous bromine in a hydrobromic acid and sulfuric acid solution, wherein said amount of bromine is presented to said sour gas influent stream at a temperature not to exceed 400 Celsius, said reactor structured to produce a gaseous effluent stream comprising substantially all of said amount of methane and/or ethane and/or carbon dioxide gas with some trace amount of bromine and/or hydrogen bromide, said reactor structured to produce liquid effluent stream comprising an aqueous solution of hydrobromic acid, sulfuric acid, and/or solid sulfur with some trace amount of aqueous bromine, a filter which is used to remove solid sulfur and/or sulfuric acid from the reactor liquid effluent stream, a first absorber structured to separate bromine, hydrogen bromide and/or water vapor from said methane and/or ethane and/or carbon dioxide gas in said gaseous effluent stream at a temperature and pressure less than said reactor, said first absorber further structured to discharge a first amount of a dilute aqueous bromine and hydrobromic acid solution, an electrolyzer structured to electrolytically disassociate the filtered dilute aqueous bromine, hydrobromic acid and sulfuric acid liquid effluent stream solution into an aqueous solution of more concentrated bromine and less concentrated hydrobromic acid in same sulfuric acid, and said electrolyzer further structured to produce an amount of hydrogen gas and water vapor via dissociation of said hydrobromic acid solution at a temperature not to exceed 150 Celsius and a pressure not to exceed 1000 psi, a second absorber structured to separate bromine and dilute hydrogen bromide from said hydrogen gas produced via dissociation of said hydrobromic acid solution at a temperature not to exceed 150 Celsius and a pressure not to exceed 1000 psi, and said second absorber further structured to discharge a second amount of a dilute aqueous hydrobromic acid solution.

2. The process as recited in claim 1 wherein said reactor and/or first absorber comprises a packed column made of glass, ceramic, PVC and/or PVDF materials.

3. The process as recited in claim 1 wherein said first and/or second absorber includes an amount of a solid absorbent material to remove any trace amount of hydrogen sulfide, bromine and/or hydrogen bromide.

4. The process as recited in claim 3 further comprising a cooler structured to reduce the temperature of said hydrogen gas from said second absorber to reduce the vapor pressure of any trace chemicals.

5. The process as recited in claim 4 further comprising a dryer structured to remove said water vapor from said hydrogen gas in the effluent of said second absorber.

6. The process as recited in claim 1 wherein said electrolyzer comprises at least one proton exchange membrane cell operated at up to 2.250 Amps/m$^2$ current density.

7. The process as recited in claim 6 wherein said electrolyzer comprises a plurality of proton exchange membrane cells.

8. The process as recited in claim 7 wherein said plurality of proton exchange membrane cells are disposed in a series configuration in an electrolyzer stack.

9. A process for desulphurization and hydrogen recovery from a sour gas influent stream including an amount of methane gas and an undesirable amount of hydrogen sulfide, said process comprising:

a reactor column structured to facilitate reaction of said sour gas influent stream with 1 to 20 wt % amount of bromine in a 5-48 wt % hydrobromic acid solution, wherein said amount of bromine is presented to said sour gas influent stream at a temperature not to exceed 400 Celsius, said reactor structured to produce a gaseous effluent stream comprising substantially all of said amount of methane gas, said reactor structured to produce an aqueous effluent stream comprising an aqueous solution of hydrobromic acid, sulfuric acid, and/or solid sulfur, a first absorber structured to separate carbon dioxide gas trace bromine and hydrogen bromide and water vapor from said methane gas in said gaseous effluent stream, said first absorber further structured to discharge a first amount of a dilute aqueous bromine and hydrobromic acid solution, an electrolyzer structured to electrolytically disassociate hydrobromic acid solution into an aqueous solution of more dilute hydrobromic acid and more concentrated bromine, said electrolyzer further structured to produce an amount of hydrogen gas and water vapor via dissociation of said hydrobromic acid solution, said electrolyzer comprises a plurality of proton exchange membrane cells, wherein said plurality of proton exchange membrane cells are disposed in a series configuration in an electrolyzer stack, a second absorber structured to separate bromine and hydrogen bromide from said hydrogen gas produced via dissociation of said hydrobromic acid solution, said second absorber further structured to discharge a second amount of a dilute aqueous hydrobromic acid solution.

10. The process as recited in claim 9, wherein the stoichiometric ratio of bromine in the liquid solution introduced into the reactor to hydrogen sulfide in the sour gas influent stream is close to a 1:1 ratio so as to encourage the production of solid sulfur.

11. The process as recited in claim 9, wherein the stoichiometric ratio of bromine in the liquid solution introduced into the reactor to hydrogen sulfide in the sour gas influent stream is close to a 1:4 ratio so as to encourage the production of sulfuric acid.

\* \* \* \* \*